US010716865B2

(12) United States Patent
Sen Gupta et al.

(10) Patent No.: US 10,716,865 B2
(45) Date of Patent: *Jul. 21, 2020

(54) HETEROMULTIVALENT PARTICLE COMPOSITIONS

(71) Applicant: Case Western Reserve University, Cleveland, OH (US)

(72) Inventors: Anirban Sen Gupta, Cleveland, OH (US); Madhumitha Ravikumar, South Park, PA (US); Christa Modery, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/832,526

(22) Filed: Dec. 5, 2017

(65) Prior Publication Data

US 2018/0318443 A1 Nov. 8, 2018

Related U.S. Application Data

(63) Continuation of application No. 14/827,785, filed on Aug. 17, 2015, now Pat. No. 9,833,518, which is a continuation-in-part of application No. 13/863,005, filed on Apr. 15, 2013, now Pat. No. 9,107,963.

(60) Provisional application No. 61/623,607, filed on Apr. 13, 2012.

(51) Int. Cl.
*A61K 38/49* (2006.01)
*A61K 47/69* (2017.01)
*A61K 49/00* (2006.01)
*A61K 47/62* (2017.01)

(52) U.S. Cl.
CPC .......... *A61K 47/6911* (2017.08); *A61K 38/49* (2013.01); *A61K 47/62* (2017.08); *A61K 49/0032* (2013.01); *A61K 49/0041* (2013.01); *A61K 49/0043* (2013.01); *A61K 49/0084* (2013.01); *C12Y 304/21068* (2013.01)

(58) Field of Classification Search
None
See application file for complete search history.

(56) References Cited

U.S. PATENT DOCUMENTS 9,107,963 B2 * 8/2015 Sen Gupta ............. A61K 38/49
9,833,518 B2 * 12/2017 Sen Gupta ......... A61K 49/0084
2005/0004035 A1 1/2005 Molenaar et al.

FOREIGN PATENT DOCUMENTS

WO 98/36778 A1 8/1998
WO 2010/008792 A1 1/2010

OTHER PUBLICATIONS

Appeldooen et al. (J Biol Chem. Mar. 21, 2003;278(12):10201-7).
Braunwald et al. (Clin. Cardiol. (Suppl. 1) 31, 3, 1-17-1-20 (2008)).
Huang X. et al. (Adv. Mater. 2009, 21, 1-31).
Yabushita et al. (Circulation. Sep. 24, 2002;106(13):1640-5).
Gawaz (Cardiovascular Research 61 (2004) 498-511).
Lestini, Brian J., "Surface Modification of Liposomes for Selective Cell Targeting in Cardiovascular Drug Deliver", Journal of Controlled Release 78 (2002) 235-247.
Molenaar, Tom J.M., "Specific Inhibition of P-Selectin-Mediated Cell Adhesion by Phase Display-Derived Peptide Antagonists" Blood, Nov. 15, 2002, vol. 100, No. 10, pp. 3570-3577.
Sen Gupta, Anirban, "RGD-modified liposomes targeted to activated platelets as a potential vascular drug delivery system", Thromb Haemost 2005; 93; 106-114.
Huang, et al., Affinity manipulation of surface-conjugated RGD peptide to modulate binding of liposomes to activated platelets, Biomaterials 29 (2008) 1676-1685.
Srinivasan, et al., "In Vitro and In Vivo platelet targeting by cyclic RGD-modified liposomes", J_ Biomed Mater Res A, Jun. 1, 2010;93(3):1004-1015.

* cited by examiner

*Primary Examiner* — Sergio Coffa
(74) *Attorney, Agent, or Firm* — Tarolli, Sundheim, Covell & Tummino LLP

(57) ABSTRACT

A composition for use in diagnostic and therapeutic applications includes a heteromultivalent nanoparticle or microparticle having an outer surface and a plurality of targeting moieties conjugated to the surface of the nanoparticle or microparticle, the targeting moieties includes a first activated platelet targeting moiety and a second activated platelet targeting moiety.

12 Claims, 31 Drawing Sheets

Specification includes a Sequence Listing.

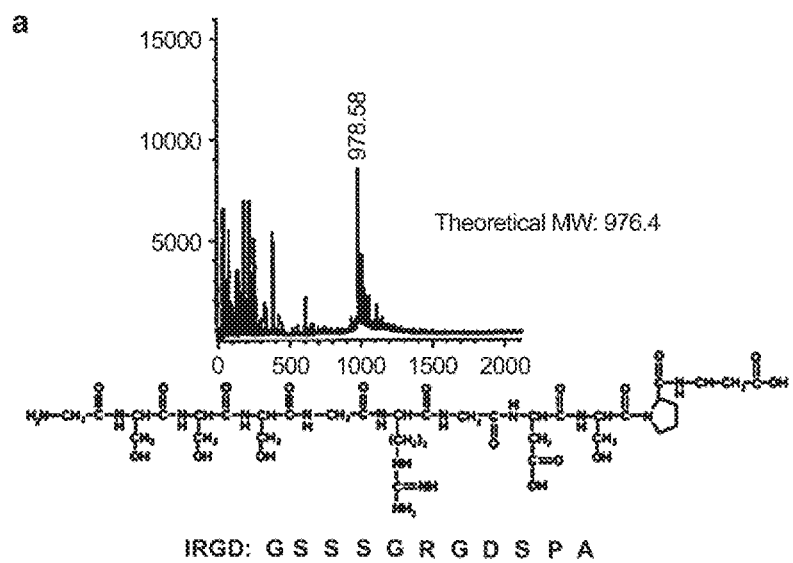
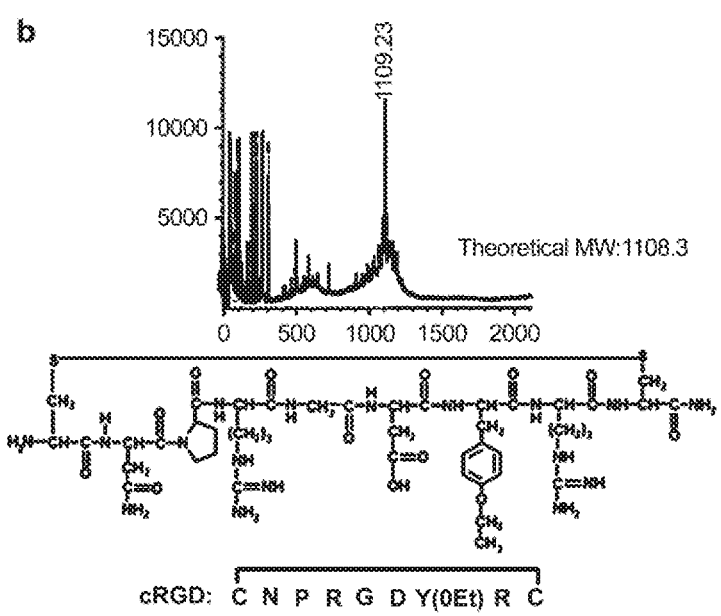
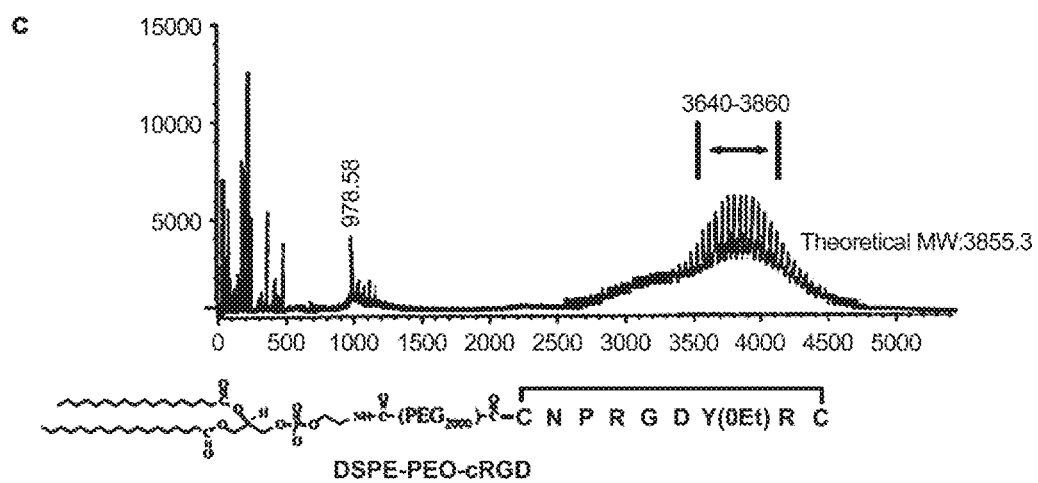
Figs. 17A-C

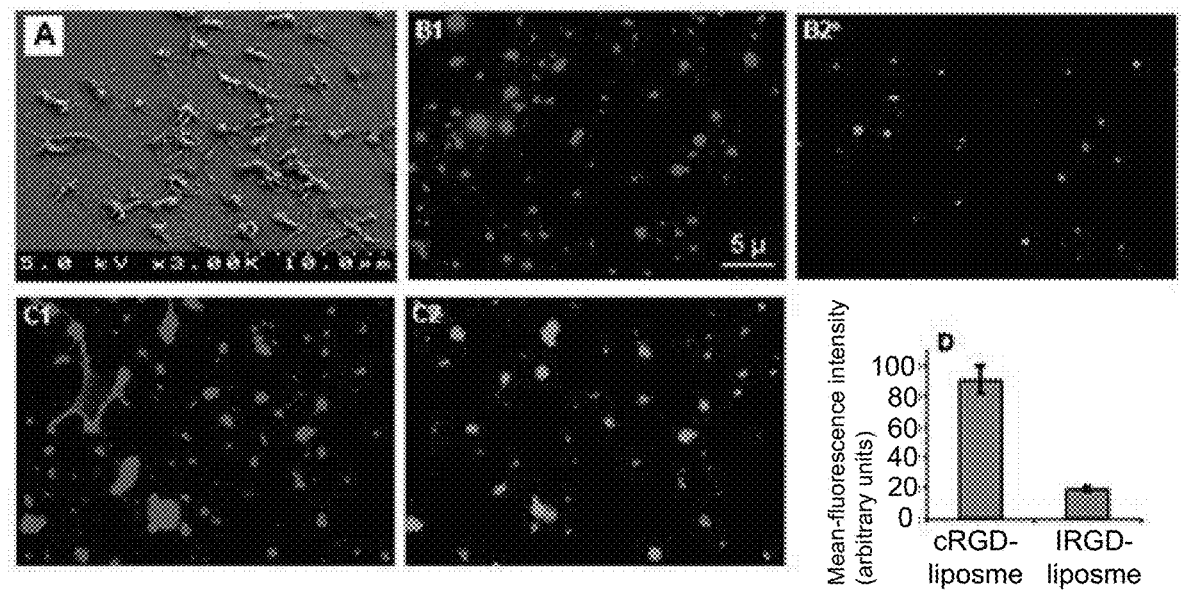
Figs. 19A-D
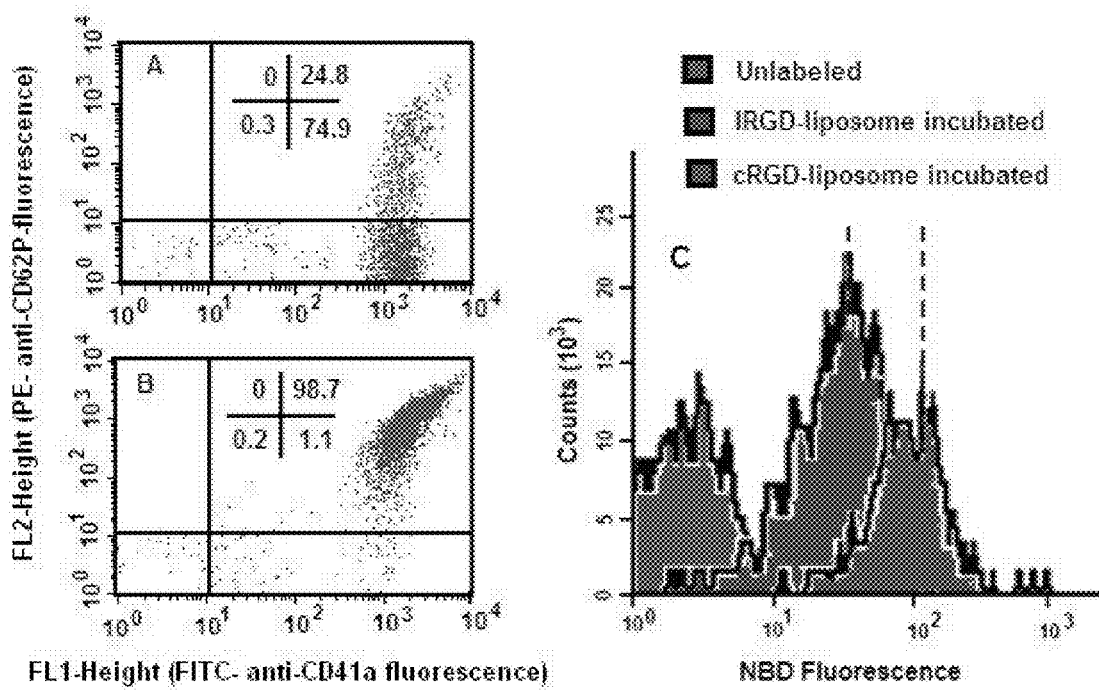
Figs. 20A-C

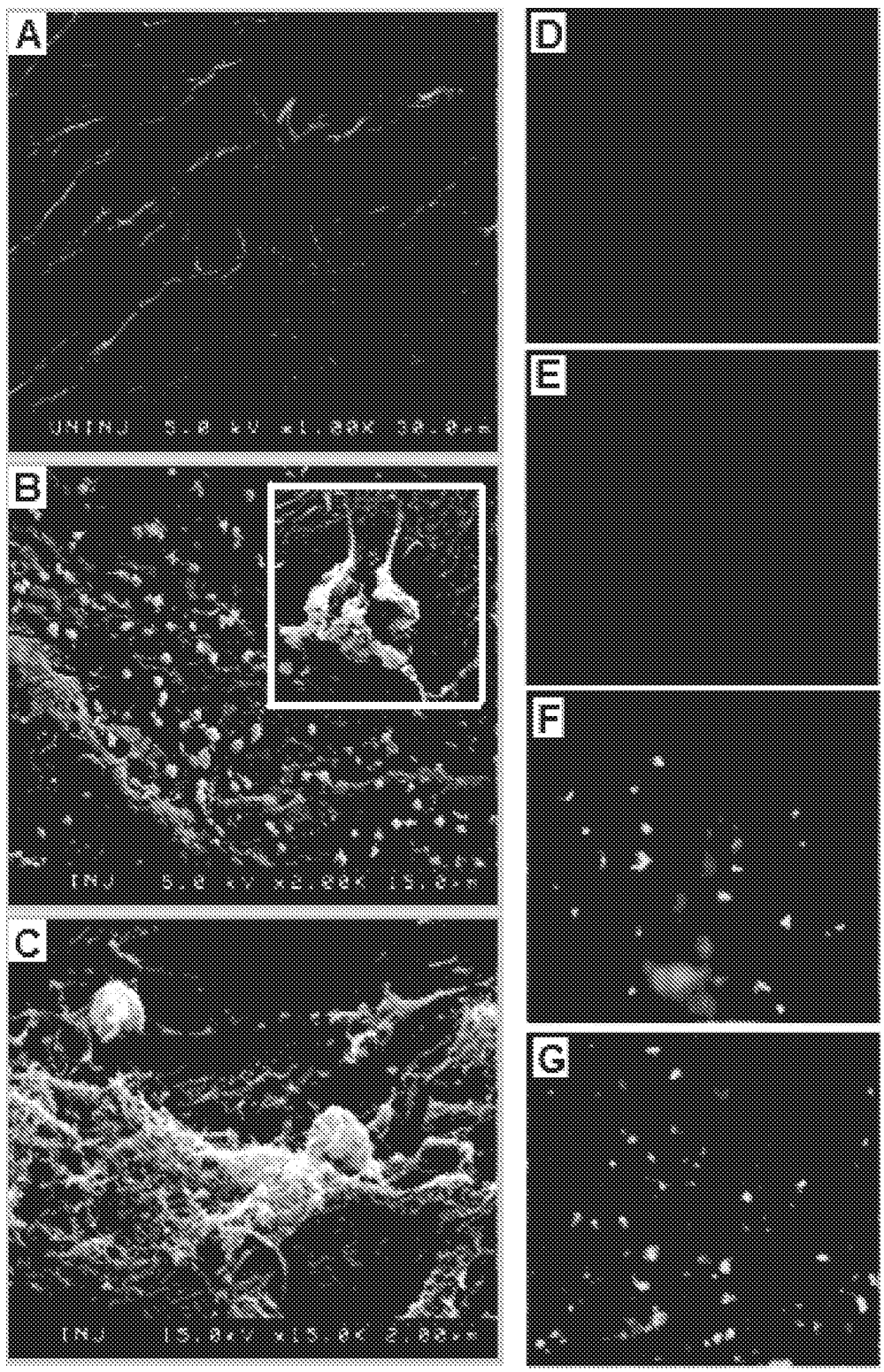
Figs. 21A-G

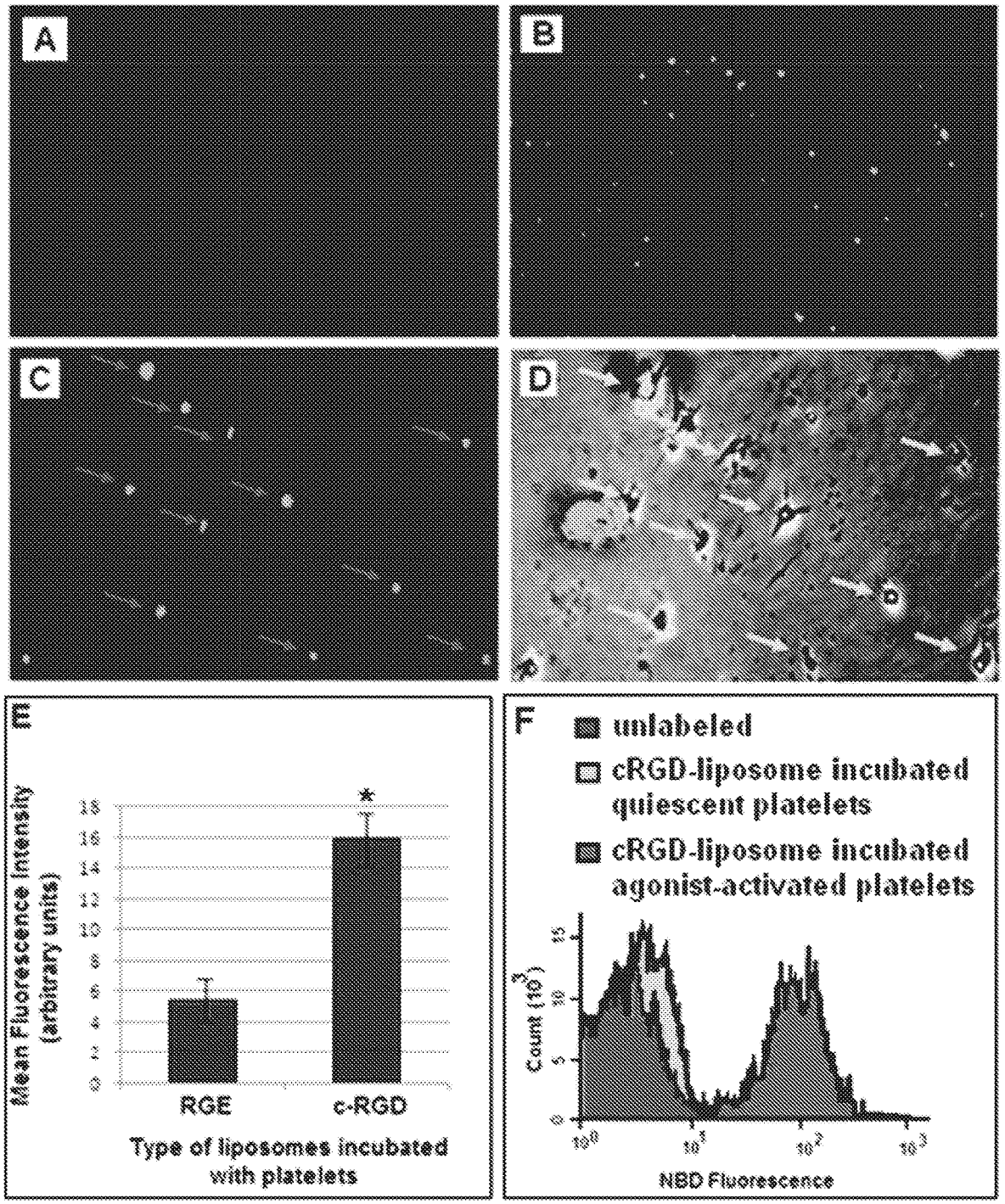
Figs. 23A-F

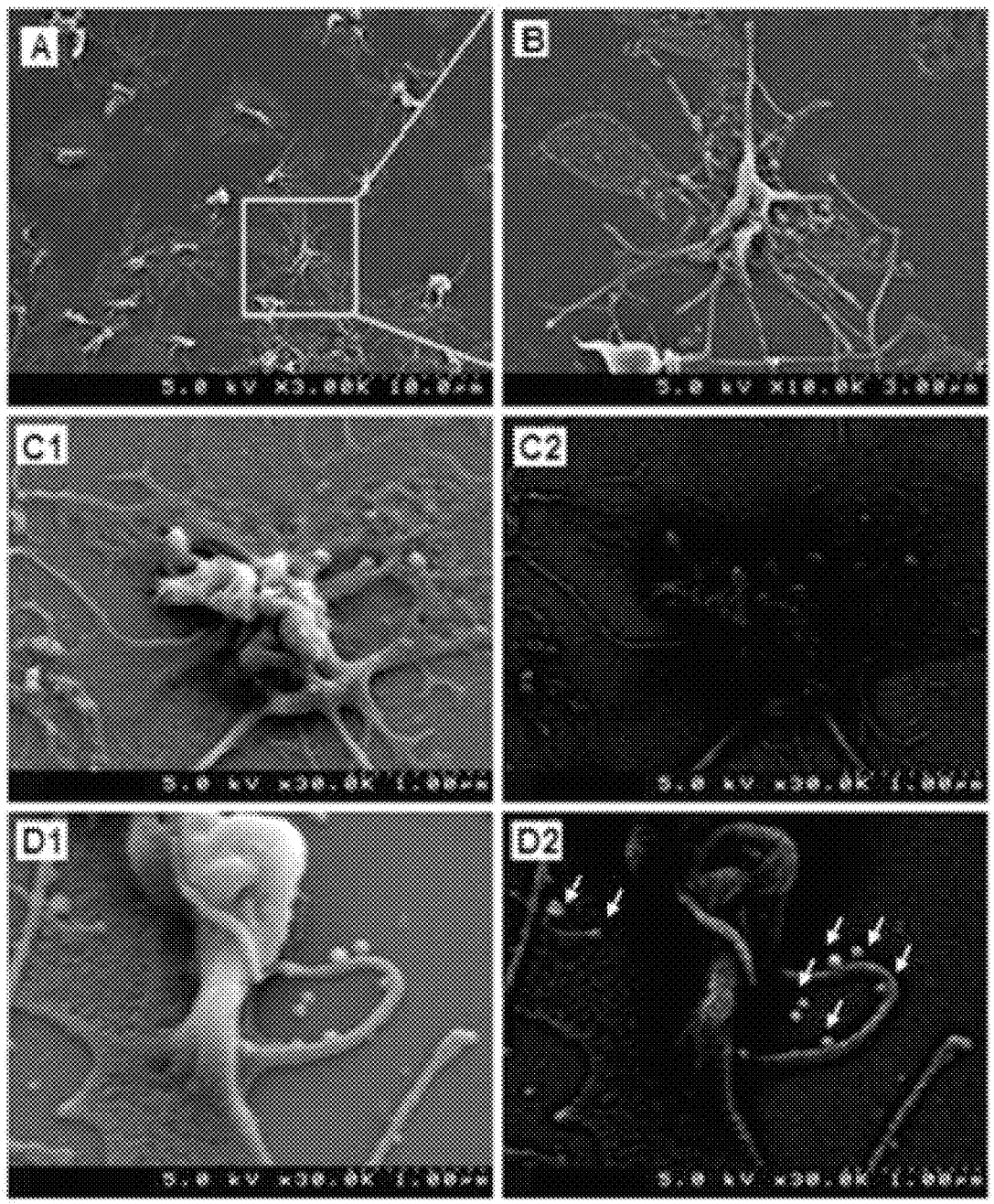
Figs. 24A-D2

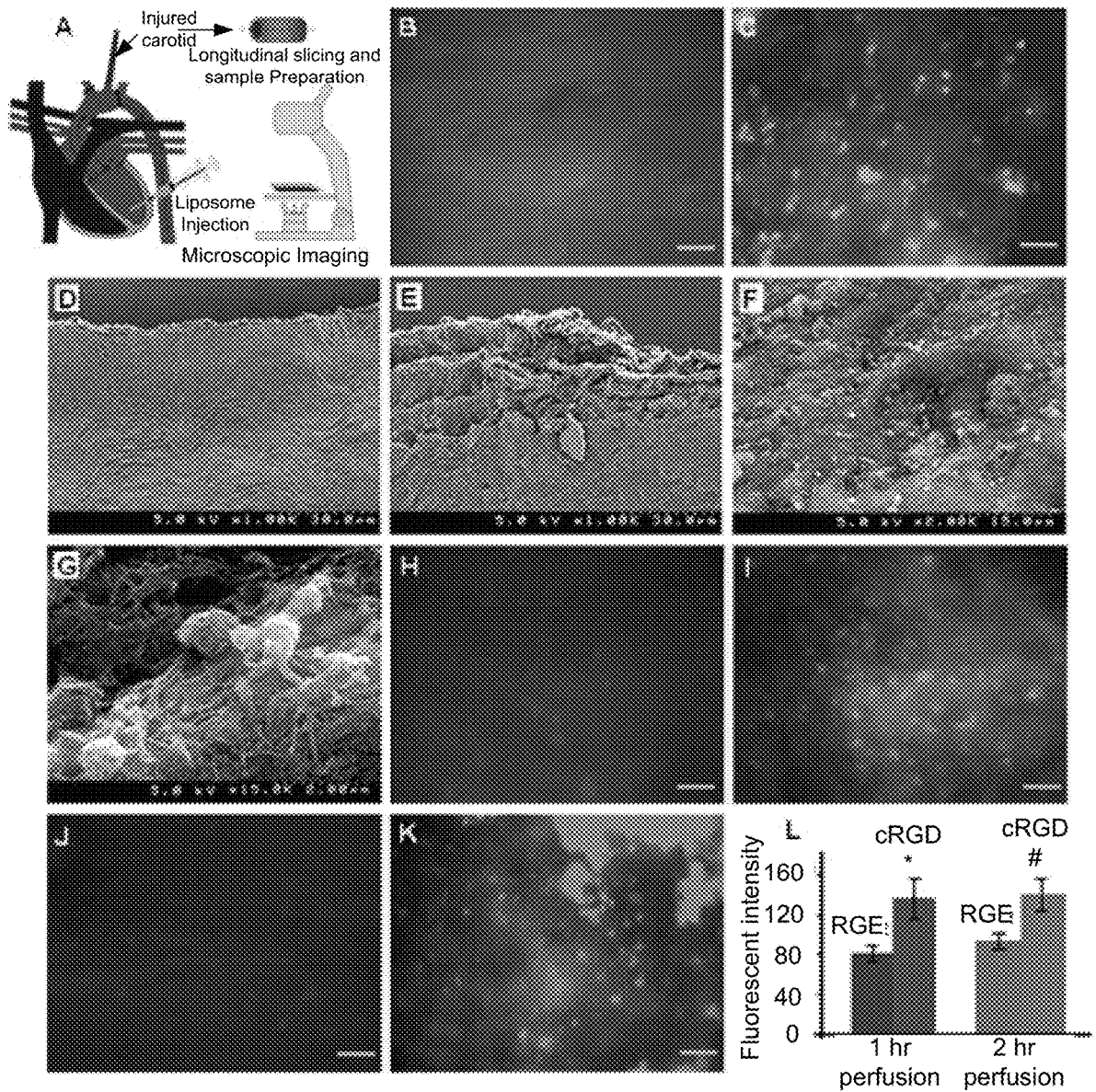
Figs. 25A-L

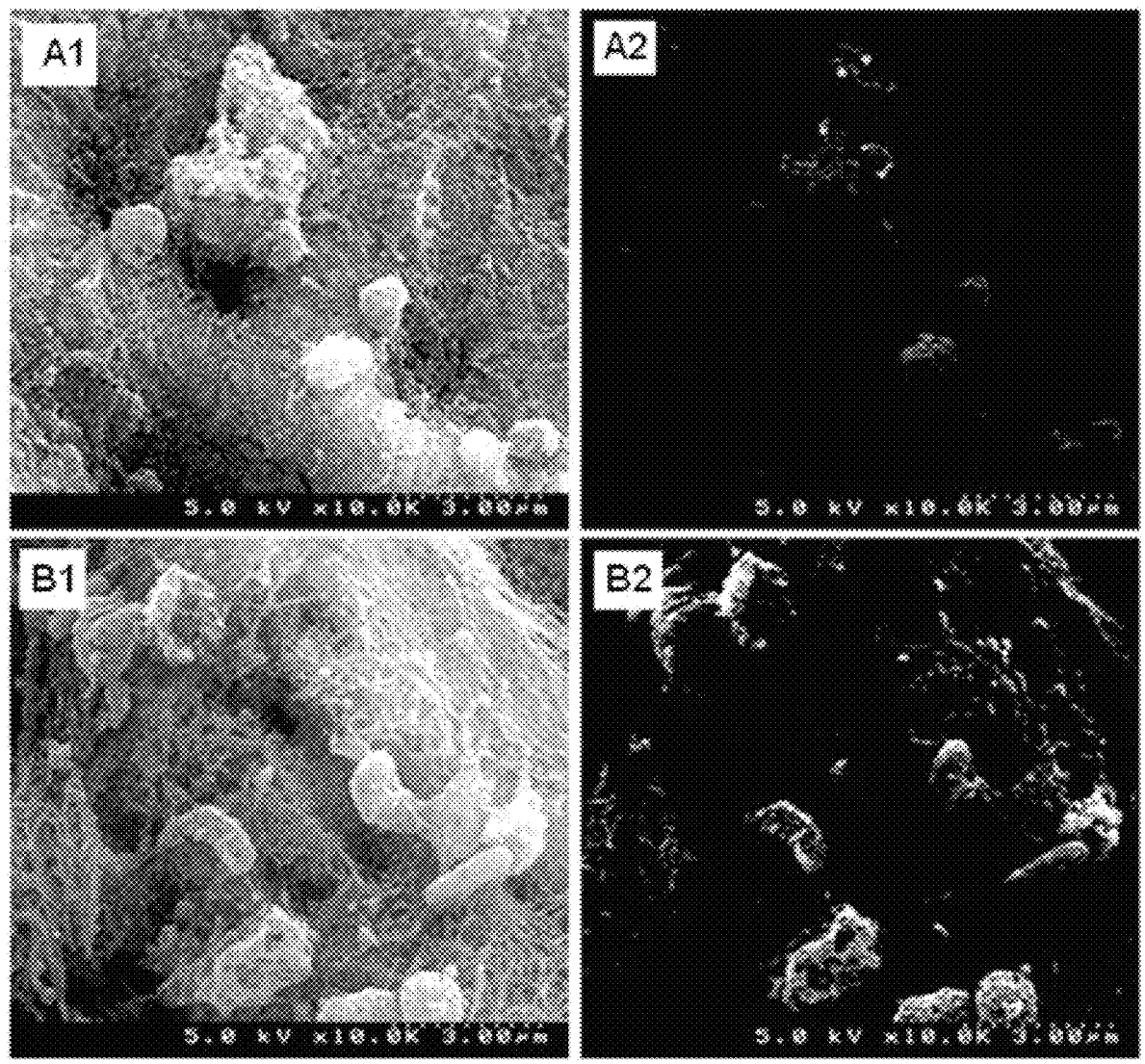
Figs. 26A1-B2

HETEROMULTIVALENT PARTICLE COMPOSITIONS

RELATED APPLICATION

This application is continuation in part of U.S. patent application Ser. No. 13/863,005 filed Apr. 15, 2013, now U.S. Pat. No. 9,107,963, which claims priority from U.S. Provisional Application No. 61/623,607 filed Apr. 13, 2012, the subject matter of which are incorporated herein by reference in their entirety.

TECHNICAL FIELD

This application relates to heteromultivalent nanoparticle or microparticle compositions selective for activated platelets and to the use of the heteromultivalent nanoparticle or microparticle compositions for diagnostic and therapeutic applications.

BACKGROUND

Vascular diseases, leading to thrombo-occlusive and ischemic end points, are the leading cause of tissue morbidity and mortality in the United States and globally. Current treatments for vascular disease include both endovascular and pharmacotherapy strategies. For example, angioplasty/stenting, which is invasive, can cause restenosis and secondary thrombotic events. In addition, bypass grafting is both invasive and can lead to graft failure. In vascular disease manifestations, such as atherosclerotic plaque progression and rupture as well as events leading to thrombosis and restenosis, disease site-selective delivery of therapeutic agents (e.g., thrombolytic or anti-proliferative drugs) and diagnostic probes (e.g., MRI or CT contrast agents) can provide significantly enhanced treatment efficacy compared to systemic administration of the same agents. This is because, in direct systemic administration, a significant fraction of the agents may get cleared rapidly or may get deactivated by plasma action, thereby reducing their therapeutic concentration at the target disease site. Moreover, systemic distribution of the drug can cause unwanted side effects in un-involved tissues, such as systemic coagulopathic and hemorrhagic effects. Thus, methods allowing for disease site-selective delivery can have a significant clinical benefit.

SUMMARY

Embodiments described herein relate to a heteromultivalent nanoparticle or microparticle composition for use in diagnostic and therapeutic applications. The composition includes a heteromultivalent nanoparticle or microparticle having an outer surface and a plurality of targeting moieties conjugated to the surface of the nanoparticle or microparticle. The targeting moieties can include a first activated platelet targeting moiety and a second activated platelet targeting moiety. The composition is capable of binding activated platelets at a thrombus site under a hemodynamic shear environment. In some embodiments, the nanoparticle or microparticle can include a liposome.

In some embodiments, the first activated platelet targeting moiety includes a GPIIb-IIIa-binding peptide and the second activated platelet targeting moiety includes a p-selectin binding peptide. The GPIIb-IIIa-binding peptide can include a RGD small peptide and the p-selectin binding peptide can include a small peptide having the amino acid sequence EWVDV (SEQ ID NO:1). In some embodiments, the RGD small peptide has an amino acid sequence of SEQ ID NO:3, and the p-selectin binding peptide has the amino acid sequence of SEQ ID NO:5. The ratio of GPIIb-IIIa-binding peptide to p-selectin binding peptide provided on the nanoparticle or microparticle surface can be about 80:20 to about 20:80. The GPIIb-IIIa-binding peptide and p-selectin binding peptide provided on the nanoparticle or microparticle surface can have a total mol % of about 5 to about 20 with respect to total lipid content.

The first and second activated platelet targeting moieties can be conjugated to the nanoparticle or microparticle surface with PEG linkers. The first and second activated platelet targeting moieties can be spatially or topographically arranged on the nanoparticle or microparticle surface such that the first and second activated platelet targeting moieties do not spatially mask each other and the nanoparticle or microparticle is able to bind to an activated platelet with exposed activated platelet receptors thereby enhancing retention of the nanoparticle or microparticle construct onto activated platelets under hemodynamic flow.

In some embodiments, the composition further includes a therapeutic and/or imaging agent. The agent can be encapsulated within the nanoparticle or microparticle construct. The therapeutic agent can be selected from the group consisting of an anti-thrombotic agent and a thrombolytic agent. The therapeutic agent can also include tissue plasminogen activator (tPA). In some embodiments, the nanoparticle or microparticle further includes Golden Nanorods (GNRs) conjugated to the surface, the GNRs can allow photothermal destabilization of the nanoparticle or microparticle construct and therapeutic and/or imaging agent release in response to near-infrared (NIR) light.

The application also relates to a method of delivering a therapeutic and/or imaging agent to activated platelets in a subject. The method includes administering to the subject a composition. The composition includes a therapeutic agent. The composition also includes heteromultivalent nanoparticle or microparticle having an outer surface and a plurality of targeting moieties conjugated to the surface of the nanoparticle or microparticle. The targeting moieties can include a first activated platelet targeting moiety and a second activated platelet targeting moiety. The composition is capable of binding activated platelets at a thrombus site under a hemodynamic shear environment. In some embodiments, the nanoparticle or microparticle can include a liposome.

In some embodiments, the first activated platelet targeting moiety includes a GPIIb-IIIa-binding peptide and the second activated platelet targeting moiety includes a p-selectin binding peptide. The GPIIb-IIIa-binding peptide can include a RGD small peptide, and the p-selectin binding peptide can include a small peptide having the amino acid sequence EWVDV (SEQ ID NO:1). In some embodiments, the RGD small peptide has an amino acid sequence of SEQ ID NO:3, and the p-selectin binding peptide has the amino acid SEQ ID NO:5. The ratio of GPIIb-IIIa-binding peptide to p-selectin binding peptide provided on the nanoparticle or microparticle surface can be about 80:20 to about 20:80. The GPIIb-IIIa-binding peptide and p-selectin binding peptide provided on the nanoparticle or microparticle surface can have a total mol % of about 5 to about 20 with respect to total lipid content.

The first and second activated platelet targeting moieties can be conjugated to the nanoparticle or microparticle surface with PEG linkers. The first and second activated platelet targeting moieties can be spatially or topographically arranged on the nanoparticle or microparticle surface such that the first and second activated platelet targeting moieties do not spatially mask each other and the nanoparticle or microparticle is able to bind to an activated platelet with exposed activated platelet receptors thereby enhancing retention of the nanoparticle or microparticle onto activated platelets under hemodynamic flow.

The therapeutic agent can be selected from the group consisting of an anti-thrombotic agent and a thrombolytic agent. The therapeutic agent can also include tissue plasminogen activator (tPA). In some embodiments, the nanoparticle or microparticle further includes Golden Nanorods (GNRs) conjugated to the surface. The GNRs can allow photothermal destabilization of the nanoparticle or microparticle construct and therapeutic and/or imaging agent release in response to near-infrared (NIR) light.

The application further relates to a method of treating an occlusive vascular disease in a subject. The method includes administering to the subject a composition. The composition includes a therapeutic agent. The composition also includes heteromultivalent nanoparticle or microparticle having an outer surface and a plurality of targeting moieties conjugated to the surface of the nanoparticle or microparticle. The targeting moieties include a first activated platelet targeting moiety and a second activated platelet targeting moiety. The composition is capable of binding activated platelets at a thrombus site under a hemodynamic shear environment.

In some embodiments, the nanoparticle or microparticle can further includes Golden Nanorods (GNRs) conjugated to the surface, the GNRs allowing photothermal destabilization of the nanoparticle or microparticle construct and therapeutic and/or imaging agent release in response to near-infrared (NIR) light.

In some embodiments, the occlusive vascular disease is selected from the group consisting of stroke, myocardial infarction, peripheral arterial diseases and deep vein thrombosis.

BRIEF DESCRIPTION OF THE DRAWINGS

FIGS. 17(A-C) illustrate the amino acid sequence structure and corresponding mass spectral (MALDI-TOF) data for platelet GPIIb-IIIa-targeted (a) linear RGD), (b) cyclic RGD and (c) lipopeptide conjugate DSPE-PEG-cRGD.

FIGS. 19(A-D) are scanning electron microscopy (SEM) images confirming the presence of activated platelet monolayer on collagen-coated glass coverslip surface (A); co-incubation of active platelets with AlexaFluor-546-labeled fibrinogen and NBD-labeled peptide-modified liposomes resulted in simultaneous platelet-binding of both, and hence enabled dual fluorescence imaging of the same field of view; comparison of fluorescence images showed similar level of AlexaFluor-546 fluorescence for lRGD- (B1) and cRGD-liposome (C1) incubated platelets suggesting similar level of fibrinogen binding; NBD-fluorescence, however, was significantly enhanced for cRGD-liposome incubated sample (C2), compared to lRGD-liposome incubated sample (B2) as suggested by the mean fluorescent intensity data (D); this indicates enhanced binding of cyclic RGD-modified liposomes to activated platelets.

FIGS. 20(A-C) illustrate histograms showing flow cytometry studies on platelet-liposome interactions in vitro; platelet activation level was confirmed by co-labeling platelets in human whole blood aliquots with FITC-anti-CD41a (antibody to GPIIb-IIIa) and PE-antiCD62P (antibody to P-selectin), (A) before and (B) after addition of agonist ADP; FIG. 20(C) is a graphical representation showing that incubation of activated platelets with NBD-labeled peptide-modified liposomes enhanced NBD fluorescence for cRGD-liposome incubated sample compared to lRGD-liposome incubated sample, over background (unlabeled).

FIG. 21 (A-G) illustrate in vivo targeting of RGD-modified liposomes in a rat carotid injury model; SEM image of (A) uninjured luminal surface of carotid artery shows characteristic spindle shaped endothelial cells and extracellular matrix fibers; following catheter-induced injury, SEM image of the luminal surface shows (B) numerous adhered platelets in activated state (B, inset, magnified); repurfusion of blood through the injury site results in acute thrombotic and coagulatory event, as evidenced by (C) SEM image of the fibrin clot on the luminal surface; exposure of injured surface to NBD-labeled lRGE-, lRGD-, and cRGD-liposomes via an in vivo injection of respective liposome formulation, results in enhanced binding of (G) cRGD-liposomes to the injury site, comparted to (E) lRGE- and (F) lRGD-liposomes, as evidenced by ex-vivo fluorescence imaging; (D) shows the fluorescence image of the luminal surface without exposure to NBD-labeled liposomes, for reference.

FIGS. 23(A-F) are representative fluorescence and phase contrast microscopy images from in vitro studies of active platelet targeting by peptide-modified fluorescently labeled liposomes; (A) RGE liposome-incubated sample showed minimal fluorescence, while (B) cRGD-liposome incubated sample showed significantly enhanced fluorescence; parallel analysis of cRGD liposome-incubated sample with (C) fluorescence and (D) phase contrast microscopy provided evidence for one-to-one correspondence of fluorescence spots with active platelets, thereby emphasizing that the liposome binding is platelet-specific; (E) represents the surface-averaged fluorescence intensity analysis of the RGE-liposome incubated and the cRGD-liposome incubated samples; (F) shows representative flow cytometry data of NBD fluorescence intensity histogram overlay for platelets without any liposome incubation, with liposome incubation but without ADP pre-incubation (predominantly inactive platelets) and with liposome incubation after ADP pre-incubation (predominantly active platelets), establishing that the NBD-labeled cRGD-liposomes have specific enhanced binding to activated platelets.

FIGS. 24(A-D2) are representative images from SEM studies of active platelet targeting by peptide-modified Nanogold-labeled liposomes; SEM analysis of collagen-coated coverslip exposed to human platelet suspension in presence of ADP showed (A) monolayer of adhered platelets which were in highly activated condition as evidenced by (B) highly folded membrane structure, 'spread' morphology and branched out pseudopods; SEM images in secondary electron mode of (C1) RGE-liposome-incubated platelet and (D1) cRGD-liposome-incubated platelet showed similar membrane morphology and vesicular structures, but corresponding images in backscatter mode showed (C2) minimal gold contrast enhancement on the membrane of RGE-liposome-incubated platelet, while (D2) significant contrast enhancement of the membrane of cRGD-liposome-incubated platelet; in addition, multiple bright spherical vesicular structures (arrowheads in D2) were visible on cRGD-liposome-incubated platelet, which are possibly intact liposomes adhered on the membrane and pseudopods.

FIGS. 25(A-L) are representative ex vivo images from studies of active platelet binding of peptide-modified fluorescently labeled liposomes in vivo in a rat carotid injury restenosis model; (A) shows the schematic of the in vivo model used in the study; (B) and (D) show representative fluorescence and SEM images of the carotid luminal surface without injury; (E) is an SEM image of the carotid luminal surface immediately after frictional injury with inflated balloon catheter, showing significant wall damage and endothelial denudation; after 1 hr of blood repurfusion through such injured carotid, SEM image of excised sections showed (F) numerous adhered platelets and upon magnification (G) arrested platelets in dense fibrin mesh were visible, signifying acute thrombotic environment; the presence of adhered platelets was confirmed by (C) fluorescence imaging after staining the injured section with FITC-tagged anti-rat CD42d (stains platelet GPV); introduction of fluorescently labeled RGE-liposomes in the injured section after (H) 1 hr and (J) 2 hr blood repurfusion showed only minimal staining of platelets; in contrast, introduction of fluorescently labeled cRGD liposomes showed significant platelet staining in both (I) 1 hr and (K) 2 hr repurfusion situations; for 2 hr repurfusion sections, highly fluorescent clumps of aggregated platelets were also visible; (L) statistical analysis of fluorescence intensity from images of liposome exposed carotid sections for several batches of animals, confirmed the enhanced binding of cRGD-liposomes at the injury site.

FIGS. 26(A1-B2) are representative ex vivo SEM images from studies of active platelet targeting by peptide modified Nanogold-labeled liposomes in vivo in a rat carotid injury restenosis model; the secondary electron mode images of both (A1) RGE-liposome-incubated and (B1) cRGD-liposome-incubated samples showed similar acute thrombotic environment with platelets arrested in dense fibrin mesh, but the corresponding backscatter image (A2) of RGE-liposome-incubated sample showed only minimal contrast enhancement while the backscatter image (B2) of cRGD-liposome-incubated sample showed substantial contrast enhancement of cellular structures arrested in the fibrin mesh, suggesting enhanced binding of Nanogold-labeled cRGD-liposomes to platelets.

DETAILED DESCRIPTION

Figure 1:
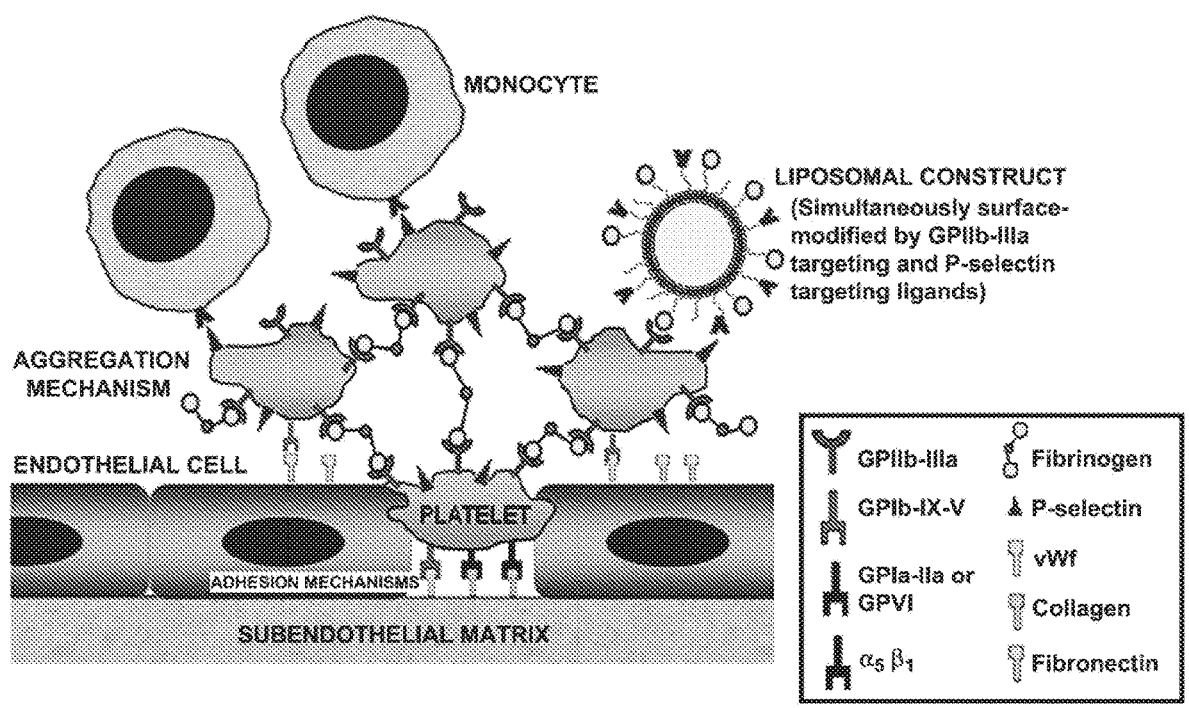
FIG. 1 is a schematic illustration showing the design of liposomal constructs surface-functionalized with two types of ligands for simultaneous targeting of GPIIb-IIIa integrin and P-selectin expressed at high quantity on the membrane surface of activated platelets involved in thrombotic and inflammatory events in vascular disease.

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent on the context in which it is used.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprines, equines, or canines felines, ayes, etc.).

The terms "diminishing," "reducing," or "preventing," "inhibiting," and variations of these terms, as used herein include any measurable decrease, including complete or substantially complete inhibition. The terms "enhance" or "enhanced" as used herein include any measurable increase or intensification.

As used herein, the term "small molecule" can refer to lipids, carbohydrates, polynucleotides, polypeptides, or any other organic or inorganic molecules.

As used herein, the term "polypeptide" refers to a polymer composed of amino acid residues related naturally occurring structural variants, and synthetic non-naturally occurring analogs thereof linked via peptide bonds or modified peptide bonds (i.e., peptide isosteres), related naturally occurring structural variants, and synthetic non-naturally occurring analogs thereof, glycosylated polypeptides, and all "mimetic" and "peptidomimetic" polypeptide forms. Synthetic polypeptides can be synthesized, for example, using an automated polypeptide synthesizer. The term can refer to an oligopeptide, peptide, polypeptide, or protein sequence, or to a fragment, portion, or subunit of any of these. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A "portion" of a polypeptide means at least about three sequential amino acid residues of the polypeptide. It is understood that a portion of a polypeptide may include every amino acid residue of the polypeptide.

"Mutants," "derivatives," and "variants" of a polypeptide (or of the DNA encoding the same) are polypeptides which may be modified or altered in one or more amino acids (or in one or more nucleotides) such that the peptide (or the nucleic acid) is not identical to the wild-type sequence, but has homology to the wild type polypeptide (or the nucleic acid).

A "mutation" of a polypeptide (or of the DNA encoding the same) is a modification or alteration of one or more amino acids (or in one or more nucleotides) such that the peptide (or nucleic acid) is not identical to the sequences recited herein, but has homology to the wild type polypeptide (or the nucleic acid).

As used herein, the term "imaging agent" can refer to a biological or chemical moiety capable of be encapsulated by a nanoparticle or microparticle construct of the application and that may be used to detect, image, and/or monitor the presence and/or progression of a cell cycle, cell function/physiology, condition, pathological disorder and/or disease.

As used herein, the terms "treating" or "treatment" of a disease can refer to executing a treatment protocol to increase blood flow by a measurable amount from a thrombosed value. Thus, "treating" or "treatment" does not require complete restoration of blood flow from a thrombosed value.

As used herein, the term "targeting moiety" can refer to a molecule or molecules that are able to bind to and complex with a biomarker. The term can also refer to a functional group that serves to target or direct a therapeutic agent to a particular location, cell type, diseased tissue, or association. In general, a "targeting moiety" can be directed against a biomarker.

An "effective amount" can refer to that amount of a therapeutic agent that results in amelioration of symptoms or a prolongation of survival in the subject and relieves, to some extent, one or more symptoms of the disease or returns to normal (either partially or completely) one or more physiological or biochemical parameters associated with or causative of the disease. "Therapeutic agents" can include any agent (e.g., molecule, drug, pharmaceutical composition, etc.) capable of be encapsulated by a nanoparticle or microparticle construct of the application and further capable of preventing, inhibiting, or arresting the symptoms and/or progression of a disease.

"Nanoparticle" or "microparticle" as used herein is meant to include particles, spheres, capsules, and other structures having a length or diameter of about 10 nm to about 100 μm. For the purposes of this application, the terms "nanosphere", "nanoparticle", "nanoparticle construct", "nanovehicle", "nanocapsule", "microsphere", "microparticle", and "microcapsule" are used interchangeably.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

This application relates to nanoparticles or microparticles and their use in binding activated platelets with sufficient strength so that they remain stably attached under the wall shear of hemodynamic flow as well as to compositions and methods useful in the delivery of therapeutic and/or imaging agents to activated platelets. The nanoparticle or microparticle compositions described herein, integrate multiple-ligand adhesion-promoting functionality on a single nanoparticle or microparticle. It was found that heteromultivalently ligand-modified nanoparticle or microparticle vehicles can simultaneously target integrins GPIIb-IIIa and P-selectin on thrombosis-associated active platelets, and can enhance selective binding to activated platelets at a clot site and stay retained even under hemodynamic flow.

It was further found that multi-receptor targeted strategy results in higher binding and retention of nanoparticles or microparticles on active platelets under flow conditions, compared to single receptor targeting at the same mol %. In addition, multi-receptor targeting by a single nanoparticle or microparticle composition allows for enhanced binding and retention with lower mol % of total ligands on the surface of a nanoparticle or microparticle, compared to single receptor targeting with only one type of ligand. Without being bound by theory it is believed that the enhanced effects of the heteromultivalently ligand-modified nanoparticle or microparticle vehicles is due to avidity effects of the dual receptor binding mechanisms. Therefore, the use of the heteromultivalent nanoparticle or microparticle compositions described herein can enhance the availability, safety and efficacy of vascular disease therapy.

The compositions described herein can be used in diagnostic, therapeutic, and/or theranostic applications to deliver therapeutic agents and/or imaging agents to activated platelets and/or nearby tissues in a subject as well as selectively target activated platelets and/or tissue of a subject upon systemic administration (e.g., intravenous, intravascular, intraarterial infusion) of the compositions to the subject. The compositions can also be remotely activated with a remote energy source to selectively release therapeutic agents and/or imaging agents to targeted activated platelets and/or nearby tissues of the subject.

In some embodiments, the compositions described herein can include a biocompatible, biodegradable nanoparticle or microparticle core construct and a plurality of at least two types of unique targeting moieties (e.g., a first and a second activated platelet targeting moiety), each selective for separate activated platelet receptor exposed on the platelet surface. The plurality of targeting moieties are bound to, conjugated to, and/or decorated on the surface defined by the nanoparticle or microparticle core. The first and second activated platelet targeting moieties can be spatially or topographically arranged on the nanoparticle or microparticle surface such that the first and second activated platelet targeting moieties do not spatially mask each other and the nanoparticle or microparticle is able to bind to an activated platelet with exposed activated platelet receptors, thereby enhancing retention of the nanoparticle or microparticle construct onto activated platelets under hemodynamic flow.

The nanoparticles or microparticles can be made from any biocompatible, biodegradable material that can form a nanoparticle or microparticle to which the activated platelet targeting moieties described herein can be attached, conjugated, and/or decorated. Examples of nanoparticles or microparticles can include liposomes, lipidic nanoparticles, a hydrogel, micelle, metal nanoparticles, polymer nanoparticles, dendrimer, quantum dots, and/or combinations of these materials which can include and/or be surface modified or engineered with the activated platelet targeting moieties. In some embodiments, the nanoparticles or microparticles can be optically or magnetically detectable. In other embodiments, intrinsically fluorescent or luminescent nanoparticles or microparticles, nanoparticles or microparticles that comprise fluorescent or luminescent moieties, plasmon resonant nanoparticles, and magnetic nanoparticles are among the detectable nanoparticles that can be used.

The nanoparticles or microparticles can have a maximum length or diameter of about 100 nm to about 10 μm In general, the nanoparticle or microparticle construct can have dimensions small enough to allow the composition to be systemically administered to a subject and targeted to activated platelets and tissue of the subject. In some embodiments, the nanoparticle or microparticle construct can have a size that facilitates encapsulation of one or more therapeutic and/or imaging agents.

The nanoparticles or microparticles of the composition may be uniform (e.g., being about the same size) or of variable size. Particles may be any shape (e.g., spherical or rod shaped), but are preferably made of regularly shaped material (e.g., spherical). Other geometries can include substantially spherical, circular, triangle, quasi-triangle, square, rectangular, hexagonal, oval, elliptical, rectangular with semi-circles or triangles and the like. Selection of suitable materials and geometries are known in the art.

In other embodiments, the nanoparticles or microparticles can include lipidic nanoparticles or microparticles, polymer nanoparticles or microparticles, liposomes, and/or dendrimers with a membrane, shell, or surface that is formed from a naturally-occurring, synthetic or semi-synthetic (i.e., modified natural) material. In some embodiments, the lipidic nanoparticles or liposomes can include a membrane or shell that is formed from a naturally-occurring, synthetic or semi-synthetic material that is generally amphipathic (i.e., including a hydrophilic component and a hydrophobic component). Examples of materials that can be used to form the membrane or shell of the lipidic nanoparticle or microparticle or liposome include lipids, such as fatty acids, neutral fats, phospholipids, oils, glycolipids, surfactants, aliphatic alcohols, waxes, terpenes and steroids. Semi-synthetic or modified natural lipids can include natural lipids that have been chemically modified in some fashion. The lipid can be neutrally-charged, negatively-charged (i.e., anionic), or positively-charged (i.e., cationic). Examples of anionic lipids can include phosphatidic acid, phosphatidyl glycerol, and fatty acid esters thereof, amides of phosphatidyl ethanolamine, such as anandamides and methanandamides, phosphatidyl serine, phosphatidyl inositol and fatty acid esters thereof, cardiolipin, phosphatidyl ethylene glycol, acidic lysolipids, sulfolipids and sulfatides, free fatty acids, both saturated and unsaturated, and negatively-charged derivatives thereof. Examples of cationic lipids can include N-[1-(2,3-dioleoyloxy)propyl]-N,N,N-trimethyl-ammonium chloride and common natural lipids derivatized to contain one or more basic functional groups.

Other examples of lipids, any one or combination of which may be used to form the membrane or shell of the lipidic nano-particle or liposome, can include: phosphocholines, such as 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine, dimyristoylphosphatidylcholine, dipentadecanoylphosphatidylcholine, dilauroylphosphatidylcholine, dipalmitoylphosphatidylcholine (DPPC), distearoylphosphatidylcholine (DSPC), and diarachidonylphosphatidylcholine (DAPC); phosphatidylethanolamines, such as dioleoylphosphatidylethanolamine, dipalmitoylphosphatidylethanolamine (DPPE), and distearoylphosphatidylethanolamine (DSPE); phosphatidylserine; phosphatidylglycerols, including distearoylphosphatidylglycerol (DSPG); phosphatidylinositol; sphingolipids, such as sphingomyelin; glycolipids, such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG); lipids bearing sulfonated mono-, di-, oligo- or polysaccharides; cholesterol, cholesterol sulfate, and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylaamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes, such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as, for example, the class of compounds referred to as TWEEN (commercially available from ICI Americas, Inc., Wilmington, Del.), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl)carbonyl)methylamino)octadecanoic acid; N-[12-(((7'-diethylaminocoumarin-3-yl)carbonyl)methylamino)octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoyl-glycerophosphoethanolamine and palmitoylhomocysteine; and/or any combinations thereof.

Examples of biocompatible, biodegradable polymers that can be used to form the nanoparticles are poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and poly(lactide)s or poly(lactide-co-glycolide)s, biodegradable polyurethanes, and blends and/or copolymers thereof.

Other examples of materials that may be used to form the nanoparticles or microparticles can include chitosan, poly (ethylene oxide), poly(lactic acid), poly(acrylic acid), poly (vinyl alcohol), poly(urethane), poly(N-isopropyl acrylamide), poly(vinyl pyrrolidone) (PVP), poly(methacrylic acid), poly(p-styrene carboxylic acid), poly(p-styrenesulfonic acid), poly(vinylsulfonicacid), poly(ethyleneimine), poly (vinylamine), poly(anhydride), poly(L-lysine), poly(L-glutamic acid), poly(gamma-glutamic acid), poly(carprolactone), polylactide, poly(ethylene), poly(propylene), poly (glycolide), poly(lactide-co-glycolide), poly(amide), poly (hydroxylacid), poly(sulfone), poly(amine), poly (saccharide), poly(HEMA), poly(anhydride), gelatin, glycosaminoglycans (GAG), poly(hyaluronic acid), poly (sodium alginate), alginate, albumin, hyaluronan, agarose, polyhydroxybutyrate (PHB), copolymers thereof, and blends thereof.

In some embodiments, the nanoparticle or microparticle can include a liposome. The liposome can be an unilamellar liposome. The liposome can have a width less than about 200 nm. For example, the width of the liposome can be about 100 nm to about 150 nm. In some embodiments, the liposome is about 150 nm in diameter. The liposome can have a high cholesterol content (e.g., about 40%) in the membrane in order to efficiently encapsulate a water-soluble thrombolytic drug protecting the drug from plasma deactivation in circulation and prevent premature drug leakage due to membrane rigidity.

In an embodiment of the application, liposome nanoparticles having a diameter of 150 nm can be prepared by homogenizing DSPC (49 mol %), and DSPE-PEG-peptide (5 mol %), cholesterol (45 mol %) in 1:1 chloroform: methanol and subjecting the mixture to reverse phase evaporation through several cycles of freeze-thaw, followed by extrusion through a 200 nm polycarbonate membrane to achieve unilamellar vesicles. The particles can then be surface-modified with the targeting moieties at a surface density and at a ratio of first activated targeting moiety to second activated targeting moiety effective to promote maximum particle adhesion to exposed activated platelet surfaces and retention at low-to-high sheer stresses.

In some embodiments, the nanoparticles can include quantum dots, i.e., bright, fluorescent nanocrystals with physical dimensions small enough such that the effect of quantum confinement gives rise to unique optical and electronic properties. In certain embodiments, the nanoparticles are optically detectable nanoparticles, such as metal nanoparticles. Metals used to form the nanoparticles include, but not limited to, Ag, Au, Cu, Al, Fe, Co, Ni, Ru, Rh, Pd, and Pt or oxides thereof. In another embodiment, the metal comprises Fe or iron oxide. A further surface functional layer can be added or formed in combination with a metal core material. Such functional layers can include, but are not limited to, Ag oxide, Au oxide, $SiO_2$, $Al_2O_3$, $Si_3N_4$, $Ta_2O_5$, $TiO_2$, ZnO, $ZrO_2$, $HfO_2$, $Y_2O_3$, tin oxide, antimony oxide, iron oxide, and other oxides; Ag doped with chlorine or chloride, Au doped chlorine or chloride, Ethylene and Chlorotrifluoroethylene (ECTFE), Poly(ethylene-co-butyl acrylate-co-carbon monoxide) (PEBA), Poly(allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), Polyvinylprorolidone (PVP), and other polymers; stacked multiple layers at least two layers including above listed metal layers and non-metal layers, and the like. In some embodiments, the metal core can be Au, Ag, Fe, Ti, Ni, Cr, Pt, Ru, NiCr alloy, NiCrN, PtRh alloy, CuAuCo alloy, IrRh alloy and/or WRe alloy. The metals used should be biocompatible.

In some embodiments, the nanoparticle or microparticle can be a magnetic nanoparticle or microparticle. "Magnetic particles" refers to magnetically responsive particles that contain one or more metals or oxides or hydroxides thereof. Compositions including optically detectable metal nanoparticles or quantum dots can be detected in vivo upon systemic administration to a subject using magnetic resonance imaging (MRI), magnetic resonance spectroscopy (MRS), nuclear magnetic resonance imaging (NMR), multimodal imaging, fluorescent, positron emission tomography (PET), near infrared (NIR) imaging, X-ray imaging, and computed tomography (CT).

The composition of the application includes a first and a second activated platelet targeting moiety, each capable of targeting and/or adhering the nanoparticle or microparticle to an activated platelet via a unique activated platelet surface biomarker. The targeting moieties can comprise any molecule, or complex of molecules, which is/are capable of interacting with an exposed activated platelet surface biomarker. The biomarker can include, for example, a cellular protease, a kinase, a protein, a cell surface receptor, a lipid, and/or fatty acid. The targeting moieties can interact with the biomarkers through, for example, non-covalent binding, covalent binding, hydrogen binding, van der Waals forces, ionic bonds, hydrophobic interactions, electrostatic interaction, and/or combinations thereof.

The targeting moieties can include, but are not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In some embodiments, the targeting moiety may comprise a peptide ligand molecule, including, for example, ligands which naturally recognize a specific desired receptor of an activated platelet, such as a fibrinogen ligand specific for GPIIb-IIIa or a P-selectin glycoprotein ligand-1 specific for p-selectin. Natural ligands binding to these two receptors are responsible for stabilizing active platelet interactions at vascular disease sites under a hemodynamic shear environment. Such ligand molecules for use in a composition of the application include ligands that have been modified to increase their specificity of interaction with a target receptor, ligands that have been modified to interact with a desired receptor not naturally recognized by the ligand, and fragments of such ligands. Peptide ligands can also include small protein-like chains designed to mimic a peptide ligand (peptidomimetics). In some embodiments, the targeting moiety can include a small molecule peptide ligand. Preparation of peptide ligands can be accomplished by any number of methods for generating peptides.

Advantageously, peptide targeting moieties can each include about 5 to about 30 amino acids. By limiting the size of the peptides to about 5 to about 30 amino acids, the first and second activated platelet targeting moieties can be spatially or topographically arranged on the nanoparticle or microparticle surface such that the first and second platelet targeting moieties do not spatially mask each other and are able to adhere to an activated platelet surface with exposed surface receptors and enhance adhesion and retention of the nanoparticle or microparticle to the activated platelet surface at low-to-high sheer stresses.

In some embodiments, the first or second targeting moiety can be a targeting peptide comprising glycoprotein ligands having specificity to P-selectin. In some embodiments, the first or second targeting moiety can be a p-selectin targeting peptide comprising an amino acid sequence of EWVDV (SEQ ID NO:1). In some embodiments, the first or second targeting moiety can be a p-selectin targeting peptide comprising an amino acid sequence of CDVEWVDVS (SEQ ID NO:4). In some embodiments, the first or second targeting moiety can be a p-selectin targeting peptide comprising an amino acid sequence of DAEWVDVS (SEQ ID NO:5). The peptide may be synthesized by any method known in the art. For example, the p-selectin targeting peptide may be synthesized using Fmoc based solid phase chemistry and characterized using MALDI-TOF mass spectroscopy.

In some embodiments, the first or second targeting moiety can be a targeting peptide comprising a tripeptide RGD (arginine-glycine-aspartic acid) amino acid sequence motif having a high selective affinity to GPIIb-IIIa. GPIIb-IIIa is an integrin upregulated and stimulated into a ligand-binding conformation on the surface of activated platelets. The RGD motif containing targeting peptide may contain a single repeat of the RGD motif or may contain multiple repeats of the RGD motif, such as, for example, 2, or 5, or 10 or more repeats of the RGD motif. One of skill in the art will understand that conservative substitutions of particular amino acid residues of the RGD motif containing targeting peptide may be used so long as the RGD motif containing targeting peptide retains the ability to bind comparably as the native RGD motif. One of skill in the art will also understand that conservative substitutions of particular amino acid residues flanking the RGD motif so long as the RGD motif containing targeting peptide retains the ability to bind comparably as the native RGD motif. A RGD peptide containing targeting moiety can be synthesized using FMoc-based solid phase chemistry on resin, and characterized using mass spectroscopy.

An RGD peptide having high selective affinity to GPIIb-IIIa can include a linear-RGD peptide or a cyclic RGD peptide. Preferred RGD peptides do not bind or activate quiescent platelets nor interact with other RGD-binding integrins. In some embodiments, the targeting moiety can include a linear RGD (lRGD) peptide having the amino acid sequence of (SEQ ID NO:2). In some embodiments, a first of second targeting moiety can include a cyclic RGD (abbreviated cRGD) peptide having the amino acid sequence of cyclo-CNPRGDY(-OEt)RC (SEQ ID NO: 3). For cRGD synthesis, the terminal cysteine residues of the linear precursor can be cyclized by a disulfide bond using an ferricyanide-mediated oxidation process.

The targeting moiety can be coupled to nanoparticles or microparticles of the composition using a linker. The linker can be of any suitable length and contain any suitable number of atoms and/or subunits. The linker can include one or a combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof.

The first and second activated platelet targeting moieties can be tethered to the surface of the nanoparticle or microparticle construct. In some embodiments, the first and second activated platelet targeting moieties can be tethered to the surface of the nanoparticle or microparticle construct via a polymer tether. The polymer tether can be linked to the nanoparticle or microparticle construct directly or indirectly by any means. For example, the polymer tether can be linked to the nanoparticle or microparticle construct using a covalent link, a non-covalent link, an ionic link, and a chelated link, as well as being absorbed or adsorbed onto the nanoparticle or microparticle construct. In addition, the polymer tether can be linked to the nanoparticle or microparticle construct through hydrophobic interactions, hydrophilic interactions, charge-charge interactions, π-stacking interactions, combinations thereof, and like interactions.

In some embodiments, the targeting moieties are conjugated to the surface of the nanoparticle or microparticle via a PEG molecule linker. The PEG molecules can have a variety of lengths and molecular weights, including, for example, PEG 200, PEG 1000, PEG 1500, PEG 4600, PEG 10,000, or combinations thereof. In other embodiments, the targeting moieties can be conjugated to the nanoparticle or microparticle surface with PEG acrylate, or PEG diacrylate, molecules of a variety of molecular weights. Active platelet-targeting moieties can be conjugated on the liposome surface, to promote specific binding and retention of the liposomes on thrombus-associated active platelets. For example, integrin GPIIb-IIIa and P-selectin targeting small molecular weight peptide targeting moieties can be conjugated on the surface of a liposome via a PEG spacer.

Figure 2:
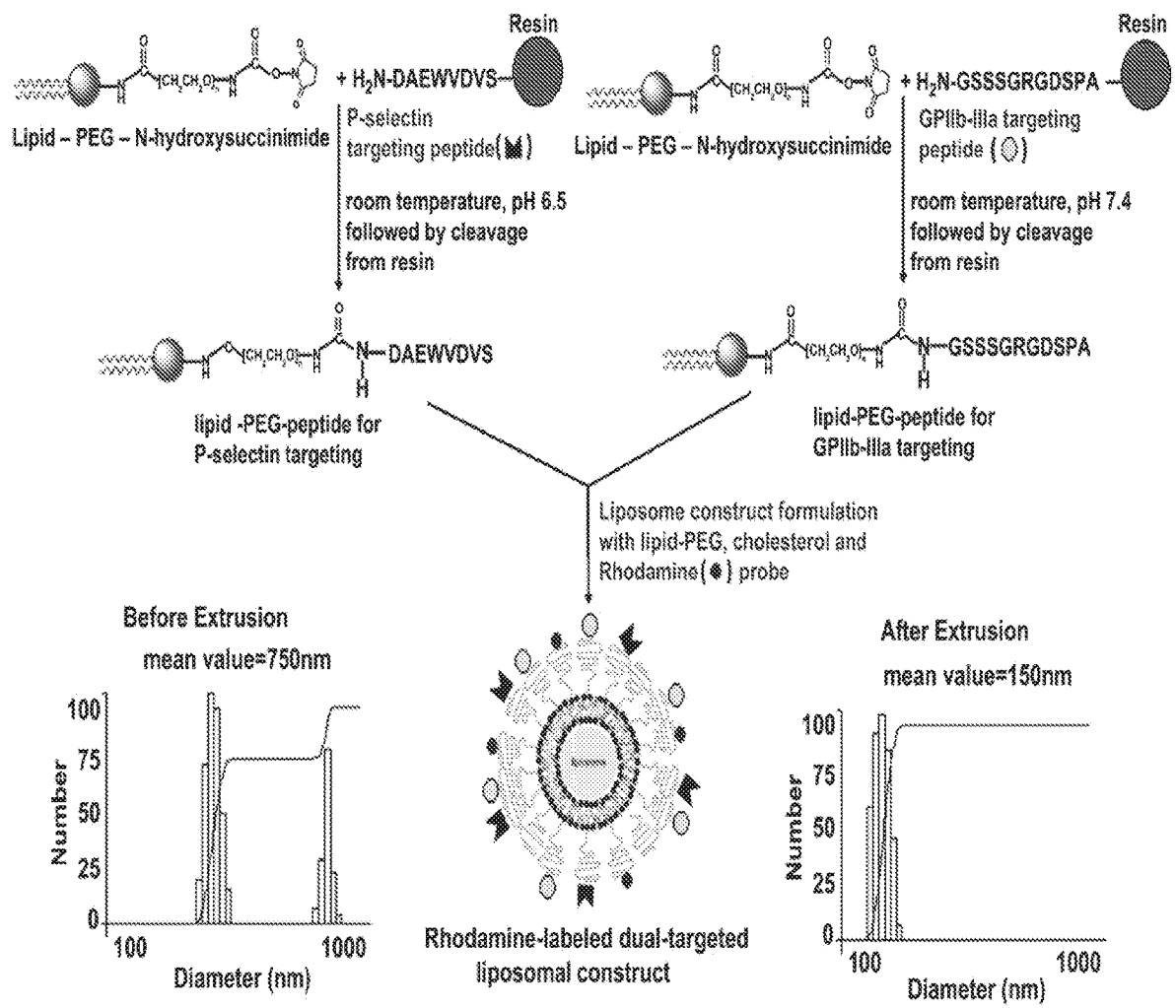
FIG. 2 illustrates a process for fabricating the heteromultivalent liposomal constructs for dual targeting of activated platelets by RGD peptide (SEQ ID NO: 2) and DAEWVDVS (SEQ ID NO:5); bottom panel shows representative DLS characterization data for the constructs before and after extrusion; after extrusion the constructs are largely monodisperse with an average diameter of 150 nm.

Targeting peptides can be conjugated 'on resin' to NHS-ester modified-lipid (DSPE-PEG-NHS ester) by reductive amidation to form DSPE-PEG-peptide (see FIG. 2). The PEG-peptide conjugates or PEGylated peptides can then be conjugated to the nanoparticle or microparticle using known conjugation techniques.

The ratio of the first targeting moiety to the second targeting moiety provided on the nanoparticle or microparticle surface can be about 80:20 to about 20:80 and be adjusted accordingly to maximize adhesion under low-to-high shear conditions. It will be appreciated, that other ratios can be used to enhance the nanoparticle or microparticle adherence and retention to activated platelets. In addition, the total mol % of targeting moieties used for particle surface-modification can be varied to enhance binding and retention to activated platelets under flow.

In other embodiments, the composition can further include imaging agents (or detectable moieties) and/or therapeutic agents that are encapsulated by (e.g., within liposome, lipidic nanoparticle or microparticle, or polymer nanoparticle or microparticle), contained in (e.g., polymer nanoparticles or dendrimers), or conjugated to the nanoparticles.

Imaging agents can include any substance that may be used for imaging or detecting a region of interest (ROI) in a subject and/or diagnosing the presence or absence of a disease or diseased tissue in a subject. The imaging agent can be selected such that it generates a signal, which can be measured and whose intensity is related (preferably proportional) to the distribution of the imaging agent and activated platelets in the subject. Examples of imaging agents include, but are not limited to: radionuclides, fluorescent dyes, chemiluminescent agents, colorimetric labels, and magnetic labels. In one example, the imaging agent can include a radiolabel that is detected using gamma imaging wherein emitted gamma irradiation of the appropriate wavelength is detected. Methods of gamma imaging include, but are not limited to, SPECT and PET. For SPECT detection, the chosen radiolabel can lack a particular emission, but will produce a large number of photons in, for example, a 140-200 keV range. For PET detection, the radiolabel can be a positron-emitting moiety, such as 19F.

In another example, the imaging agent can include an MRS/MRI radiolabel, such as gadolinium, 19F, 13C, that is coupled (e.g., attached or complexed) with the composition using general organic chemistry techniques. The imaging agent can also include radiolabels, such as 18F, 11C, 75Br, or 76Br for PET by techniques well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, NY 1986) the contents of which are hereby incorporated by reference. The imaging can also include 123I for SPECT.

The imaging agent can further include known metal radiolabels, such as Technetium-99m (99mTc). Preparing radiolabeled derivatives of Tc99m is well known in the art. See, for example, Zhuang et al., "Neutral and stereospecific Tc-99m complexes: [99mTc]N-benzyl-3,4-di-(N-2-mercaptoethyl)-amino-pyrrolidines (P-BAT)" Nuclear Medicine & Biology 26(2):217-24, (1999); Oya et al., "Small and neutral Tc(v)O BAT, bisaminoethanethiol (N2S2) complexes for developing new brain imaging agents" Nuclear Medicine & Biology 25(2):135-40, (1998); and Hom et al., "Technetium-99m-labeled receptor-specific small-molecule radiopharmaceuticals: recent developments and encouraging results" Nuclear Medicine & Biology 24(6):485-98, (1997).

Therapeutic agents or bioactive agents, encapsulated by, contained in, and/or linked to nanoparticles or microparticles of the present application can include any substance capable of exerting a biological or therapeutic effect in vitro and/or in vivo. Therapeutic agents can also include any therapeutic or prophylactic agent used in the treatment (including the prevention, diagnosis, alleviation, or cure) of a malady, affliction, condition, disease or injury in a subject. Examples of therapeutic agents include, but are not limited to thrombolytic, anti-thrombosis, and anti-proliferative agents. The therapeutic agents can be in the form of biologically active ligands, small molecules, peptides, polypeptides, proteins, DNA fragments, DNA plasmids, interfering RNA molecules, such as siRNAs, oligonucleotides, and DNA encoding for shRNA.

In some embodiments, the therapeutic agent can be a thrombolytic agent that is encapsulated by, contained in, and/or linked to the nanoparticles or microparticles. Thrombolytic agents are used to dissolve blood clots in a procedure termed thrombolysis and can limit the damage caused by the blockage or occlusion of a blood vessel. Thrombolytic agents can include analogs of tissue plasminogen activator (tPA), the protein that normally activates plasmin and recombinant tissue plasminogen activators (r-tPAs) include alteplase, reteplase, and tenecteplase (sold under the trade name TNKase) and desmoteplase. Additional thrombolytic agents include anistreplase (sold under the trade name EMINASE), streptokinase (sold under the trade names KABIKINASE, STREPTASE), and urokinase (sold under the trade name ABBOKINASE).

In some embodiments, the therapeutic agent can be an anti-thrombotic agent that is encapsulated by, contained in, and/or linked to the nanoparticles or microparticles. Anti-thrombotic agents can include anticoagulants and antiplatelet agents.

Anticoagulants slow down clotting, thereby reducing fibrin formation and preventing clots from forming and growing. Anticoagulants include coumarins (vitamin K antagonists) such as coumadin. Anticoagulants also include but are not limited to heparin, heparin derivatives and direct thrombin inhibitors including the bivalent drugs hirudin, lepirudin, and bivalirudin and the monovalent drugs argatroban and dabigatran.

Antiplatelet agents prevent platelets from clumping and also prevent clots from forming and growing. Antiplatelet agents can include but are not limited to aspirin and clopidogrel (sold under the trade name PLAVIX).

In some embodiments, the therapeutic and/or imaging agents can be loaded into and/or onto the nanoparticles or microparticles by encapsulation, absorption, adsorption, and/or non-covalent linkage of the agent to or within the nanoparticle or microparticle. The amount of agent loaded onto or in the nanoparticle or microparticle can be controlled by changing the size of the nanoparticle or microparticle or the composition of the nanoparticle or microparticle.

In some embodiments, release of the therapeutic or imaging agent from the nanoparticle or microparticle of the composition can occur by desorption, diffusion through the polymer or lipid coating, or polymer or lipid wall, nanoparticle or microparticle erosion, and/or disruption of the nanoparticle or microparticle structure, which can all be controlled by the type of the nanoparticle or microparticle, i.e., having it become swollen or degradable in the chosen microenvironment.

In some embodiments, the therapeutic or imaging agent can be released from the nanoparticle or microparticle composition through the use of an internal and/or external trigger. Internal triggers include the body's internal pH, chemical and enzymatic activity. External triggers can include light and ultrasound.

Advantageously, a nanoparticle or microparticle construct that allows remote release of the therapeutic agent, (e.g., a thrombolytic agent, such as tPA) can target or be targeted to activated platelets of a thrombus associated with a vascular disease site, by systemic administration (e.g., intravenous, intravascular, or intraarterial infusion) to the subject and once targeted to the site remotely released to specifically treat the targeted activated platelets or disease site tissue of the subject (e.g., activated platelets of a thrombus associated with a vascular disease site). Targeting and selective release of the thrombolytic agents and/or anti-thrombotic agents to activated platelets and the surrounding cells and tissue allows treatment of such vascular disease using thrombolytic agents and/or anti-thrombotic agents, which would provide an otherwise diminished therapeutic effect if not targeted and remotely released using the compositions described herein.

In some embodiments, release of the therapeutic agent and/or imaging agent from the nanoparticle or microparticle of the composition can be triggered by an energy source that supplies energy to the composition effective to release the therapeutic agent or imaging agent from the nanoparticle or microparticle construct. The energy source can be external or remote from a subject, which allows non-invasive remote release of the therapeutic agent to the subject. The remote energy source can be, for example, a minimally invasive laser that can be inserted in vivo in the subject being treated or positioned external or ex vivo the subject. The energy from laser can be in the near infrared range to allow deep radiation penetration into tissue and remote release of therapeutic agent or imaging agent.

Therefore, in some embodiments, a nanoparticle or microparticle construct of the composition can be surface modified to be responsive to energy, from a remote source that is effective to release the therapeutic agent from the nanoparticle or microparticle upon mechanical disruption of the nanoparticle or microparticle membrane or shell after administering the composition to a subject.

In an exemplary embodiment, near infra-red (NIR)-responsive gold nanorods (GNRs) conjugated close to the surface of the heteromultivalent nanoparticles encapsulating or containing a therapeutic agent can exhibit plasmon resonance phenomena under tissue-penetrating NIR light, such that the resultant thermo-mechanical energy dissipation results in disruption of the nanoparticle or microparticle to render site-selective rapid drug release. Thus, in some embodiments, NIR-irradiation from specialized external or catheter-mediated laser devices can be used to remotely trigger rapid drug release at the targeted disease site via photothermal destabilization of GNR-modified nanoparticles.

Upon administration of the composition to a subject by, for example, intravascular administration, the composition can target an activated platelet at a vascular disease site being treated. In some embodiments, the composition can be imaged by, for example, magnetic resonance imaging or computed tomography, to confirm localization and targeting of the composition to the occlusive vascular disease site. The composition targeted to the vascular disease site can be applied NIR from a remote NIR energy source that is external to the subject being treated to mechanically resonate or oscillate the GNRs on the nanoparticle or microparticle and rapidly release the therapeutic agent from the liposome membrane or shell due to defects in the membrane or shell caused by oscillation of the gold linked to the nanoparticle or microparticle.

GNRs of certain dimensions exhibit plasmon resonance in the NIR wavelength range (700-900 nm), resulting in generation of heat. GNRs of a NIR-responsive aspect ratio can be synthesized relatively consistently via kinetic controls. NIR-responsive GNR can be fabricated as shown in the Examples below using a seed-mediated method. Exemplary NIR-responsive GNRs are about 50 nm long with an aspect ratio of about 2-5 that have plasmon resonance in the NIR range.

In some embodiments, the mild NIR energy applied to the nanoparticle or microparticle of the composition can be that amount effective cause the GNRs on the nanoparticles to mechanically resonate or oscillate at an amount or level effective to disrupt the nanoparticle or microparticle membrane or shell and release the therapeutic agent without causing significant heating (e.g., greater than 1° C., 2° C., 3° C., or 5° C.) around the nanoparticle or microparticle when administered to a subject.

In an exemplary embodiment, GNR-decorated ligand modified platelet-targeted thrombolytic-loaded liposomes can be exposed to a 800 nm laser diode driven at ~1 W power and at frequencies of 0.5, 5, 20, 100, 200 and 500 kHZ to provide pulse widths of 200, 20, 5, 1, 0.5 and 0.2 µs. The NIR irradiation exposure durations can be maintained at about 10 sec to about 10 min for the various pulse widths. In some embodiments the NIR irradiation exposure durations can be maintained at about 30 sec to about 5 min.

NIR-responsive GNRs can be fabricated and conjugated close to the nanoparticle or microparticle (e.g., liposome) surface using lipoic acid linkers, to allow NIR-induced photothermal disruption of the nanoparticle or microparticle for payload release. In some embodiments, the nanoparticles will have the GNRs conjugated close to their surface via the lipoic acid linkers and the platelet-targeting peptides conjugated above the surface via PEG linkers.

Figure 13:
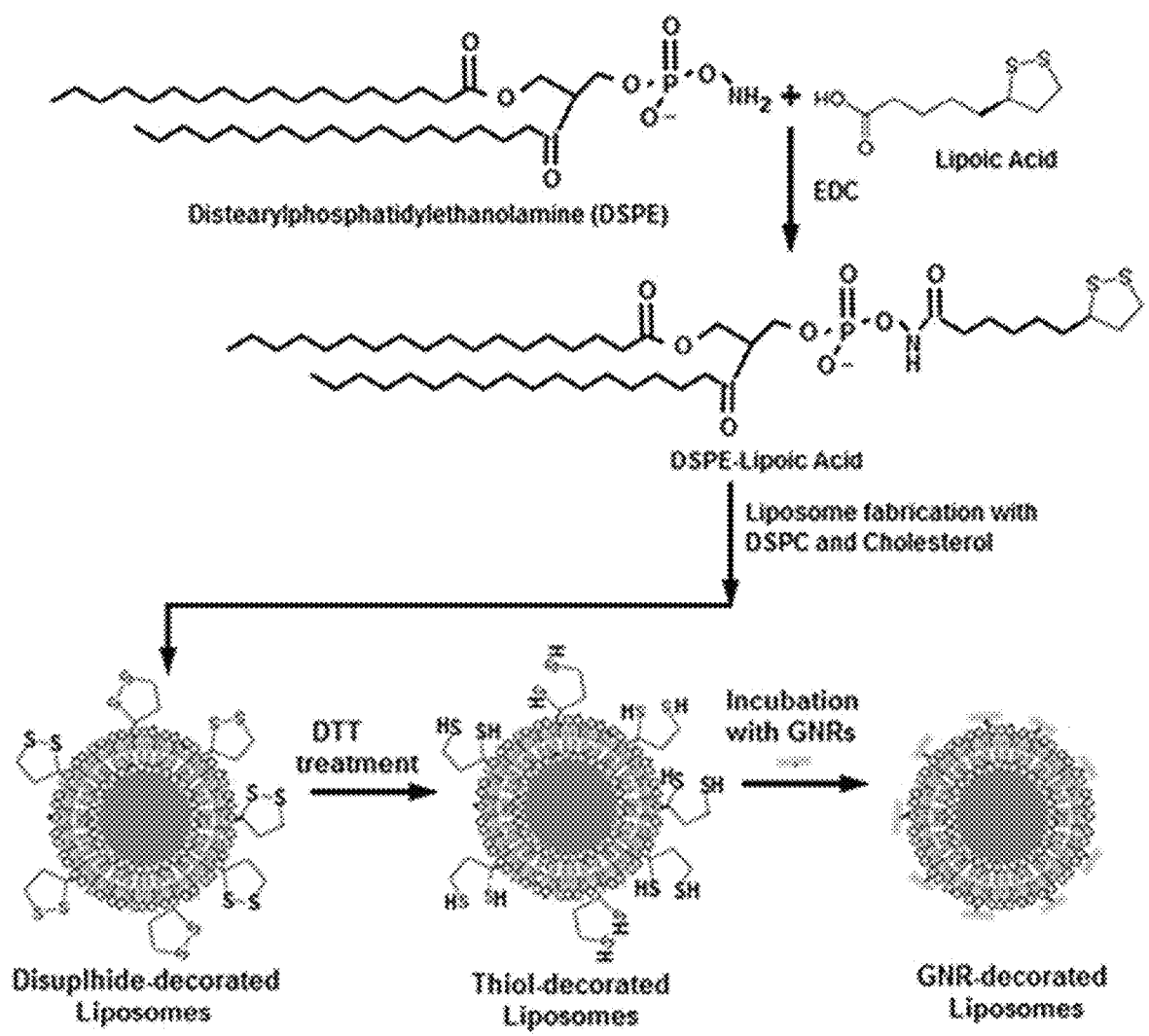
FIG. 13 illustrates a schematic representation of the fabrication of GNR-decorated liposomes in accordance with an embodiment of the application.
Figure 14:
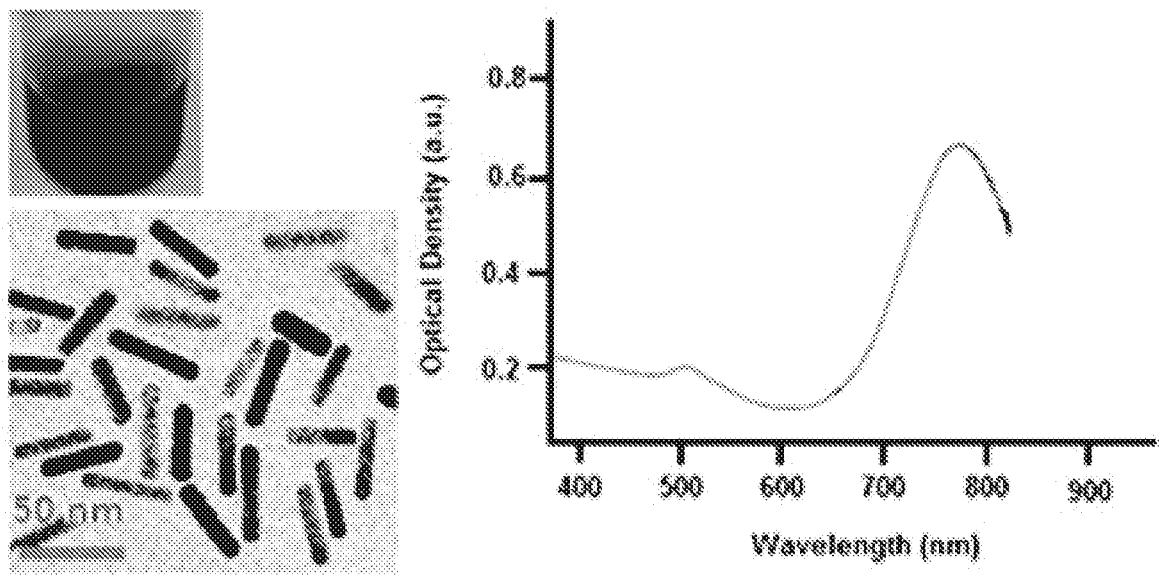
FIG. 14 shows a representative TEM and absorption spectra for GNRs fabricated using the seed-mediated method.
Figure 15:
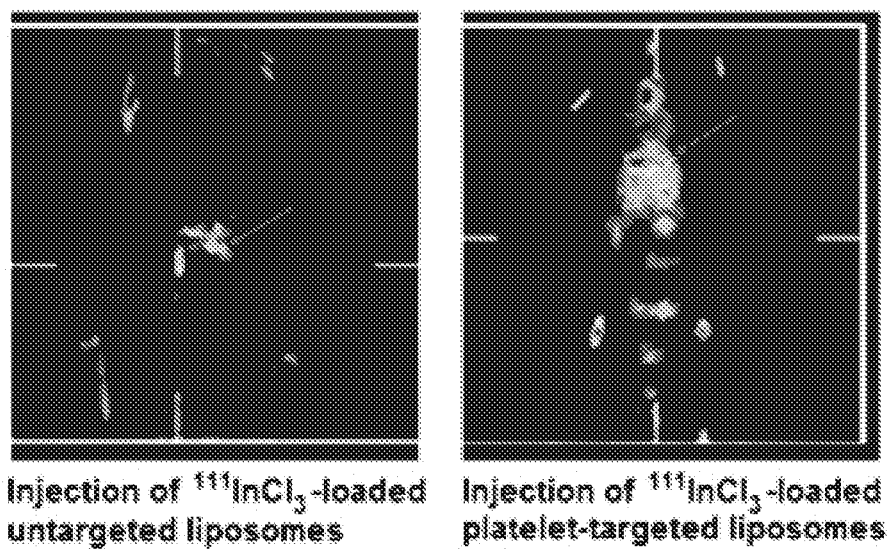
FIG. 15 illustrates Single Photon Emission Computed Tomography (ASPECT) images confirming enhanced thrombus-selective accumulation of platelet-targeted liposomes in carotid injury.

GNR-modified liposomes can be produced, for example, by formulating together DSPE-lipoic acid, DSPE-PEG-cRGD and DSPE-PEG-EWVDV along with 40 mol % cholesterol and remaining mol % of DSPC. The liposome surface lipoic acid motifs can then be treated with DTT to generate thiols and then decorated with the GNRs (see FIG. 13). GNR decoration density can be optimized for favorable NIR-induced payload release kinetics.

Preferably, the GNR surface decoration parameters (corresponding to DSPE-lipoic acid mole %) on liposomes and the NIR-irradiation parameters are the parameters that result in at least 80% release of encapsulated payload upon NIR-exposure for short durations. The power, pulse widths and frequencies are those safe for the intended in vivo applications.

It will be appreciated that other remote energy sources can be used to release the therapeutic agent or imaging agent from the nanoparticle or microparticle and that the selection of the energy source will depend at least in part on the nanoparticle or microparticle construct used to form the composition.

In some embodiments, the compositions comprising a multi-ligand modified nanoparticle or microparticle described herein, can be formulated in a pharmaceutical composition and administered to an animal, preferably a human, to facilitate the delivery of a therapeutic agent.

Formulation of pharmaceutical composition for use in the modes of administration noted below (and others) are described, for example, in *Remington's Pharmaceutical Sciences* (18$^{th}$ edition), ed. A. Gennaro, 1990, Mack Publishing Company, Easton, Pa.

Such a pharmaceutical composition may consist of a plurality of surface modified heteromultivalent nanoparticle or microparticle alone, in a form suitable for administration to a subject, or the pharmaceutical composition may comprise a plurality of nanoparticles and one or more pharmaceutically acceptable carriers, one or more additional ingredients, one or more pharmaceutically acceptable therapeutic agents, bioactive agents, imaging/diagnostic agents, or some combination of these. In some embodiments, the therapeutic agent may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the therapeutic agent may be combined and which, following the combination, can be used to administer the therapeutic agent to a subject. As used herein, the term "physiologically acceptable" ester or salt means an ester or salt form of the therapeutic agent which is compatible with any other ingredients of the pharmaceutical composition, which is not deleterious to the subject to which the composition is to be administered.

For example, pharmaceutical compositions can be in the form of a sterile aqueous or oily injectable solution containing, if desired, additional ingredients, for example, preservatives, buffers, tonicity agents, antioxidants, stabilizers, nonionic wetting or clarifying agents, and viscosity increasing agents. This suspension or solution may be formulated according to the known art, and may comprise, in addition to the therapeutic agent, additional ingredients such as the dispersing agents, wetting agents, or suspending agents described herein. Such sterile injectable formulations may be prepared using a non-toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials.

In some embodiments, a bioactive agent, imaging/diagnostic agent, and/or therapeutic agent can be conjugated, encapsulated, and/or contained with the heteromultivalent nanoparticle or microparticle so that the heteromultivalent nanoparticle or microparticle acts as a delivery vehicle. In other embodiments, the bioactive agent, imaging/diagnostic agent, and/or therapeutic agent can be merely contained in a pharmaceutical composition either with or without the modified nanoparticles and administered to concurrently with or separately from administration of the nanoparticles. Selection of a bioactive agent, imaging/diagnostic agent, and/or therapeutic agent to be conjugated to or encapsulated within the heteromultivalent nanoparticle or microparticle is dependent upon the use of the nanoparticle or microparticle and/or the condition being treated and the site and route of administration.

In some embodiments, a composition described herein can be used in a method for treating a vascular disease in a subject. In some embodiments, the disease can be characterized, in part, by the presence of activated platelets and/or platelet aggregation at a disease site (e.g., a thrombosed site). In some embodiments, a therapeutically effective amount of the composition can be administered in vivo to a subject to treat the subject. In some embodiments, an effective amount of the composition is the amount required to restore blood flow by about 50% from its thrombosed value. Post-irradiated blood flow can be monitored for example sonographically.

It should be understood, that the methods of treatment by the delivery of a composition including a heteromultivalent nanoparticle or microparticle includes the treatment of subjects that are already afflicted with a vascular disease or symptoms thereof (e.g., a blood clot), as well as prophylactic treatment uses in subjects not yet afflicted and/or experiencing symptoms. In a preferred embodiment the subject is an animal. In a more preferred embodiment the subject is a human.

Although the descriptions of pharmaceutical compositions provided herein are principally directed to pharmaceutical compositions which are suitable for ethical administration to humans, it will be understood by the skilled artisan that such compositions are generally for administration to animals of all sorts. Modification of pharmaceutical compositions for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, animals including commercially relevant animals such as cattle, pigs, horses, sheep, cats, and dogs, birds including commercially relevant birds such as chickens, ducks, geese, and turkeys.

Pharmaceutical compositions that are useful in the methods described herein may be administered by any convenient route, such as by infusion or bolus injection. For example, the composition may be introduced into the subject by any suitable route, including intraventricular injection or intraventricular injection via an intraventricular catheter that is attached to a reservoir.

The composition can be delivered systematically (e.g., intravenously), regionally, or locally by, for example, intraarterial, intrathrombal, intravenous, parenteral, intraneural cavity, topical, oral or local administration, as well as subcutaneous, intra-tracheal (e.g., by aerosol), or transmucosal (e.g., buccal, bladder, vaginal, uterine, rectal, nasal, mucosal). If delivery of the composition to the brain is desired, the targeted composition can be injected into an artery of the carotid system of arteries (e.g., occipital artery, auricular artery, temporal artery, cerebral artery, maxillary artery etc.). As discussed above, the composition can be formulated as a pharmaceutical composition for in vivo administration.

The pharmaceutical compositions described herein may also be formulated so as to provide slow, prolonged or controlled release. In general, a controlled-release preparation is a pharmaceutical composition capable of releasing the heteromultivalent nanoparticles at a desired or required rate to maintain constant activity for a desired or required period of time.

The relative amounts of the ingredients in a pharmaceutical composition of the invention will vary, depending upon the identity, size, and condition of the subject treated and further depending upon the route by which the composition is to be administered. By way of a non-limiting example, the composition may comprise between 0.1% and 100% (w/w) of the heteromultivalent nanoparticles.

The composition including heteromultivalent nanoparticles can be administered to the subject at an amount effective to provide a desired result(s) and to avoid undesirable physiological results. In some embodiments, the synthetic platelet compositions described herein may be administered to deliver a dose of between 1 ng/kg/day and 100 mg/kg/day. In one embodiment, a dose can be administered that results in a concentration of the synthetic platelets between 1 µM and 10 µM in a mammal. The precise dose to be employed can also depend on the route of administration, and should be decided according to the judgment of a medical practitioner and each subject's circumstances. In addition, known in vitro and in vivo assays may optionally be employed to help identify optimal dosage ranges. Effective doses may be extrapolated from dose-response curves derived from in vitro or in vivo test systems. Preferably, the dosage of the heteromultivalent nanoparticles will vary from about 1 µg to about 50 mg per kilogram of body weight of the animal. More preferably, the dosage will vary from about 10 µg to about 15 mg per kilogram of body weight of the animal. Even more preferably, the dosage will vary from about 100 µg to about 10 mg per kilogram of weight of the animal.

The composition can be administered in a variety of unit dosage forms, depending upon the particular disease or disorder being treated, the general medical condition of each subject, the method of administration, and the like. Details on dosages are well described in the scientific literature. The exact amount and concentration of the targeted compositions, or the "effective dose", can be routinely determined (e.g., by a medical practitioner).

The pharmaceutical composition may be administered to a subject as needed. The pharmaceutical composition may be administered to a subject as frequently as several times daily, or it may be administered less frequently, such as once a day, once a week, once every two weeks, once a month, or even less frequently, such as once every several months or even once a year or less. The "dosing regimen" will depend upon a variety of factors, such as the type and severity of the disease being treated, the general state of the subject's health, the subject's age, and the like. Using guidelines describing alternative dosing regimens, e.g., from the use of other agents and compositions, the skilled artisan can readily determine by routine trials the optimal effective concentrations of the composition.

In some embodiments, the composition described herein can be used with in vivo imaging methods where detection and imaging of activated platelets or an associated thrombus cannot readily be performed with traditional optical detection or imaging techniques. These methods can include, for example, endovascular detection. It will be appreciated that the compositions can be used in other in vivo methods as well as intraoperative procedures.

For imaging methods, a plurality of the heteromultivalent nanoparticles can be delivered to the targeted activated platelets and nearby tissue of the subject in vivo by administering an effective amount or concentration of the compositions to the subject. By effective amount or concentration of the composition, it is meant an amount of the compositions that are effective for detecting and imaging the targeted activated platelets or nearby tissue. As apparent to one skilled in the art, such an amount will vary depending on factors that include: the amount of tissue to be imaged; the rate of contact of the compositions with the platelets; and any abnormalities of the platelets or thrombus site that may affect the efficiency of the nanoparticle or microparticle construct of the composition contacting or binding to the targeted activated platelets.

In some embodiments, the heteromultivalent nanoparticle or microparticle composition can be administered to the subject by venous (or arterial) infusion. In venous infusion, an effective amount or concentration of the composition administered to subject can be that amount or concentration that is detectable in the targeted platelets or associated disease site after sequestration of the composition in the liver, spleen, and lymph nodes. Optionally, the composition can be administered to the subject by directly injecting the nanoparticle or microparticle construct into the vasculature of the area being identified or an area proximate or peripheral to the area being identified. Direct injection of the nanoparticle or microparticle construct can be performed by using, for example, a syringe.

In other embodiments, the nanoparticles can be administered to a subject for imaging at least one region of interest (ROI) of the subject. The ROI can include a particular area or portion of the subject and, in some instances, two or more areas or portions throughout the entire subject. The ROI can include, for example, pulmonary regions, gastrointestinal regions, cardiovascular regions (including myocardial tissue), renal regions, as well as other bodily regions, tissues, lymphocytes, receptors, organs and the like, including the vasculature and circulatory system, and as well as diseased tissue, including neoplastic or cancerous tissue. The ROI can include regions to be imaged for both diagnostic and therapeutic purposes. The ROI is typically internal; however, it will be appreciated that the ROI may additionally or alternatively be external. For example, the ROI can include a thrombus site or any occlusive vascular disease site in a subject.

At least one image of the ROI can be generated using an imaging modality once the targeted nanoparticles localize to the ROI. The imaging modality can include one or a combination of known imaging techniques capable of visualizing the nanoparticles. Examples of imaging modalities can include ultrasound (US), magnetic resonance imaging (MRI), nuclear magnetic resonance (NMR), computed topography (CT), electron spin resonance (ESR), nuclear medical imaging, optical imaging, and positron emission topography (PET).

In one example, the nanoparticles can be detected with MRI and/or x-ray. MRI relies upon changes in magnetic dipoles to perform detailed anatomic imaging and functional studies. For example, the electron dense core of GNRs of the nanoparticle, can make them highly visible on X-ray, monochromatic X-ray, computed tomography (CT) and ultrasound (US).

Optionally, the nanoparticles can be further modified to facilitate detection and imaging with MRI and CT as well as positron emission tomography (PET). For MRI applications, gadolinium tags can be attached to the shell. For PET applications, radioactive tags can be attached to nanoparticles. For CT applications, iodide or other heavy metals can be attached to the nanoparticles to facilitate CT contrast.

It will be appreciated the nanoparticles will likely be most useful clinically when several imaging techniques or imaging followed by a medical or surgical procedure is used. In this way, the ability to use one agent for multiple imaging modalities is optimized making the nanoparticles cost-competitive with existing contrast agents.

For multimodal imaging applications, the nanoparticles can be administered to a subject and then preoperatively imaged using, for example, CT or MRI. After preoperative imaging, the nanoparticles can serve as optical beacons for use during surgery leading to more complete resections or more accurate biopsies. In surgical resection of lesions, the completeness of resection can be assessed with intra-operative ultrasound, CT, or MRI. For example, in glioma (brain tumor) surgery, the nanoparticles can be given intravenously about 24 hours prior to pre-surgical stereotactic localization MRI. The nanoparticles can be imaged on gradient echo MRI sequences as a contrast agent that localizes with a thrombus.

In many occlusive vascular diseases like stroke, myocardial infarction, peripheral arterial diseases and deep vein thrombosis, thrombo-occlusion and ischemia can deprive vital organs of circulation, oxygen and nutrients, leading to tissue and organ morbidity and often mortality. Rapid clot dissolution and revascularization is a mainstay in the clinical treatment of these critical disease conditions. Therefore, the application further relates to a method of treating a vascular disease in a subject. Vascular diseases and injuries treatable by the nanoparticles described herein can include disease states or injuries characterized in part by the aggregation and/or adhesion of activated platelets in a disease site of subject. In some embodiments, the vascular disease or vascular injury includes an occlusive vascular disease such as but not limited to stroke, myocardial infarction, peripheral arterial diseases and deep vein thrombosis, thrombo-occlusion and ischemia.

A composition comprising the nanoparticles described herein that includes a therapeutic agent for the treatment of vascular disease can be formulated for administration (e.g., injection) to a subject diagnosed with at least one occlusive vascular disease. The nanoparticles can be formulated according to a method as described above and include, for example, at least one therapeutic agent or imaging agent as well as a first and a second targeting moiety to target the activated platelets at the occlusive vascular disease site. The platelet-targeted nanoparticles loaded with a therapeutic agent are further GNR-modified. It is contemplated that compositions of the present application can be administered via I.V.-injection and can stay in circulation long enough to recognize and bind at vascular sites exhibiting platelet hyperactivity. Alternatively, the GNR-modified activated platelet-targeted nanoparticle loaded with a therapeutic agent can be administered via direct I.V. bolus injection at or near the disease site of interest. After an amount of time necessary for the vehicle to bind to thrombotic activated platelets, therapeutic agents encapsulated by the nanoparticles can be rapidly released remotely at the targeted site by utilizing near-infrared (NIR-induced) photothermal destabilization of the GNR-modified nanoparticles. Active platelet-targeted GNR-modified nanoparticles can undergo thrombus-selective binding and retention under dynamic flow and allow NIR-triggered release of drugs for targeted thrombolytic therapy.

In some embodiments, compositions of the application are administered immediately after it has been determined they are clinically appropriate. The advantage of administration is highest within the first sixty minutes after a thrombotic event, but may extend up to six hours after the start of symptoms. In some embodiments, compositions are administered in combination with anticoagulant drugs such as intravenous heparin or low molecular weight heparin, for synergistic antithrombotic effects and secondary prevention.

The following examples are for the purpose of illustration only and are not intended to limit the scope of the claims, which are appended hereto.

Example 1

We have created nanoparticles platforms that bear two types of ligands (a GPIIb-IIIa-targeting peptide and a P-selectin-targeting peptide) together, for simultaneous targeting of GPIIb-IIIa and P-selectin. We have data to demonstrate that such combination targeting results in highly enhanced platelet-selective shear-stable binding under flow, compared to any one type of targeting by itself. Such synergistic targeting mechanisms enable strong site-selective binding under flowing blood.

Natural ligands binding to these two receptors are responsible for stabilizing active platelet interactions at vascular disease sites under a hemodynamic shear environment. Integrin $\alpha IIb\beta 3$ on activated platelets, in its stimulated ligand binding conformation, binds to the bi-dentate ligand fibrinogen (Fg) to promote interlinking of active platelets in primary thrombus formation. This integrin also allows interaction of activated platelets with diseased endothelial cells (ECs) via Fg-mediated crosstalk with integrin $\alpha_v\beta_3$. P-selectins, expressed specifically on activated platelets and stimulated endothelial cells via membrane fusion of cytoplasmic granules, are responsible for allowing interaction of platelets and ECs with monocytes via binding to P-selectin Glycoprotein Ligand-1 (PSGL-1) present on the surface of monocytes. P selectin also mediates interplatelet interactions via sulfatides and platelet interaction with endothelial cells via GlyCAM-1, CD34, and MadCAM 1, providing supplementary mechanisms of platelet-monocyte-EC interaction stabilization at vascular disease sites. Hence, we rationalized that exploiting simultaneous binding to these two receptors by our liposomal nanoconstructs will not only enhance vascular disease site-selectivity, but also provide sufficient binding stability under hemodynamic flow at the target site.

For specific targeting to activated platelets, we have chosen integrin $\alpha IIb\beta 3$ and P-selectin as our molecular target epitopes since they are present at high levels, specifically on the surface of activated platelets. This will enable high selectivity of our liposomal nanoconstructs toward activated platelets and not quiescent platelets and, therefore, will enhance selectivity to vascular disease sites. We have previously demonstrated enhanced targeting of $\alpha IIb\beta 3$ on activated platelets by decorating liposome surface with fibrinogen-mimetic RGD peptides. In current research, we combined $\alpha IIb\beta 3$-targeting by a GSSSGRGDSPA (SEQ ID NO:6) peptide with P selectin targeting by a DAEWVDVS (SEQ ID NO:5) peptide. We carried out heteromultivalent surface-modification of the liposome membrane with these peptides and studied the interaction (specific binding and retention) of the resultant nanoconstructs with collagen-adhered activated platelets in a parallel plate flow chamber (PPFC) at various wall shear values. The binding and retention of dual-targeted constructs were compared to non-targeted or singly-targeted constructs.

Materials and Methods

Materials

Phosphate Buffered Saline (PBS), 3.8% w/v sodium citrate, parformaldehyde (PFA), Bovine Serum Albumin (BSA), Trifluoroacetic acid (TFA), chloroform, methanol, and ethanol were obtained from Thermo Fisher Scientific (Pittsburgh, Pa., USA). Cholesterol, Ninhydrin, Phenol, Potassium cyanide, Pyridine, 1,2-Ethanedithiol (EDT), Thiolanisole, and collagen were obtained from Sigma Aldrich (St. Louis, Mo., USA). All amino acids were purchased from Advanced ChemTech (Louisville, Ky., USA). Polycarbonate filters with 200 nm pores were obtained from Whatman (Kent, UK). Fluorescently-labeled monoclonal antibodies, namely, FITC-anti-CD41a (staining platelet GPIIb-IIIa) and AlexaFluor 647-anti-CD62P (staining activated platelet P-selectin), were obtained from BD Biosciences (San Jose, Calif., USA) and BioLegend (San Diego, Calif., USA), respectively. Adenosine Diphosphate (ADP) was purchased from Bio/Data Corporation (Horsham, Pa., USA). The lipids Distearyl Phosphatidyl Choline (DSPC), Distearyl Phosphatidyl Ethanolamine (DSPE), Polyethylene Glycolmodified DSPE (DSPE-PEG2000), DSPE-NHS ester, and Carboxy-Polyethylene Glycol-modified DSPE (DSPE-PEG2000-NHS ester) were obtained from Avanti Polar Lipids (Alabaster, Ala., USA). N-Hydroxysuccinimide (NHS)-modified fluorophores, namely, NHS-Fluorescein and NHS-Rhodamine were obtained from Invitrogen Corporation (Carlsbad, Calif., USA). The Parallel Plate Flow Chamber (PPFC) system was purchased from Glycotech (Gaithersburg, Md., USA).

Peptide Synthesis and Fabrication of Peptide-Modified Liposomal Nanoconstructs

An 11-residue linear RGD peptide, GSSSGRGDSPA (SEQ ID NO: 2), and an 8-residue P-selectin targeting peptide, DAEWVDVS (SEQ ID NO:5), were synthesized using Fmoc based solid phase chemistry and characterized using MALDI-TOF mass spectroscopy. Negative control peptide sequences, namely GSSSGRGESPA (SEQ ID NO:7) and DAEWVEVS (SEQ ID NO:8), were synthesized and characterized in the same manner. All peptides were conjugated 'on resin' to NHS-ester modified-lipid (DSPE-PEG-NHS ester) by reductive amidation to form DSPE- PEG-peptide (schematic in FIG. 2). Conjugation yield was determined to be 95.8±4.9% using a Ninhydrin assay. To synthesize DSPE-Fluorescein (green fluorescence, λmax~530 nm) or DSPE-Rhodamine (red fluorescence, λmax ~570 nm), the free NH$_2$ termini of DSPE was reacted to the amine reactive NHS-Fluorescein or NHS-Rhodamine at a basic pH. The liposomes were fabricated by homogenizing DSPC (49 mol %), DSPE-PEG-peptide (5 mol %), cholesterol (45 mol %) and DSPE-PEG-Rhodamine or Fluorescein (1 mol %) in 1:1 chloroform:methanol and subjecting the mixture to reverse phase evaporation through several cycles of freeze-thaw, followed by extrusion through a 200 nm polycarbonate membrane to achieve unilamellar vesicles. The formulations of the liposomes used in the experiments are shown in Table 1. For singly-targeted liposomes, the DSPE-PEG-GSSSGRGDSPA (SEQ ID NO: 2) or DSPE-PEG-DAEWVDVS (SEQ ID NO: 5) concentration was kept at 5 mol % total lipid, while for the dual-targeted liposomes the DSPE-PEG-peptide composition was kept at 2.5 mol % total lipid for each type of targeting peptide, such that the cumulative DSPE-PEG-peptide composition was still at 5 mol % total lipid. The size distribution of the liposomal constructs was characterized using dynamic light scattering (DLS) and the constructs were found to have an average diameter of w150 nm following extrusion (FIG. 2).

AlexaFluor 647-anti-CD62P (staining P-selectin) and FITC-anti-CD41a (staining integrin αIIbβ3) followed by fluorescence microscopy imaging. For establishing the receptor specificity of liposome binding, collagen-coated coverslip adhered platelets were incubated with fluorescently-labeled, non-targeted (unmodified) or αIIbβ3-targeted (RGD-modified) or P-selectin-targeted (DAEWVDVS (SEQ ID NO:5)-modified) liposomes (schematics in FIGS. 3 and 4). After 1 h of incubation, the coverslips were gently washed with PBS to remove loosely bound liposomal constructs and imaged using fluorescence microscopy. All images were captured using a Zeiss Axio Observer.D1 inverted fluorescence microscope fitted with a photometrics chilled CCD camera and a 63× objective using exposure time of 800 ms. To confirm that non-specific binding of the liposomes was not occurring, fluorescently-labeled peptide-modified liposomal constructs were incubated with coverslips coated with collagen only but no activated platelets, followed by gentle washing and imaged using fluorescence microscopy keeping same exposure times (800 ms).

Receptor-Specific Blocking Studies in a Static Environment

As additional verification of the peptide-modified liposomal constructs binding specificity to the respective activated platelet surface target receptors, blocking studies were carried out. First, activated platelets were adhered onto

TABLE 1

Components of liposomes used in the experiments.

| Liposome type | Liposome components | | | |
|---|---|---|---|---|
| Non-targeted (Unmodified) | DSPC: 49 mol% | DSPE-PEG: 5 mol% | Cholesterol: 45 mol% | DSPE-PEG-Rhodamine or Fluorescein: 1 mol% |
| GPIIb-IIIa-targeted (RGD-modified) | DSPC: 49 mol% | DSPE-PEG-GSSSGRGDSPA (SEQ ID NO: 2): 5 mol% | Cholesterol: 45 mol% | DSPE-PEG-Rhodamine or Fluorescein: 1 mol% |
| P-selectin-targeted (DAEWVDVS-modified) | DSPC: 49 mol% | DSPE-PEG-DAEWVDVS (SEQ ID NO: 5): 5 mol% | Cholesterol: 45 mol% | DSPE-PEG-Rhodamine or Fluorescein: 1 mol% |
| Dual-targeted (modified simultaneously with both peptides) | DSPC: 49 mol% | DSPE-PEG-GSSSGRGDSPA (SEQ ID NO: 2): 2.5 mol% DSPE-PEG-DAEWVDVS (SEQ ID NO: 5): 2.5 mol% | Cholesterol: 45 mol% | DSPE-PEG-Rhodamine or Fluorescein: 1 mol% |

In Vitro Studies to Confirm Targeting Specificity and Enhanced Binding Stability of Constructs Receptor-specific binding studies in a static environment human whole blood was obtained from healthy, aspirin-refraining donors by venipuncture following IRB-approved protocol and collected in citrated tubes. Platelet-rich-plasma (PRP) was obtained from the whole blood by centrifugation (150×g, 15 min, room temperature), and platelet concentration was verified at 200×10$^6$ platelets/ml. The platelets in PRP were activated using ADP at a concentration of 2×10$^{-5}$ M, and were allowed to adhere to glass coverslips pre-coated with collagen. The adhered platelets were subsequently fixed with 4% paraformaldehyde, and their presence on the coverslip was confirmed by immunostaining with collagen coated coverslips as previously described. Next, nonfluorescent RGD-modified or DAEWVDVS (SEQ ID NO:5)-modified liposomal constructs were incubated with the coverslip adhered platelets for 1 h. After 1 h, the coverslips were gently washed with PBS and further incubated with fluorescent FITC anti-CD41a or AlexaFluor 647-anti-CD62P for 30 min. Similar activated platelets adhered onto collagen-coated coverslips were incubated with FITC-anti-CD41a or AlexaFluor 647-anti-CD62P without prior incubation with the non-fluorescent peptide-modified liposomes. The rationale was that if the peptide-modified liposomal constructs bound their specific target receptors, then the pre-incubation with the liposomes would possibly occupy many of these receptors and block them from binding the fluorescent antibodies in the subsequent step (schematics in FIGS. 5 and 6). On the other hand, without liposome pre-incubation, the fluorescent antibodies would successfully stain the respective receptors. All coverslips were imaged as previously described.

Flow Cytometry Analysis of Platelet-Targeting by Peptide-Modified Constructs

Liposomal construct binding to activated platelets was also studied using an LSRII (Becton Dickinson) flow cytometer (Blue 488 nm and Red 640 nm lasers). Whole blood aliquots were incubated with ADP for 30 min to activate the platelet population. Samples were then fixed with 4% paraformaldehyde for 1 h. The level of platelet activation was assessed by co-staining the aliquot with FITC-conjugated anti-CD41a antibody and AlexaFluor 647-conjugated anti-CD62P antibody and running the sample through the flow cytometer to assess the fluorescence associated with the gated platelet population. Following confirmation of platelet activation, duplicate whole blood aliquots were incubated with Rhodamine B-labeled non-targeted (unmodified), singly-targeted (RGD-modified OR DAEWVDVS (SEQ ID NO:5)-modified), or dual-targeted (both RGD and DAEWVDVS (SEQ ID NO:5)-modified) liposomes at a final concentration of 500 mM total lipid for 30 min and run through the flow cytometer to analyze platelet-associated fluorescence. For control studies, the aliquots were subjected to liposome incubation without pre-incubation with ADP (no platelet activation). For all analyses, gated platelet population fluorescence was analyzed at 20,000 counts per aliquot.

Binding Stability and Retention Studies in Parallel Plate Flow Chamber (PPFC)

Figure 7:
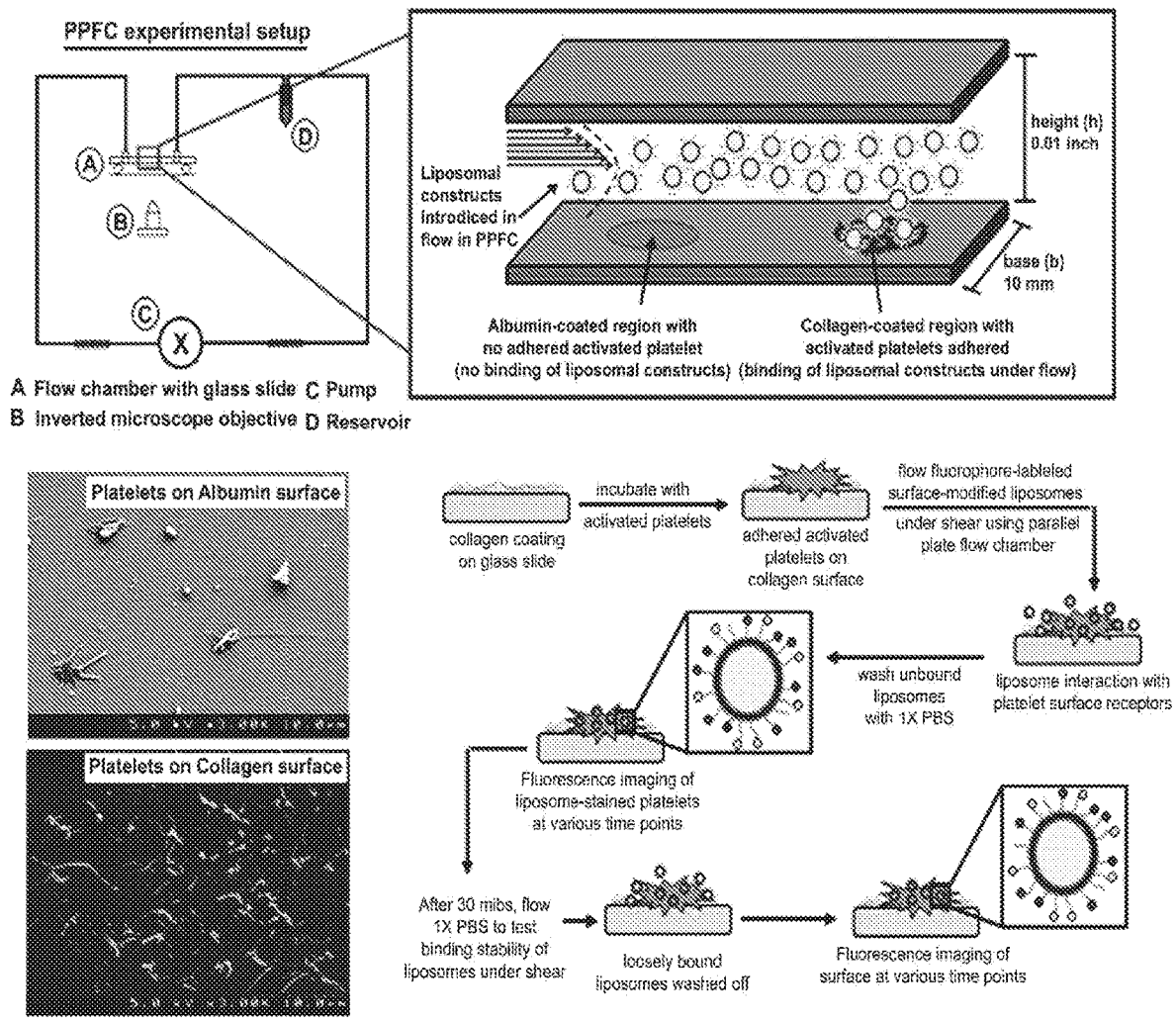
FIG. 7 illustrates schematic representation of experimental set-up and procedure for the PPFC experiments to establish the enhanced binding and retention of peptide-modified liposomes to activated platelets under hemodynamic flow relevant shear stress ranges over time; the bottom left also shows representative SEM images of albumin-coated surface area and collagen-coated surface area after incubation with activated platelets, confirming that the collagen-coated surface has a significantly high density of active platelets; allowing the test and control liposomes to interact with platelet-rich (collagen-coated) and platelet-deficient (albumin-coated) surface regions on the same slide under various shear stress ranges in the PPFC set-up for effective analysis of liposome binding and retention.

A standard PPFC system (10 mm width-0.01 in height) fitted to a peristaltic pump and placed under an inverted epifluorescence microscope was used for studying interaction of liposomal constructs with surface-adhered platelets under a flow environment (schematic in FIG. 7). The PPFC system allows variation of wall shear stress ($\tau_w$) at the plate surface by modulating the flow rate (Q) of the fluid through the chamber, according to the equation $\tau_w = 6 \mu Q w^{-1} h^{-2}$, where 'µ' is fluid viscosity, 'w' is chamber width and 'h' is chamber height. Similar flow chamber set-ups have been reported for analysis of cell-material interactions in a dynamic flow environment. For PPFC studies, glass microscope slides were coated in two equal circular area regions with albumin and collagen. The slides were allowed to sit in contact with PRP in presence of ADP or BSA for 1 h to render adhesion of activated platelets to the collagen coated region; the albumin-coated region does not adhere activate platelets and hence act as the control area. After fixing with 4% paraformaldehyde and immunostaining with FITC-anti CD41a and AlexaFluor 647-anti-CD62P, the collagen-coated region revealed dense adhesion and aggregation of platelets (simulating a thrombotic region), while the albumin coated region had almost no adhered platelets. This fluorescence microscopy information was further complimented by Scanning Electron Microscopy (SEM) images (representative images shown in FIG. 7). After confirming the activated platelet-adhered and platelet-deficient regions on the glass slides, similar PRP-incubated slides but without platelet immunostaining were placed in the PPFC, and Rhodamine-labeled (red fluorescent) peptide-modified (singly-targeted or dual-targeted) or unmodified liposomes were allowed to flow through the chamber in a PBS suspension (total lipid concentration of 1 mM) for 30 min. The flow was maintained at various flow rates for different batches of experiments to allow varying wall shear stress values in the range between 5 and 60 dyn/cm². After 30 min, the liposome solution was replaced with PBS and the flow was maintained for another 15 min to determine the stability of binding of the liposomes in the dynamic flow environment. Throughout this procedure, at various time points and for various flow rates (hence shear stresses), the glass slides were imaged under an epifluorescence microscope as previously described.

Data Analysis

For fluorescence images from the binding/blocking studies under both static and dynamic conditions, adhesion and retention was quantified using raw image analysis of surface averaged intensity values in Adobe Photoshop CS4 software. Statistical analysis of the static binding/blocking results was done using Paired Student's t-tests, and statistical analysis of dynamic binding results was done using ANOVA. For all statistical analysis, significance was considered at $p < 0.05$.

Results

We have developed liposomal nanoconstructs that are simultaneously surface modified with two types of peptide ligands having specificity and high affinity to two different cell-surface receptors on activated platelets, namely integrin $\alpha II_b \beta_3$ (also known as glycoprotein GPIIb-IIIa) and P-selectin (FIG. 1).

Receptor-Specific Binding Studies and Blocking Studies in a Static Environment

Figure 3:
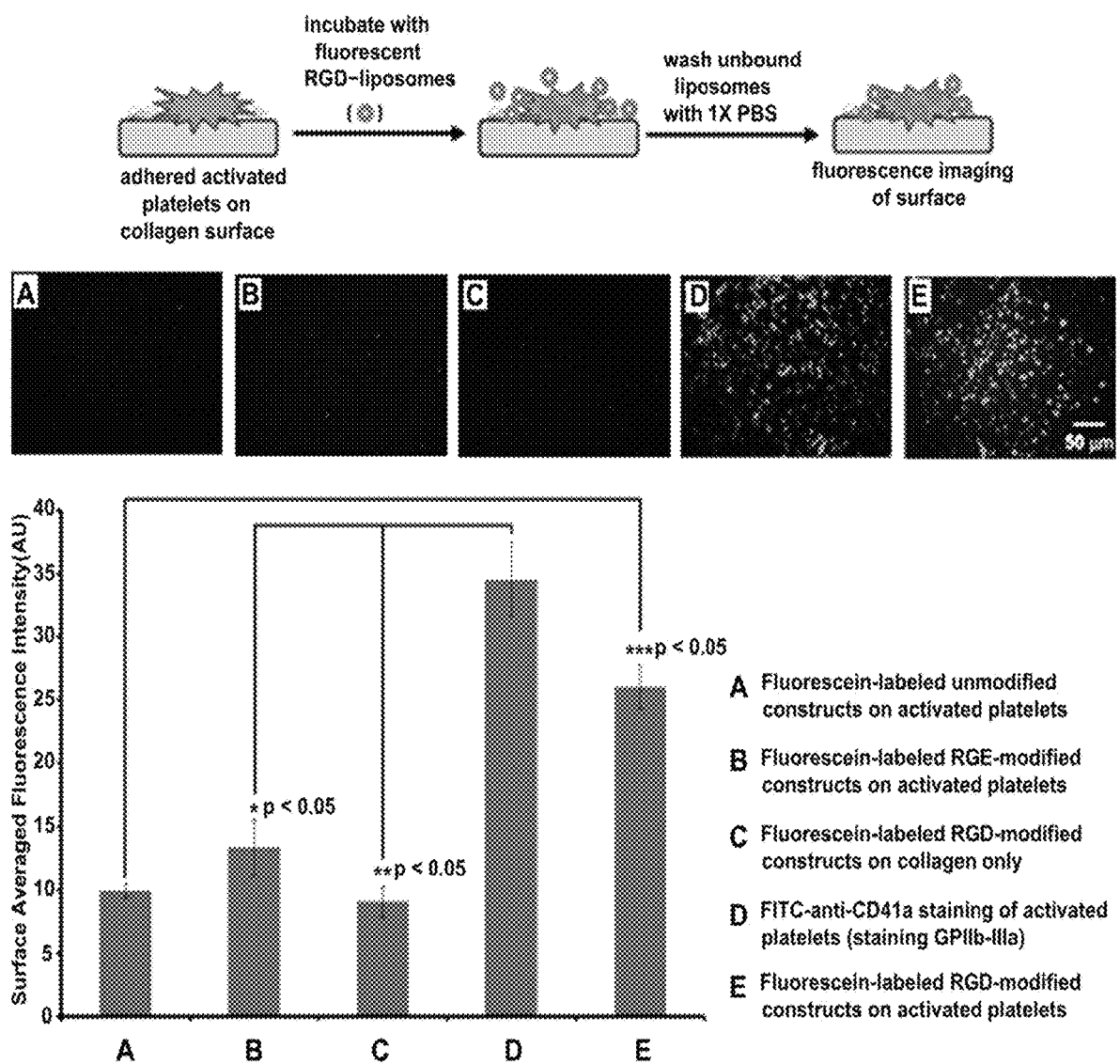
FIGS. 3(A-E) illustrate a fluorescence microscopy experiment to establish the specific binding of RGD-modified liposomes to activated platelets; top panel shows the experiment procedure; middle panel shows representative microscope images of control and test conditions (A through E); the quantitative analysis of fluorescence intensity from multiple images (n=10 per test or control condition) at these conditions are shown in the graph at the bottom, confirming the enhanced binding of activated platelets by RGD-modified liposomes compared to unmodified liposomes.
Figure 4:
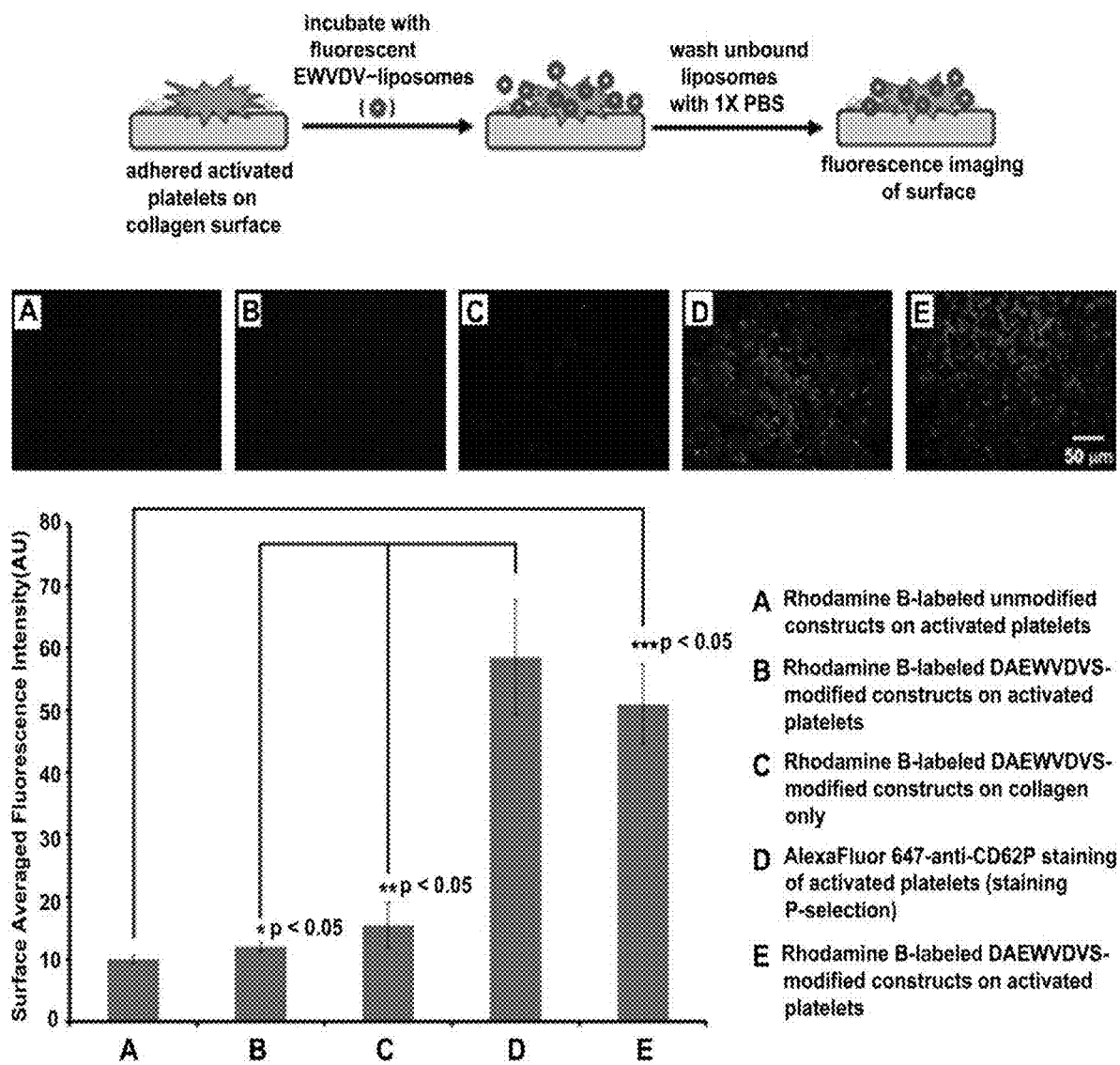
FIGS. 4(A-E) illustrates a fluorescence microscopy experiment to establish the specific binding of DAEWVDVS (SEQ ID NO: 5)-modified liposomes to activated platelets; top panel shows the experiment procedure with EWVDVS (SEQ ID NO: 1); middle panel shows representative microscope images of control and test conditions (A through E); the quantitative analysis of fluorescence intensity from multiple images (n=10 per test or control condition) at these conditions are shown in the graph at the bottom, confirming the enhanced binding of activated platelets by DAEWVDVS (SEQ ID NO: 5)-modified liposomes compared to unmodified liposomes.
Figure 5:
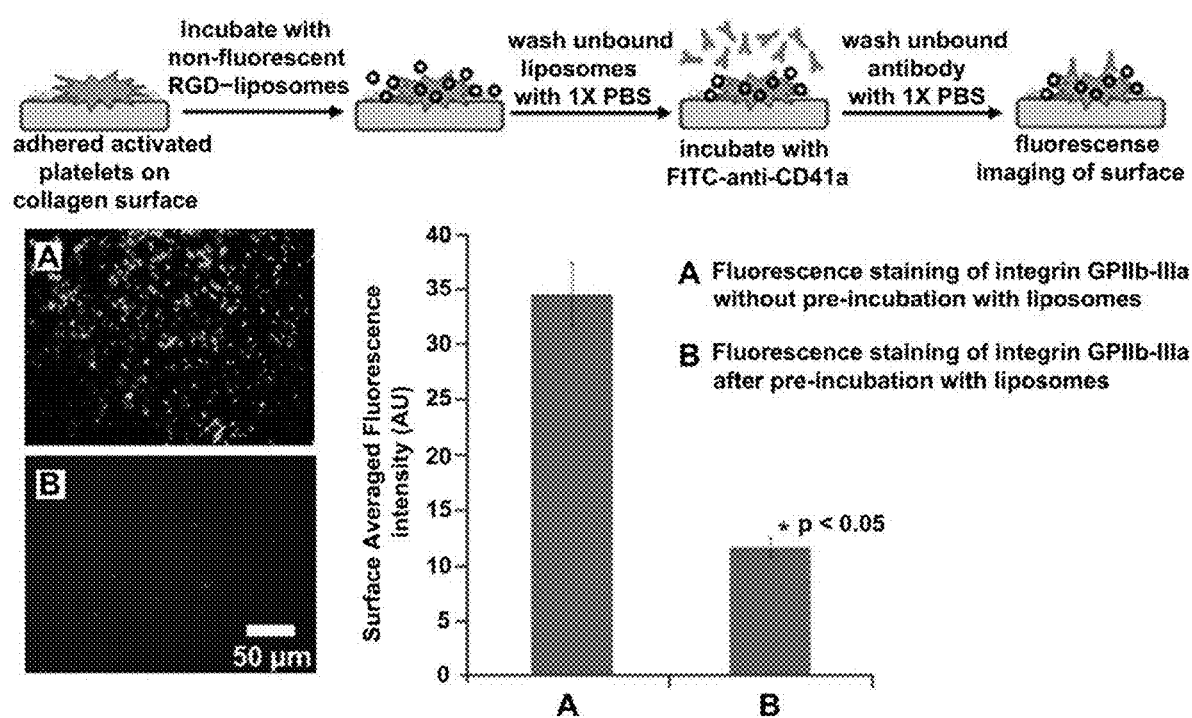
FIGS. 5(A-B) illustrate the specific receptor blocking studies analyzed by fluorescence microscopy to establish that RGD-modified liposomes bind to GPIIb-IIIa on activated platelets; top panel shows the experiment procedure; middle panel shows representative microscope images of control and test conditions; the quantitative analysis of fluorescence intensity from multiple images (n=10 per test or control condition) at these conditions are shown in the graph at the bottom, confirming that pre incubation of activated platelets with RGD-modified liposomes results in significant blocking of fluorescent antibody specifically binding to activated platelet GPIIb-IIIa; this result in combination with results shown in FIG. 3 confirm that the RGD-modified liposomes can specifically target and bind to GPIIb-IIIa on activated platelets.
Figure 6:
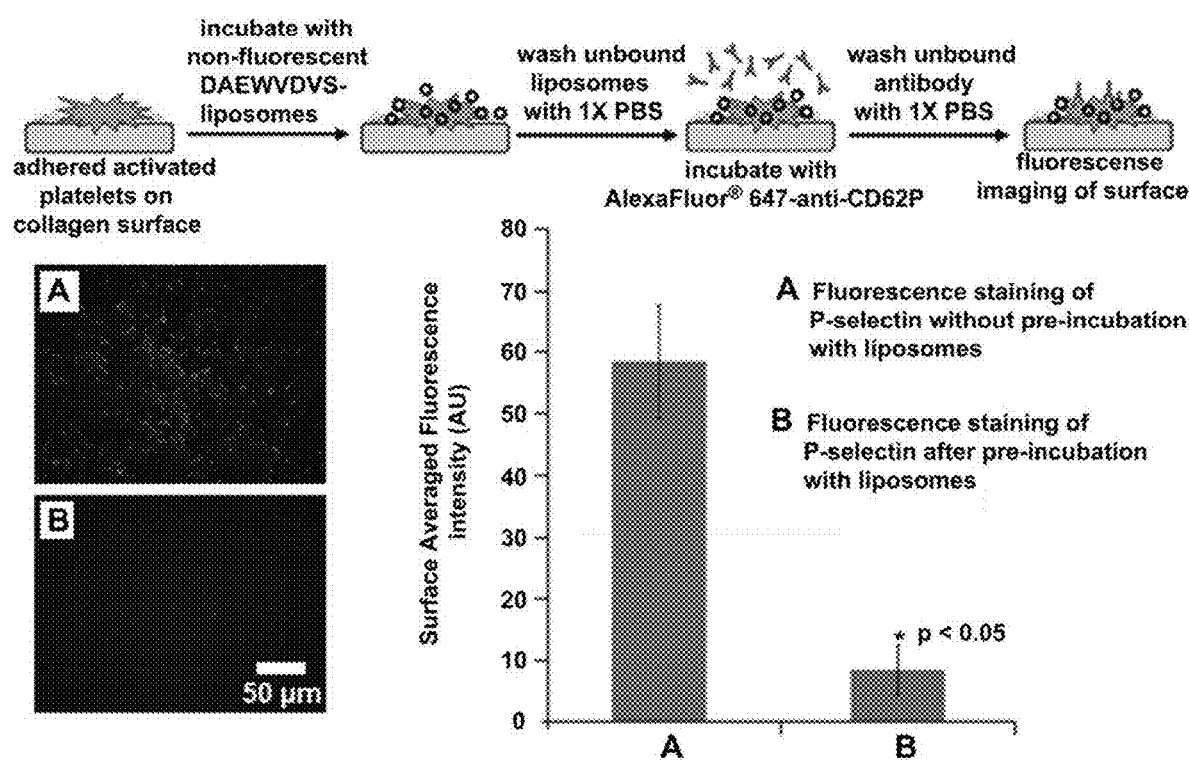
FIGS. 6(A-B) illustrate specific receptor blocking studies analyzed by fluorescence microscopy to establish that DAEWVDVS (SEQ ID NO: 5)-modified liposomes bind to P-selectins on activated platelets; top panel shows the experiment procedure; middle panel shows representative microscope images of control and test conditions; the quantitative analysis of fluorescence intensity from multiple images (n=10 per test or control condition) at these conditions are shown in the graph at the bottom, confirming that pre-incubation of activated platelets with DAEWVDVS (SEQ ID NO: 5)-modified liposomes results in significant blocking of fluorescent antibody specifically binding to activated platelet P-selectins; this result in combination with results shown in FIG. 4 confirm that the DAEWVDVS (SEQ ID NO: 5)-modified liposomes can specifically target and bind to P-selectins on activated platelets.

FIGS. 3 and 4 show representative fluorescence microscopy images for the receptor-specific binding studies with RGD-modified and DAEWVDVS (SEQ ID NO:5)-modified liposomal constructs, respectively, along with corresponding quantitative data of surface-averaged fluorescence intensity analysis. As evident from the data, both RGD-modified and DAEWVDVS (SEQ ID NO:5)—modified liposomal constructs were able to significantly bind activated platelets by specific interaction with their respective target receptors, but had minimal non-specific binding with collagen itself in the absence of adhered active platelets. Constructs without any peptide modification or bearing negative control peptides had negligible binding to activated platelets. The target receptor specificity of the binding was further confirmed by the results of the receptor blocking studies as shown in FIGS. 5 and 6. As evident from the figures, pre incubation with the RGD-modified nonfluorescent constructs was able to block subsequent binding of FITC-anti-CD41a to integrin αIIbβ3, while pre-incubation with the DAEVWVDVS (SEQ ID NO:5)-modified nonfluorescent constructs was able to block subsequent binding of AlexaFluor 647-anti-CD62P to P-selectin on activated platelets.

Flow Cytometry Analysis of Binding

Figure 8:
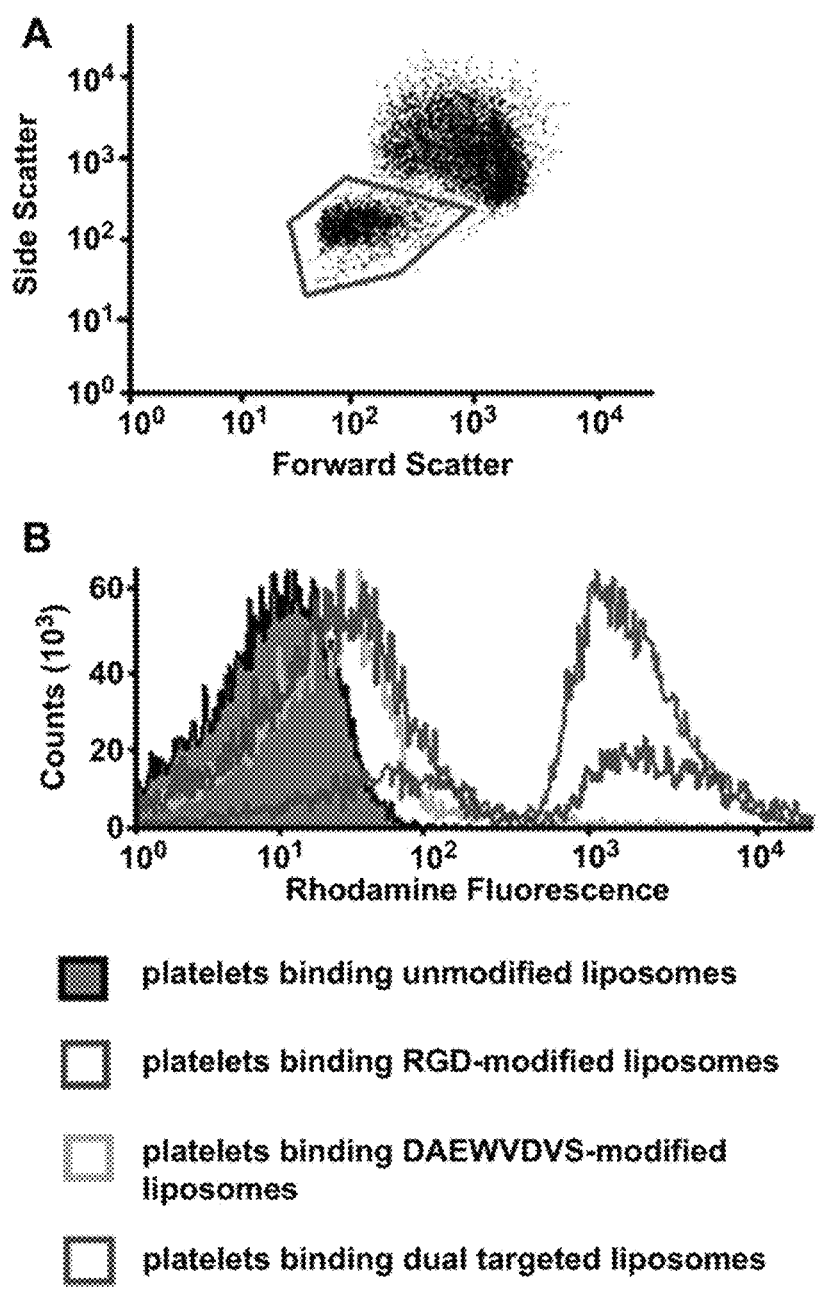
FIGS. 8(A-B) illustrate a representative flow cytometry results showing (A) the gated activated platelet population in whole blood aliquots under analysis and (B) the fluorescence histograms from platelet population interacting with unmodified (non-targeted), RGD-(SEQ ID NO: 2) or DAEWVDVS (SEQ ID NO: 5)-modified (singly-targeted) and simultaneous RGD-(SEQ ID NO: 2) and DAEWVDVS (SEQ ID NO: 5)-modified (dual-targeted) fluorescently-labeled liposomes; it is evident that though the singly-targeted liposomes are capable of binding activated platelets significantly more than the non-targeted liposomes, the dual-targeted liposomes have even higher extent of binding activated platelets when compared to the singly-targeted liposomes.

FIG. 8 shows representative flow cytometry scatter plot of the whole blood aliquot, the gated activated platelet population analyzed for fluorescence, and representative fluorescence histograms of ADP-activated aliquots incubated with non-targeted, singly-targeted (RGD-modified or DAEWVDVS (SEQ ID NO:5)-modified) and dual-targeted (simultaneously RGD- and DAEWVDVS (SEQ ID NO:5)-modified) liposomal constructs. As evident from the data, the RGD-modified and the DAEWVDVS (SEQ ID NO:5)-modified constructs were individually able to bind activated platelets significantly higher than non-targeted constructs. Furthermore, when the two peptide modifications were combined on a single construct, the resultant dual-targeted constructs showed much enhanced binding to activated platelets compared to the singly-targeted constructs. This validates our rationale that the dual targeting approach will render enhanced targeting efficacy toward activated platelets, which in essence, would enhance the binding selectivity of these constructs at sites of vascular disease where large numbers of activated platelets are involved.

Binding Stability and Retention Studies in Parallel Plate Flow Chamber (PPFC)

Figure 9:
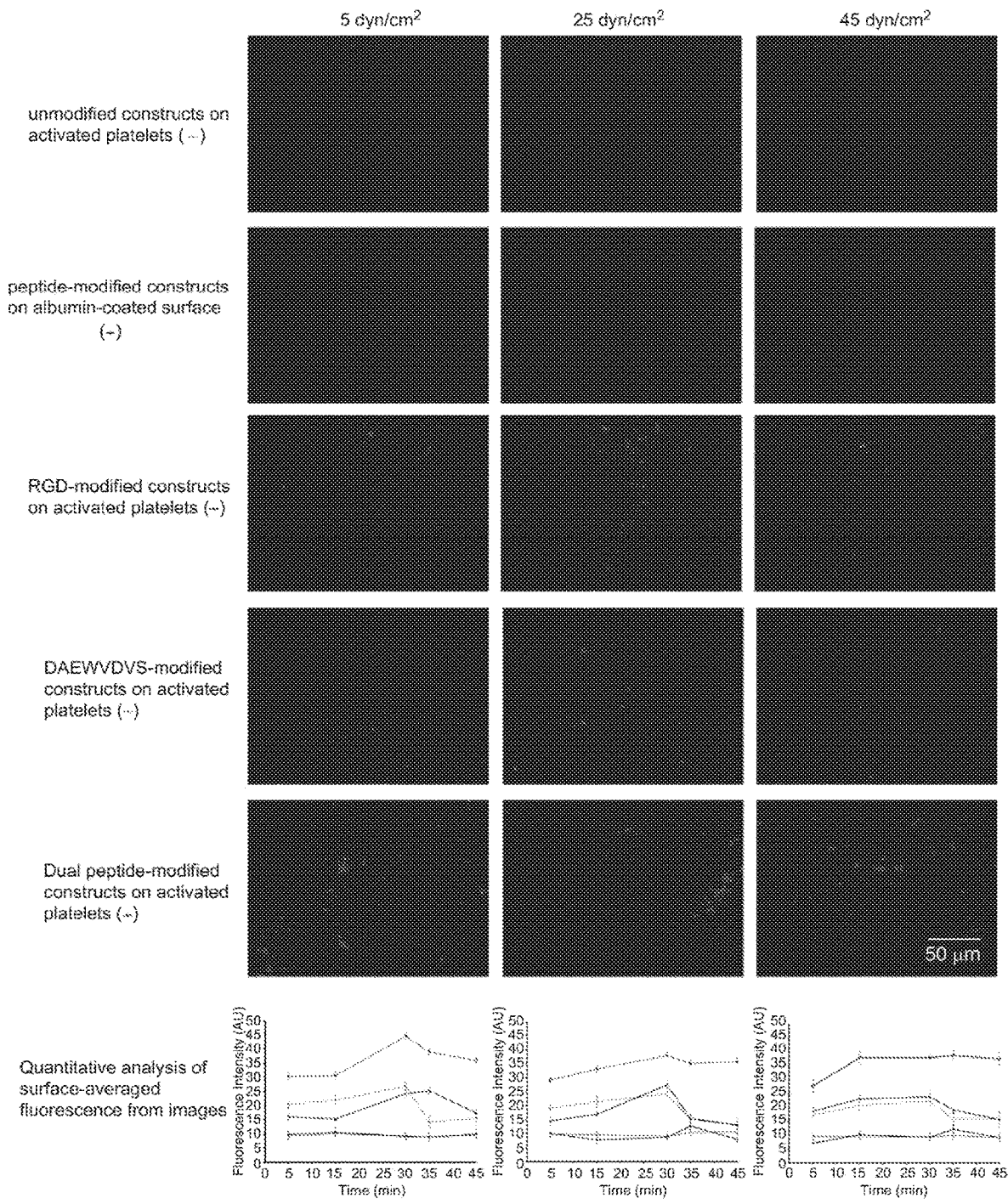
FIG. 9 illustrates a representative fluorescence microscopy images and quantitative data from PPFC experiments to study binding and retention of test (singly or dual-targeted) and control (non-targeted) liposomes to activated platelet-coated surface versus platelet-deficient surface under flow at three different shear stress values (low-to-high shear) over a period of 45 min (30 min liposomal suspension flow+15 min 1×PBS flow); it is evident that in a dynamic flow environment, dual-targeted liposomes are capable of binding and staying retained on target cells (activated platelets) at significantly enhanced levels over time at all shear stress values compared to non-targeted and even singly-targeted liposomes.

FIG. 9 shows representative fluorescent images of construct interaction with test (platelet-covered) and control (albumin without platelet) surface regions on the glass slide in PPFC at three shear values (5, 25 and 45 dyn/cm2) for the 30 min time point. The bottom panel of FIG. 9 also shows quantitative analysis of surface-averaged fluorescence from images at three shear stress values over a period of 45 min (30 min of liposomal construct flow in recirculating loop+15 min of plain PBS flow in open loop) for the various test and control samples. As evident from the qualitative images, the RGD-modified liposomal constructs, the DAEWVDVS (SEQ ID NO:5)-modified liposomal constructs, and the dual-targeted constructs were all able to significantly bind the activated platelet covered surface under flow compared to unmodified (non-targeted) liposomal constructs or platelet-deficient (albumin) surfaces. The quantitative analysis shows that the dual-targeted liposomal constructs have significantly enhanced binding and retention on activated platelets under flow compared to the singly-targeted constructs. This validates our rationale that the dual targeting not only enhances the selectivity of activated platelet targeting (complementary results to flow cytometry data), but also enhances the strength of binding to ensure higher retention at the target site under a dynamic flow environment.

Figure 10A:
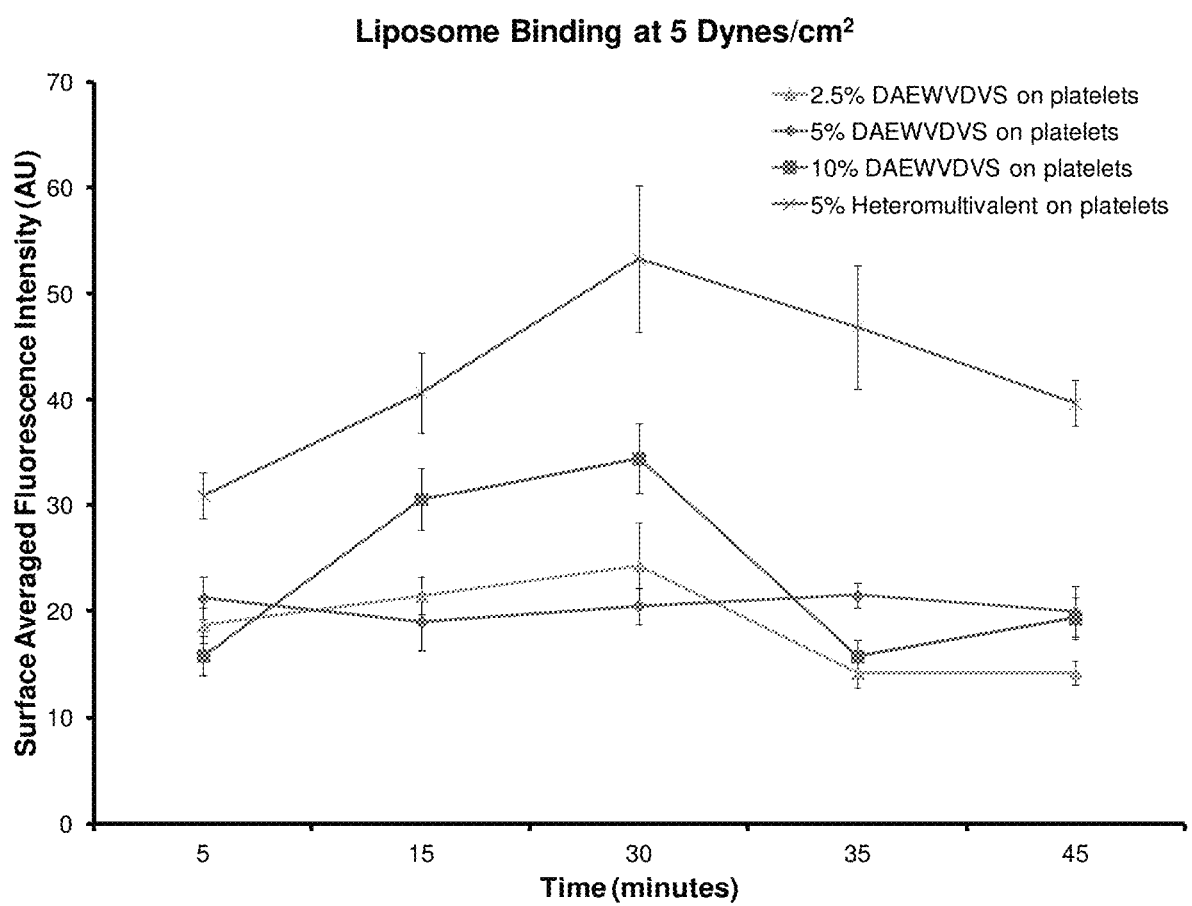
FIGS. 10(A-C) are graphical illustrations of nanovehicle binding to active platelets using varying mole % of ligands directed to GPIIb-IIIa and P-selectin at a flow rate of (A) 5 Dynes/cm$^2$, (B) 25 Dynes/cm$^2$ and (C) 55 Dynes/cm$^2$. Binding is measured by the surface averaged fluorescence intensity (AU) over time (mins). Results show the liposome binding generated at flow rates of 5 Dynes/cm$^2$, 25 Dynes/cm$^2$ and 55 Dynes/cm$^2$ and using 2.5%, 5%, and 10% DAEWVDVS (SEQ ID NO: 5) peptide directed to P-selectin (singly-targeted) and 5% DAEWVDVS (SEQ ID NO: 5) peptide/RGD (SEQ ID NO: 2) heteromultivalent peptides.
Figure 10B:
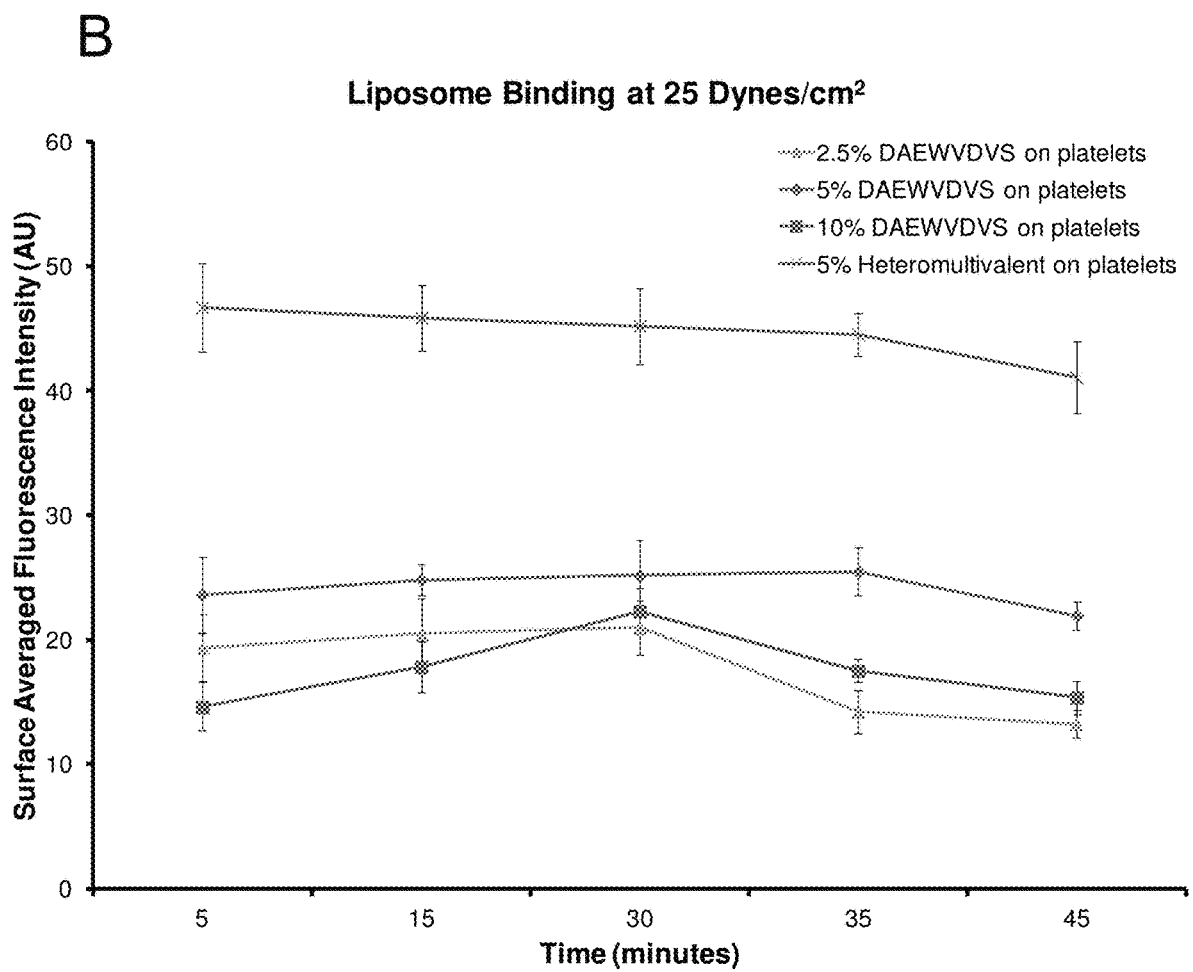
Figure 10C:
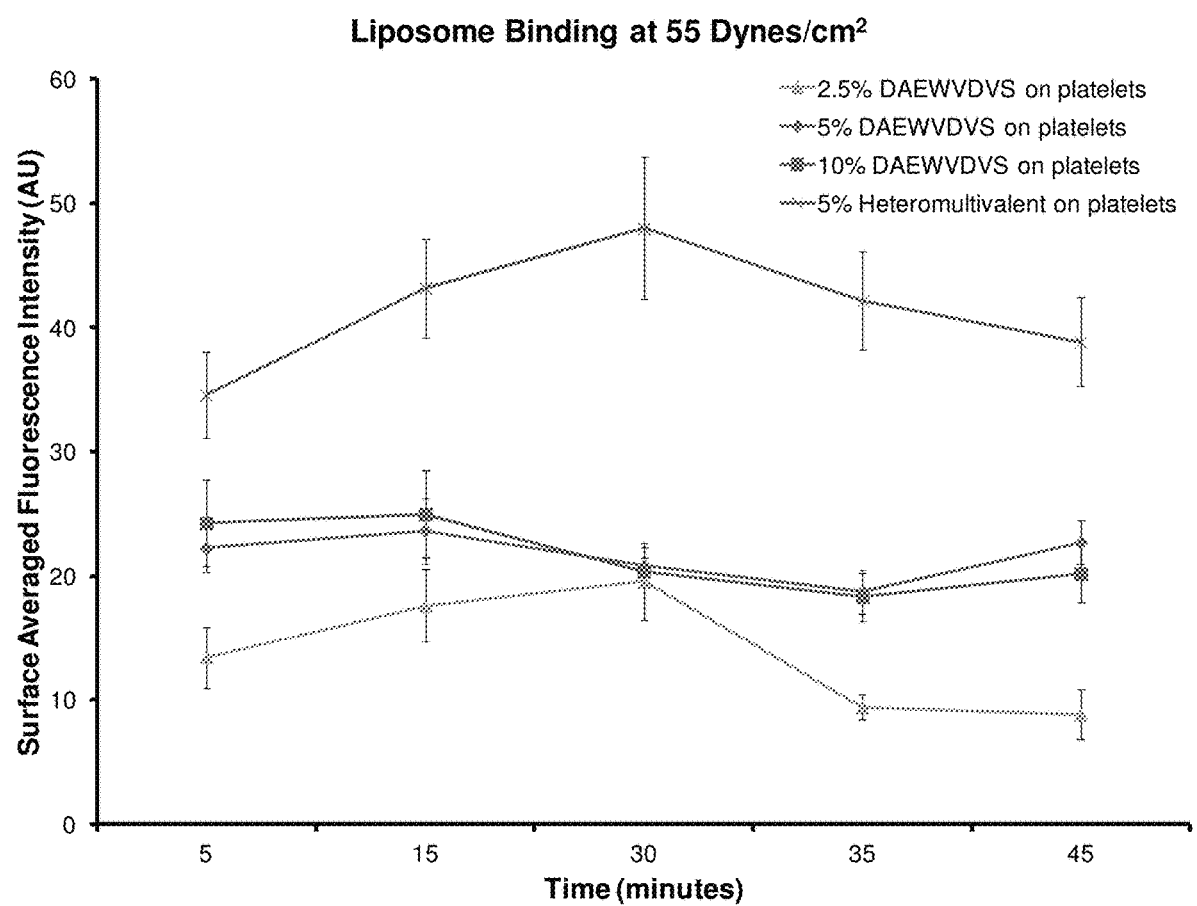

Nanovehicle Binding to Active Platelets Using Varying Mole % of Ligands Directed to GPIIb-IIIa and P-Selectin FIG. 10a-c shows that multi-receptor targeted strategy results in higher binding and retention of nanovehicles on active platelets under flow conditions, compared to single receptor targeting at the same mol % and that multi-receptor targeting allows for achieving enhanced binding and retention with lower mol % of total ligands, compared to single receptor targeting with only one type of ligand.

Figure 11A:
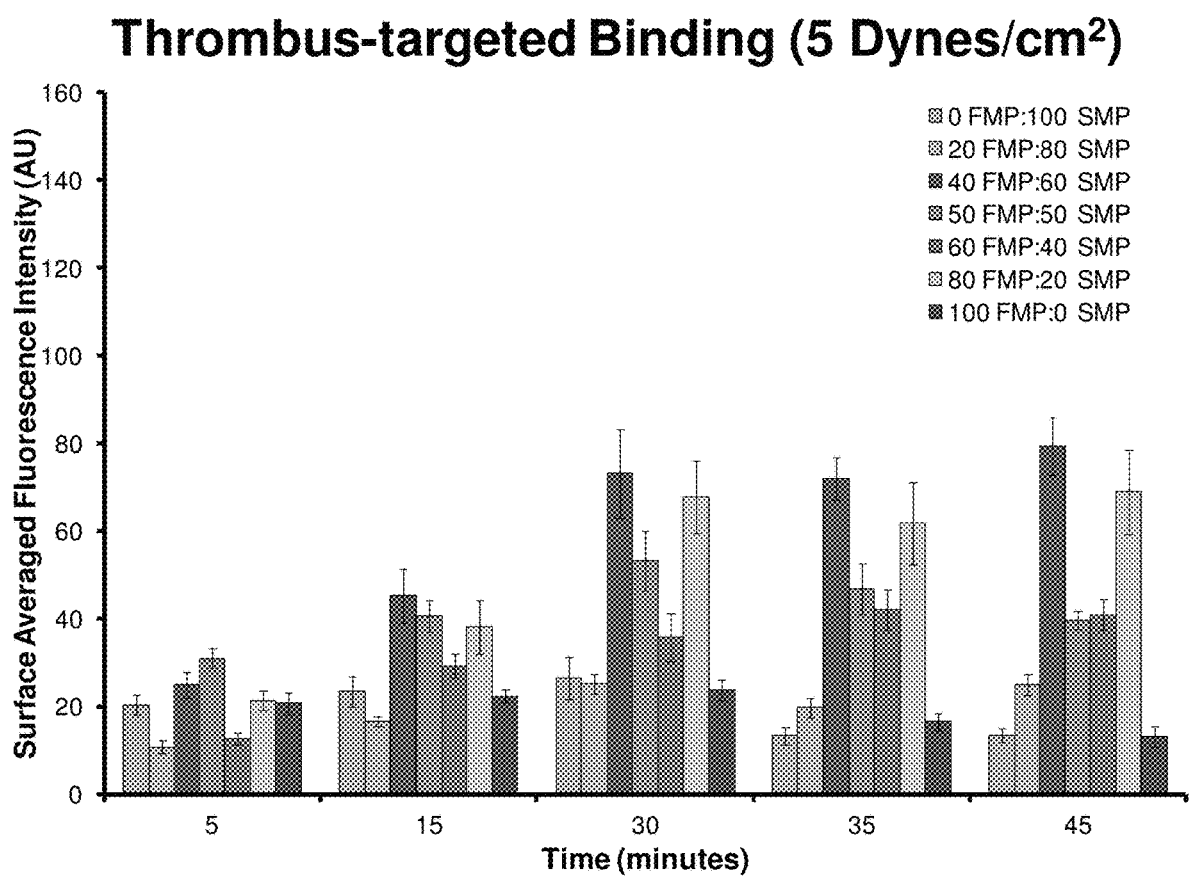
FIGS. 11(A-C) are graphical illustrations of nanovehicle binding to active platelets using fixed mole % but varying ratios of ligands directed to GPIIb-IIIa and P-selectin at flow rates of (A) 5 Dynes/cm$^2$, (B) 25 Dynes/cm$^2$ and (C) 55 Dynes/cm$^2$. Binding is measured by the surface averaged fluorescence intensity (AU) over time (mins). Results show the thrombus-targeted liposome binding generated at a flow rate of 5 Dynes/cm$^2$ using 2.5%, 5%, and 10% DAEWVDVS (SEQ ID NO: 5) peptide directed to P-selectin (singly-targeted) and 5% DAEWVDVS (SEQ ID NO: 5) peptide/RGD heteromultivalent peptides.
Figure 11B:
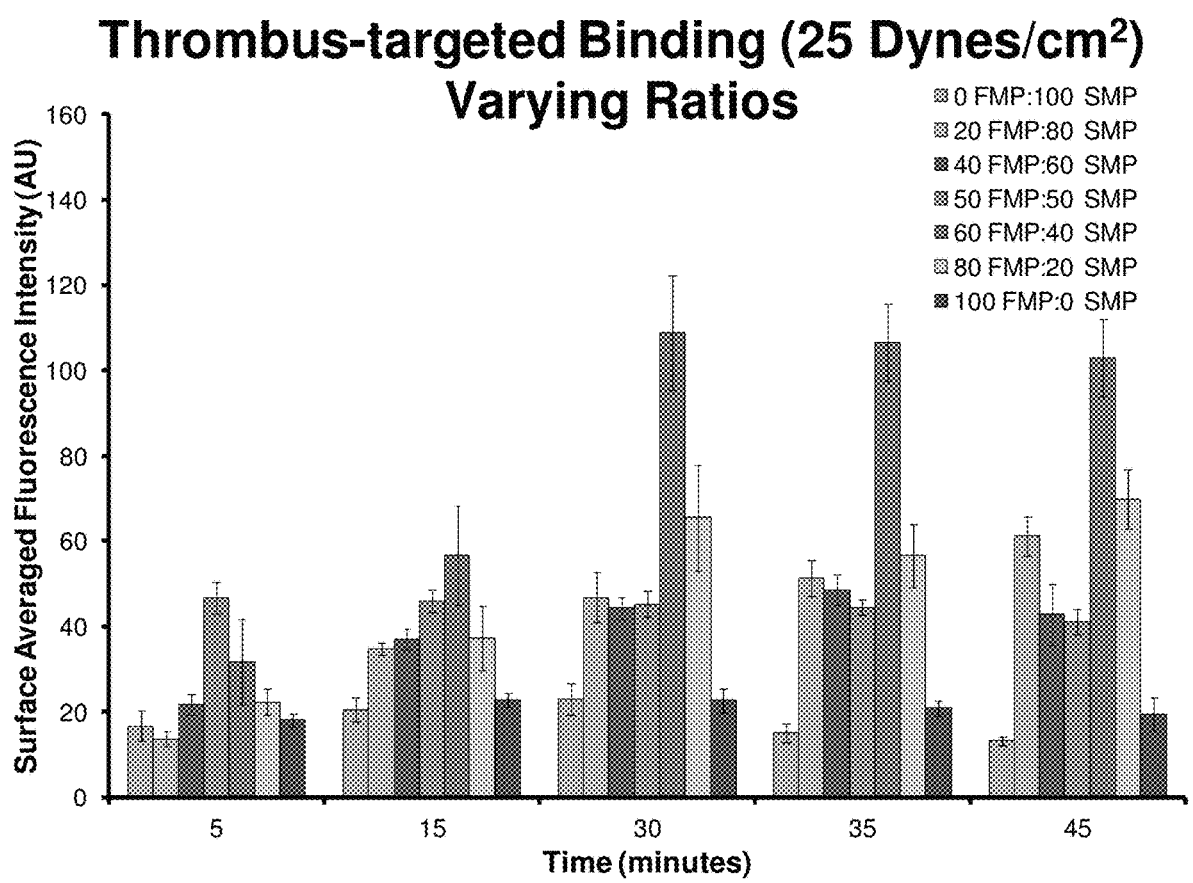
Figure 11C:
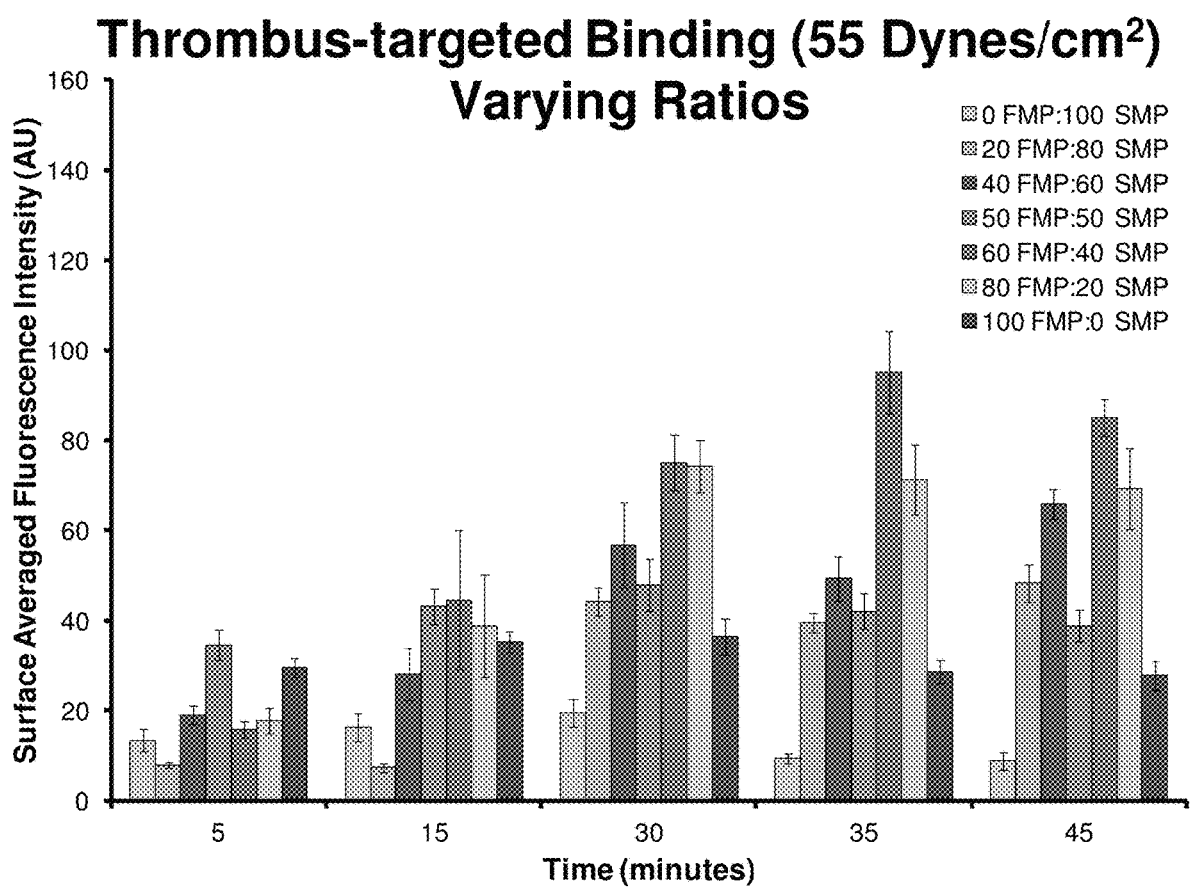
Figure 12:
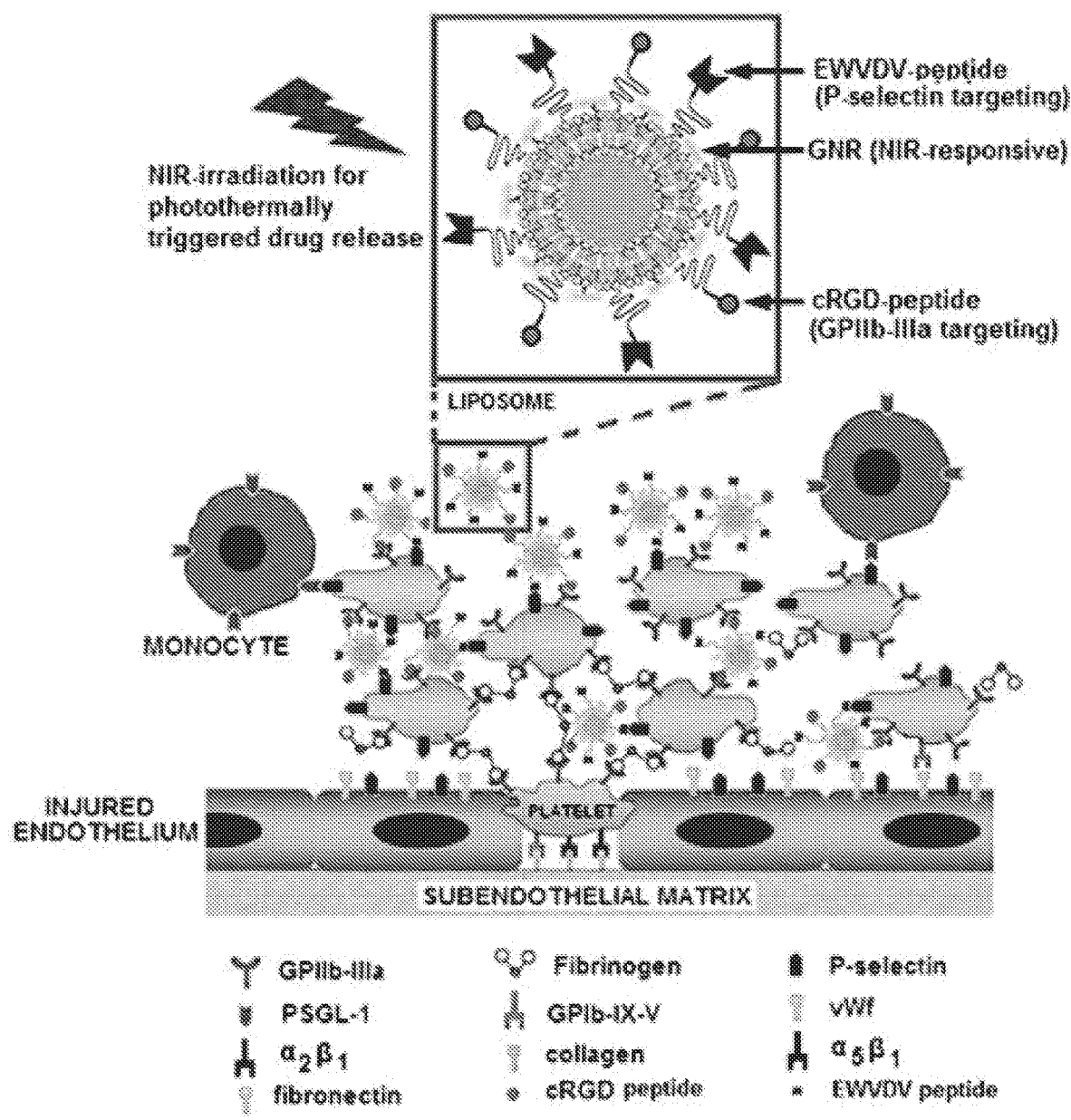
FIG. 12 is a schematic illustration showing the design of liposomal constructs surface-functionalized with two types of ligands (SEQ ID NO: 1 and SEQ ID NO: 3) for simultaneous targeting of GPIIb-IIIa integrin and P-selectin expressed at high quantity on the membrane surface of activated platelets involved in thrombotic and inflammatory events in vascular disease and further surface functionalized with Gold Nanorods (GNRs) allowing for the NIR-triggered release of a drug from the liposomal construct.
Figure 27A:
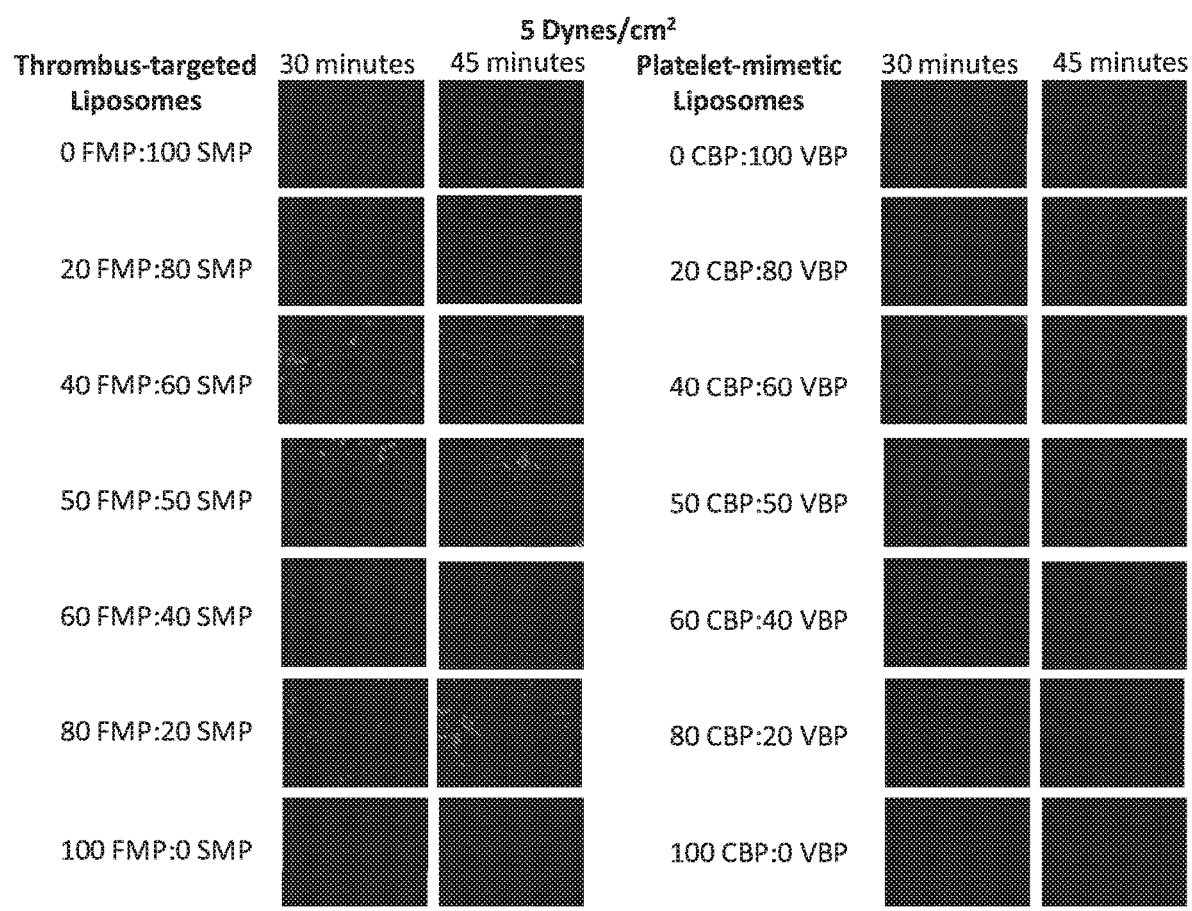
FIGS. 27(A-C) illustrates selective binding of thrombus-targeted liposomes in accordance with an embodiment of the invention compared to platelet-mimetic liposomes at varying ratios of ligands directed to GPIIb-IIIa (FMP) and P-selectin (SMP) and von Willebrand factor-binding peptides (VBPs) and collagen-binding peptides (CBPs) at a flow rate of (A) 5 Dynes/cm$^2$, (B) 25 Dynes/cm$^2$ and (C) 55 Dynes/cm$^2$.
Figure 27B:
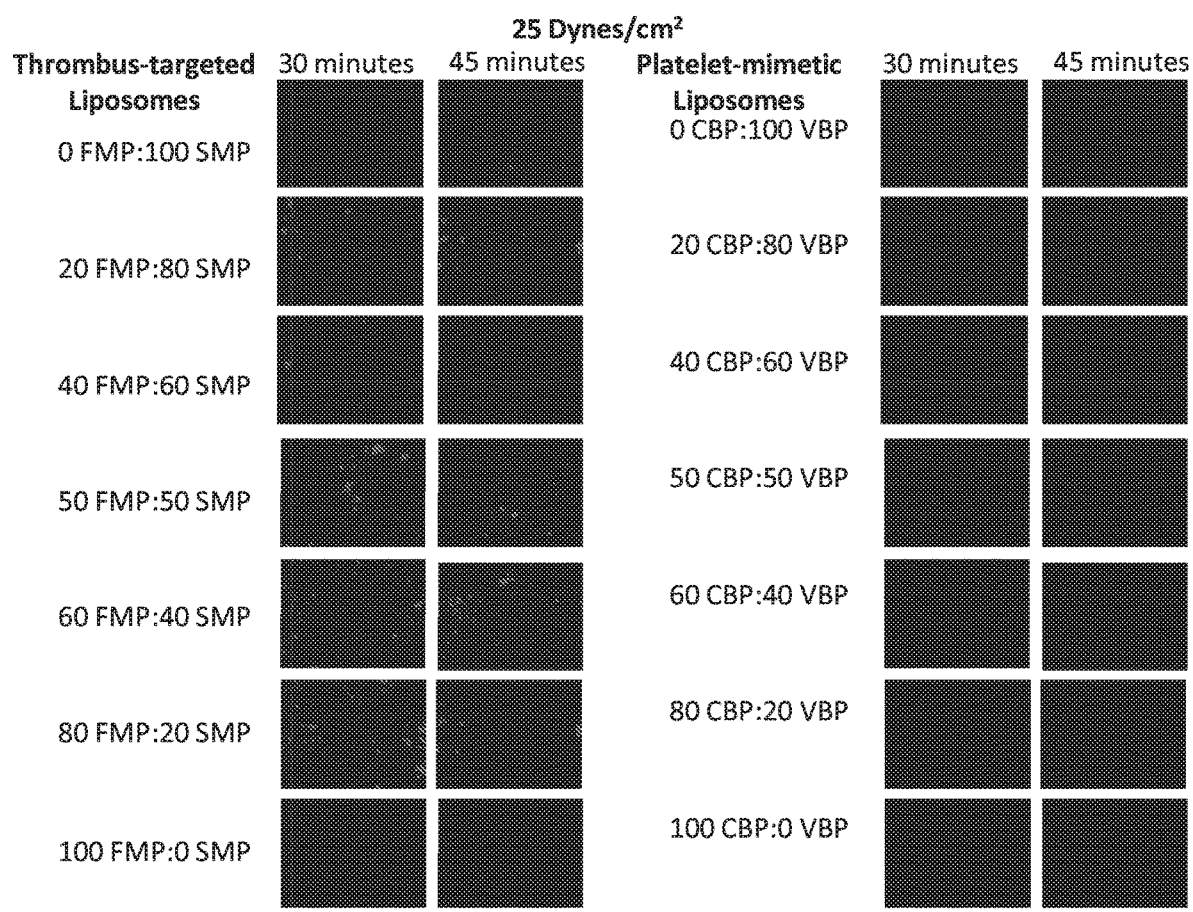
Figure 27C:
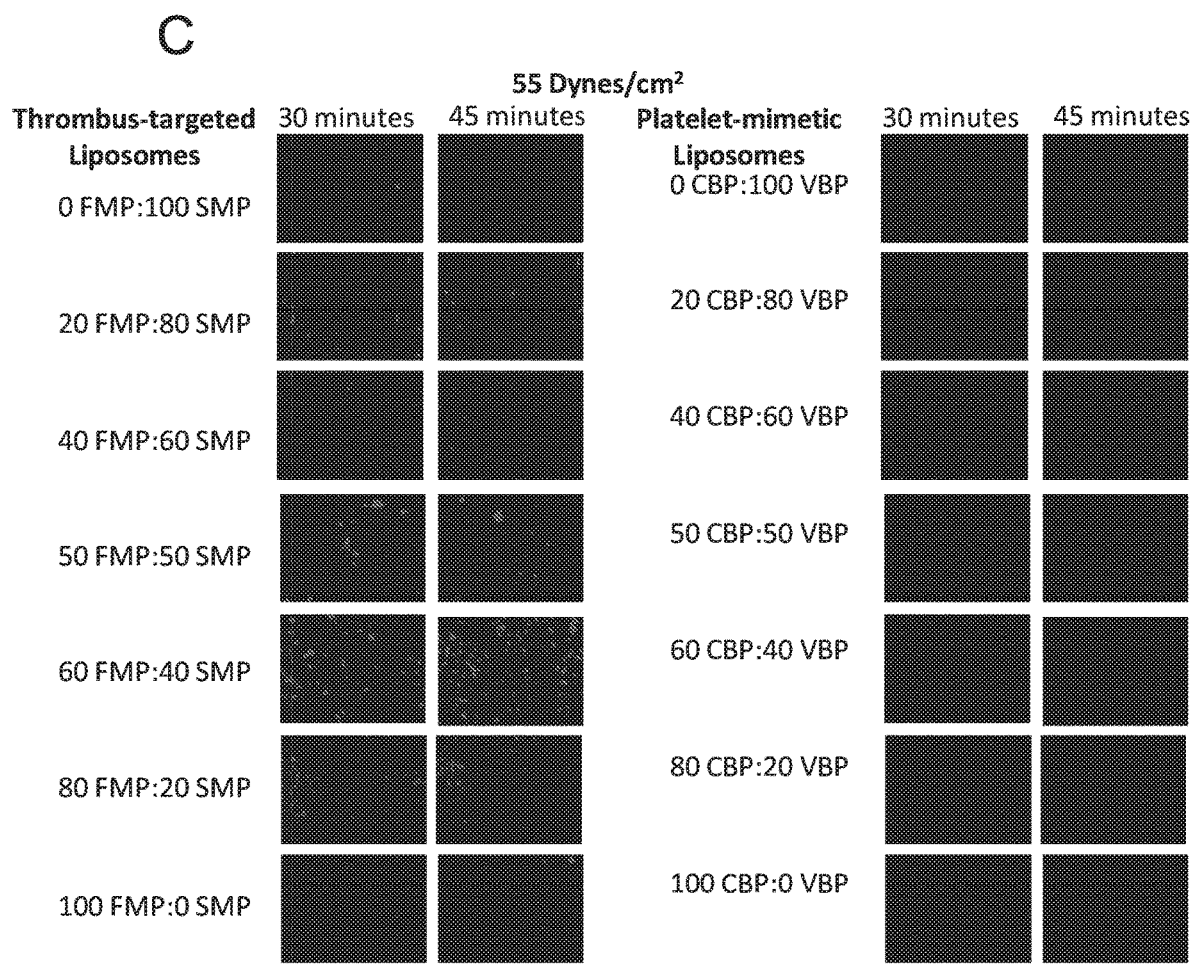

Nanovehicle Binding to Active Platelets Using Fixed Mole % but Varying Ratios of Ligands Directed to GPIIb-IIIa and P-Selectin FIGS. 11a-c show that varying the ratios of surface FMP (fibrinogen mimetic protein, the RGD motif) and SMP (selectin p ligand (SELPLG) mimetic protein) while maintaining a fixed mole % of total ligands directed to GPIIb-IIIa and P-selectin, allows for achieving enhanced binding and retention to activated platelets under flow under a range of flow condition (5-55 dynes/cm$^2$). FIG. 27 shows that multi-receptor targeted strategy results in higher binding and retention of nanovehicles on active platelets under flow conditions, compared to platelet-mimetic liposomes having varying ratios of von Willebrand factor-binding peptides (VBPs) and collagen-binding peptides (CBPs).

Example 2

Figure 16:
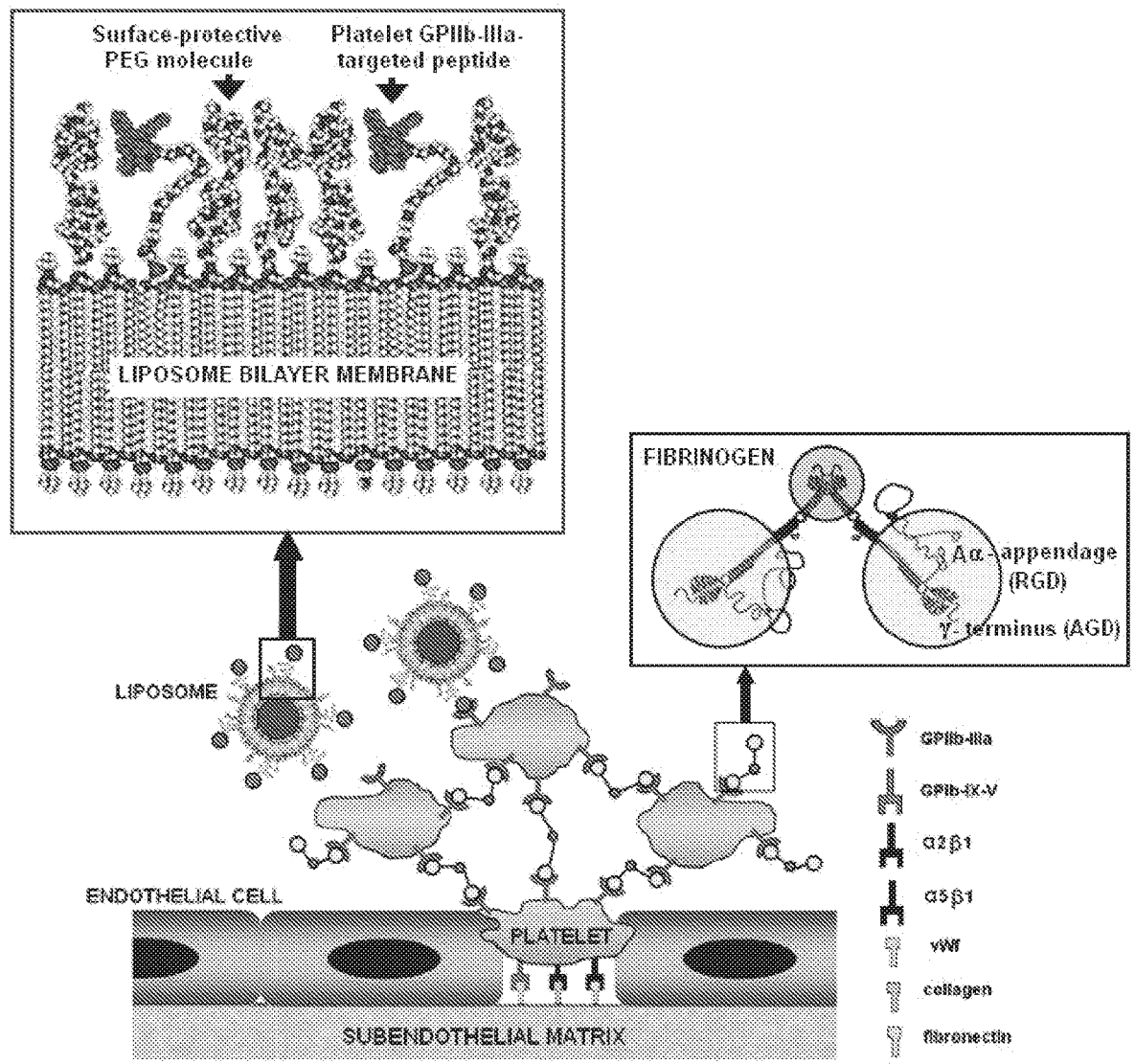
FIG. 16 illustrates a schematic representation of liposomes surface-modified with fibrinogen-mimetic peptides for targeting integrins GPIIb-IIIa on activated platelets at a site of vascular injury in accordance with an embodiment of the present application.

Affinity Manipulation of Surface-Conjugated RGD-Peptide to Modulate Binding of Liposomes to Activated Platelets We postulated that modification of liposome surface with GPIIb-IIIa-specific RGD motifs will result in enhancement of platelet affinity, when compared with linear RGD (lRGD) motifs. The cyclic RGD peptide, CNPRGDY(OEt)RC (SEQ ID NO:3) (terminal cysteines (C) cyclized through disulfide), has been reported to have high affinity and selectivity for GPIIb-IIIa ($\alpha_{IIb}\beta_3$,), compared with other RGD-recognizing receptors like $\alpha v\beta_3$, $\alpha v\beta_5$, and $\alpha_5\beta_1$. Hence this cyclic RGD peptide (cRGD) was developed by solid phase synthesis and conjugated to lipid for incorporation into liposomes, such that the peptide ligands stay displayed on the liposome surface. FIG. 16 shows a schematic model of liposomes surface-modified by fibrinogen-mimetic cRGD-peptide for active platelet-selective thrombus-targeted delivery. Liposomes surface-modified with moderate affinity linear RGD and non-specific linear RGE motifs were used as comparison controls. The interaction of the surface-modified liposomes with activated platelets was studied in vitro by microscopy and flow cytometry and ex vivo by microscopy.

Reagents and Supplies

All amino acid derivatives and peptide synthesis reagents were purchased from Anaspec Inc. All lipids were purchased from Avanti Polar Lipids and NOF America Corp. For fluorescence studies 1-palmitoyl-2-[12-[(7-nitro-2-1,3-benzodiazol-4-yl)]amino]dodecanoyl]-sn-glycero-3-phosphocholine (PDPC-NBD, emission 534 nm, green fluorescence) was purchased from Avanti Polar Lipids and, AlexaFluor-546-tagged human fibrinogen (AlexaFluor-546-Fg, emission 573 nm, red-orange fluorescence) was purchased from Invitrogen and stored at −20° C. prior to use. Cholesterol, bovine serum albumin (BSA), phosphate buffered saline (PBS) and sodium citrate were obtained from Sigma Aldrich. Mass spectrometry and microscopy supplies were used from stock at respective facilities at Case Western Reserve University.

Development of Peptides and Peptide-Lipid Conjugates

An 11-residue linear RGD-containing peptide (GSSSGRGDSPA(SEQ ID NO: 2), lRGD), a 9-residue linear precursor of cRGD peptide (CNPRGDY(OEt)RC (SEQ ID NO:3) and an 11-residue RGE-containing negative control peptide (GSSSGRGESPA (SEQ ID NO:7), lRGE) were synthesized using standard FMoc chemistry by solid-phase peptide synthesizer (ABI433A, Applied Biosystems). For cRGD synthesis, the terminal cysteine residues of the linear precursor were cyclized by a disulfide bond using ferricyanide-mediated oxidation process. All peptides were purified by HPLC and chemical purity was confirmed by mass spectrometry (MALDI-TOF). Peptide-lipid conjugates were prepared following using known methods. For this, peptides, while still on the resin, were reacted through their N-terminal, to an N-hydroxysuccinimide (NHS)-activated polyethylene glycol carboxyester derivative of distearoylphosphatidylethanolamine (DSPE-PEG-COO-NHS, from NOF America Corporation) and the resultant lipid-peptide conjugates were then cleaved from the resin, purified by dialysis and characterized by mass spectrometry. For lipid-cRGD conjugate, the linear peptide precursor was conjugated to lipid first and the cyclization via disulphide bond was performed subsequently.

Platelet-Affinity of Free Peptides

Affinity of free lRGD and cRGD peptides to bind activated platelets was characterized by 'half maximal Inhibitory Concentration' ($IC_{50}$) value, which, in our assays, was the concentration of peptide required to inhibit fibrinogen-mediated platelet aggregation in platelet-rich plasma (PRP) by 50%, in an aggregometry (Bio/Data, PAP-4) set-up. PRP was prepared from citrated human whole blood by centrifugation at 800 RPM for 15 min at 25° C. 50 µl aliquots of PRP were warmed to 37° C. for 2 minutes, incubated with various concentrations of lRGD and cRGD peptide in the presence of agonist adenosine di-phosphate (ADP, 10 µM) and the maximal aggregation percentage was determined while stirring for 15 min. Consequently, from the maximal aggregation percentage and comparison to aggregation without peptides, inhibition percentage was determined.

Preparation of Peptide-Modified Liposomes

All liposomes were prepared by reverse-phase evaporation followed by extrusion through nanoporous (100 nm) Nuclepore polycarbonate membrane, as described previously for our lRGD-liposomes. In all formulations, the final peptide-lipid conjugate content was kept at 1 mol %, which is lower than our previously reported lRGD-liposome formulations with 5 mol % peptide-lipid conjugate. The rationale was that if liposome surface-modification with a higher affinity peptide (e.g., cRGD) has an enhancing effect on platelet binding, the enhancement will be more sensitive and discernible at low peptide concentrations. PDPC-NBD was incorporated at 1 mol % in the formulations as a fluorescent probe. Liposome size and stability were characterized and monitored by dynamic light scattering using a Model 90Plus Brookhaven Instruments Corp Particle Size Analyzer for 30 days from the day of liposome preparation.

Microscopy Analysis of Liposome Binding to Platelets In Vitro

Monolayers of platelets were adsorbed from human platelet suspension onto collagen III-coated glass coverslips following similar methods as we have previously described for our lRGD-liposome studies. 3 µl of ADP (10 µM) in 120 µl PBS was added onto the platelet-adhered coverslips to ensure sufficient activation of adhered platelets. The presence of surface-adsorbed platelets was confirmed by staining with fluorescein isothiocyanate (FITC)-tagged anti-GPIIb-IIIa monoclonal antibody (FITC-anti-CD41a mAb, from BD BioSciences) and observing with a Nikon Diaphot epifluorescence microscope. The 'activated' state of the adherent platelets was confirmed by scanning electron microscopy (SEM) of coverslip samples. For this purpose, the coverslip-adhered platelets were fixed in 2.5% glutaraldehyde for 2 hours at 4° C., subjected to progressive dehydration with graded series of ethanol solutions and finally critical point dried in liquid $CO_2$. The SEM analysis was done by attaching the platelet-adhered coverslips to sample stubs and sputter coating with platinum followed by observation with a Hitachi S-4500 field emission electron microscope with an accelerating voltage of 5 kV.

For fluorescent liposome binding studies, coverslip-adhered platelets were co-incubated with PDPC-NBD labeled lRGD, cRGD or lRGE-modified liposomes (diluted to a final concentration of 2.5 µM) and AlexaFluor-546-Fg in presence of 5 mM $CaCl_2$, for 1 hr at room temperature in the dark. The [fibrinogen:liposome] ratio in the incubation assays was maintained at 400:1 by mole, to provide a physiologically relevant competitive environment. Subsequently the coverslips were washed with PBS, fixed in 1% paraformaldehyde (PFA) for 30 min at 37° C., and mounted on glass slides to be imaged by the epifluorescence microscope for simultaneous detection of NBD and AlexaFluor-546 fluorescence. A 40× oil-immersion objective was used to visualize fluorescence from platelets. Images were collected in MetaMorph™ (Universal Imaging Corp.), using an exposure time of 500 ms and intensity analysis was performed in the software accordingly. Fluorescence intensity was recorded as mean intensity per pixel area for statistical analysis. All coverslips were prepared in duplicate, and at least three fields were examined for each well.

Flow Cytometry Analysis of Liposome Binding to Platelets In Vitro

The effect of platelet activation on liposome binding was studied by a FACScan flow cytometer (Becton Dickinson) with a 488 nm laser and three color detector. For cytometry analysis whole blood aliquots with different platelet activation levels were used. The level of platelet-activation was assessed by simultaneous fluorescence staining of platelet integrin GPIIb-IIIa (with FITC-anti-CD41a) and P-Selectin (with PE-anti-CD62P). Previously we have reported on detecting progressive activation of platelets in freshly drawn blood with addition of agonists (e.g., ADP) and have confirmed that binding of RGD-modified liposomes to platelets increased in an activation-dependant manner. Following a similar protocol, whole blood aliquots containing predominantly activated platelets were incubated with PDPC-NBD-labeled cRGD-, lRGD-, or lRGE-modified liposomes at a final concentration of 500 µM total lipid. For the liposome incubated samples, FITC-anti-CD41a labeling was not used, while PE-anti-CD62P labeling was still used as an activated platelet marker. Simultaneous PE and NBD fluorescence, for gated platelet populations, was analyzed for ~20,000 events (counts) per sample aliquot and fluorescence data were recorded accordingly.

In Vivo Interaction of Surface-Modified Liposomes with Activated Platelets and Ex Vivo Imaging and Analysis For our in vivo model, an acute vascular injury was created by a balloon catheter-induced endothelial denudation of the luminal wall in the left common carotid of Lewis rats. After induction of anesthesia with an intraperitoneal injection of xylazine and ketamine cocktail, a midline cervical incision was made to expose the left external carotid artery. The external carotid artery was ligated, and the internal carotid artery was ligated temporarily. A 2F Fogarty balloon catheter (Baxter Healthcare Corp) was introduced through the arteriotomy site of the external carotid artery. The catheter was passed into the aortic arch, and the balloon was distended with saline until a slight frictional resistance was felt on traction. The catheter was withdrawn through the left common carotid with a slight rotational movement to ensure endothelial denudation of the luminal wall. The insertion and retraction procedure was repeated three times to induce sufficient vascular injury and hence an acute thrombotic environment. Subsequently, blood perfusion through the injury site was re-established by releasing the temporary ligation and maintained for 1 hr to allow platelet adhesion, activation and aggregation. To ascertain the presence of activated thrombotic platelets, two animals were sacrificed, their injured carotid vessel sections excised and after careful sample preparation, imaged with SEM. After the 1 hr blood reperfusion period, 25 µl of NBD-labeled cRGD-, lRGD- or lRGE-liposome suspension was injected into the ascending aorta proximal to the injury site. All vessels branching from the aorta, except the injured carotid artery, were ligated to maximize the flow of liposomes along with the blood through the injury site. The blood (hence liposome) flow was maintained for 15 min, following which, the rats were euthanized, and the injured vessel was gently flushed with saline through the aorta, to remove artifacts. The injured artery section was excised, and immersed in 4% PFA solution for fixing. The fixed artery section was then cut open longitudinally and mounted on glass slides with the luminal injured liposome-exposed wall facing up. The exposed wall was imaged with a fluorescence microscope for NBD fluorescence.

Data Analysis

Statistical analysis, where applicable, was performed in Microsoft Excel. A two tailed, unpaired student's t test (assuming unequal variance) was performed to compare the difference in fluorescence intensity of platelets stained by test and control liposomes in the in vitro and in vivo assays. Significance was considered as $p<0.05$. All data was noted as mean±SD.

Results
Development of Peptides and Lipid-Peptide Conjugates

FIG. 17 shows the peptide sequence structure and representative mass spectrometry data of the (17a) linear and (17b) cyclic RGD peptides developed for targeting GPIIb-IIIa. These peptides were conjugated to lipid (DSPE-PEO-NHS) by amide bond formation between amino terminal of peptide and activated carboxyl terminal of lipid-PEG. FIG. 17c shows a representative MALDI-TOF analysis data of the product after conjugation of the cRGD peptide to DSPE-PEG-COO-NHS on resin, followed by cleavage. As evident from 17c, the mass spectrometry results of the crude product from the lipid-peptide conjugation reaction followed by cleavage from resin, showed presence of residual unconjugated peptide and a broad 'hedgehog' peak for the conjugated lipopeptide. The 'hedgehog' appearance of the peak is attributed to the polydispersity of the PEG spacer block in the commercial DSPE-PEG-COO-NHS. The lipopeptide product was purified from unconjugated free peptide by HPLC and dialysis.

Verification of Higher Affinity of the cRGD Peptide

Figure 18:
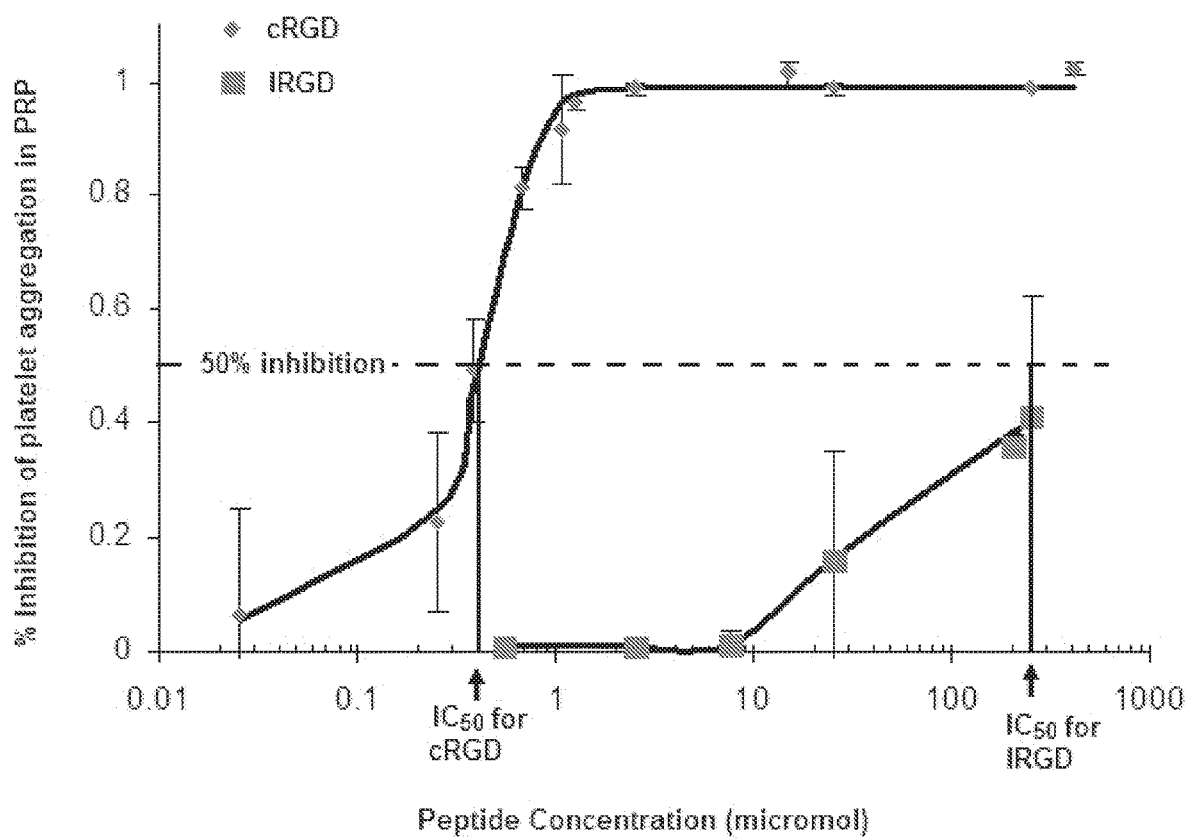
FIG. 18 illustrates the IC$_{50}$ estimation by aggregometry assay for free lRGD and cRGD shows lower IC$_{50}$ for cRGD by ~2 orders of magnitude, compared to lRGD.

FIG. 18 shows the effect of free peptide concentration (lRGD and cRGD) on the inhibition of platelet aggregation, as studied by aggregometry assays. As evident from the result, free cRGD causes 50% inhibition of platelet aggregation (dotted line in FIG. 17) at a much lower peptide concentration compared to free lRGD. 'Affinity' is a kinetic parameter, while 'specificity' is a thermodynamic parameter. In our assays, both the GPIIb-IIIa-specific peptides (lRGD and cRGD) try to kinetically compete with natural ligand fibrinogen in binding active platelet GPIIb-IIIa and hence prevent fibrinogen-mediated platelet aggregation. The higher affinity peptide can outcompete fibrinogen (therefore cause 50% inhibition of platelet aggregation) at low peptide concentrations while the lower affinity peptide requires much higher concentration to gain the kinetic advantage. Hence 'affinity' is directly correlated with the $IC_{50}$ value and the value for cRGD was found to be about 1000 times lower than that for lRGD. The significantly higher affinity of cRGD was thus established.

Dynamic Light Scattering Analysis of Liposome Size Distribution and Stability

The effective diameter of liposomes in various batches was found to be ~150 nm, when measured fresh after extrusion. The liposome suspensions were stored in vials at 4° C. and the size distribution was monitored for 30 days using dynamic light scattering. No significant variation in effective diameter of liposomes was found for the 30 day period indicating stable non-aggregating vesicles.

Microscopy Studies of Platelet-Liposome Interaction In Vitro

In order to validate our postulation that surface-modification of liposomes with higher affinity peptide provides a way to enhance liposome binding to activated platelets in a physiologically relevant competitive environment, platelet-liposome interaction was studied in vitro, where liposomes and fibrinogen were allowed to co-incubate with collagen-III adhered activated platelets. The presence of surface-adhered active platelets was confirmed by SEM, as shown in FIG. 19A. The platelets co-incubated with green fluorescent liposomes and red-orange fluorescent Fg, showed dual fluorescence due to simultaneous binding. The Fg fluorescence was similar for samples co-incubated with lRGD- or cRGD-liposomes (FIGS. 19, B1 and C1). However, platelets co-incubated with cRGD-liposomes (FIG. 19, C2) showed significantly greater (p<0.005) NBD (green) fluorescence compared to platelets co-incubated with lRGD-liposomes (FIG. 19, B2). The mean NBD fluorescence intensity per pixel area of platelets incubated with cRGD-liposomes was found to be significantly higher (FIG. 19, D) compared with platelets incubated with the lRGD-liposomes, for triplicate batches. This indicates that in a competitive environment cRGD-liposomes bind activated platelets at levels significantly higher than lRGD-liposomes.

Flow Cytometry Studies of Platelet-Liposome Interaction In Vitro

The microscopy results were complimented by flow cytometry assays, where whole blood aliquots were incubated with NBD-labeled peptide-modified liposomes containing 1 mol % lipopeptide by composition. Freshly drawn blood showed only about 25% activated platelets whereas agonist-added (e.g., ADP) blood showed about 99% of the platelets to be activated, as confirmed by co-staining with GPM-Ma-specific and P-selectin-specific markers (FIG. 20. A and B). Blood aliquots containing predominantly resting platelets showed a minimal level of NBD fluorescence staining of platelets over background (unlabeled) when incubated with lRGD, cRGD or lRGE-liposomes (data not shown), suggesting a low degree of lipid exchange-based non-specific staining. However, for agonist-added blood aliquots, incubation with cRGD-liposomes resulted in increase of platelet-associated NBD fluorescence by about an order of magnitude higher compared to that from 1-RGD liposome-incubated aliquots (FIG. 20, C). This confirms that liposome modification with higher affinity cRGD peptide renders higher platelet binding ability compared to modification with moderate affinity lRGD peptide.

Platelet-Binding of RGD-Modified Liposomes In Vivo

SEM was used to confirm the presence of thrombotic activated platelets at the vascular injury site of the rat carotid. FIGS. 21A and 21B show representative SEM micrographs of the carotid artery wall in native state and after catheter-induced injury, respectively. Numerous activated platelets are visible adhered to the injured vessel wall. FIG. 21C is a representative SEM micrograph of an injured artery wall after allowing blood flow for 1 hr, showing considerable thrombosis as evident from the fibrin clot 'mesh'. FIGS. 21D, E, F and G show representative fluorescence microscopy images of the injured carotid section luminal surface exposed to no liposomes and, lRGE-, lRGD- and cRGD-liposomes, respectively. From analysis of mean fluorescence intensity of images from three batches of experiments, it was found that the injured carotid artery exposed to cRGD-liposomes had significantly higher (p<0.01) NBD fluorescence than that exposed to lRGD-liposomes.

Example 3

In Vitro and In Vivo Platelet Targeting By Cyclic RGD-Modified Liposomes

We have developed liposomes whose surfaces are decorated with multiple copies of GPIIb-IIIa specific RGD ligands such that they can specifically bind activated platelets. Here, we report our recent microscopy studies of active platelet binding by liposomes surface decorated with a high affinity cyclic RGD peptide. To assess platelet-binding ability, we incorporated a lipophilic fluorophore within the liposomes and incubated test (surface modified with specific targeting cyclic RGD peptide) and control (surface modified with non-specific RGE peptide) liposomes with activated human platelets, followed by analysis of the incubated cells with fluorescence microscopy and phase contrast microscopy. The resolution limits of fluorescence microscopy resolution makes it difficult to visualize nanoscale liposomes on activated platelets. To obtain this complimentary evidence, we developed the same liposomes where instead of a fluorophore, we incorporated Nanogold® in the liposomal membrane, and analyzed the liposome-incubated platelets by high resolution scanning electron microscopy (SEM). After confirming platelet-targeting in vitro by fluorescence, phase contrast and SEM techniques, the liposomes were tested in vivo in rats in an acute restenosis model created by catheter-induced endothelial denudation of carotid artery. The liposome-exposed injured vessels were excised from euthanized animals and were imaged ex vivo by fluorescence microscopy and SEM.

Materials and Methods

Reagents

Amino acid derivatives, activator (1-hydroxy-1-azabenzotriazoleuronium, HATU), and synthesis resin were purchased from Anaspec, Inc. An activated, purified synthetic polyethylene oxide (PEO) derivative of distearoylphosphatidylethanolamine containing a terminal N-hydroxysuccinimide activated carboxyester (DSPE-PEG-COO-NHS) was purchased from NOF America Corporation. The PEO component had a reported average molecular weight of 2000. Cholesterol, distearoylphosphatidyl choline (DSPC), 1,2-distearoyl-sn-glycero-3-phosphoethanolamine-N-[methoxy (polyethylene glycol)-2000] (abbreviated as DSPE-PEO2000) and 1-palmitoyl-2-[12-[(7-nitro-2-1,3-benzodiazol-4-yl)]amino]dodecanoyl]-sn-glycero-3-phosphocholine (abbreviated as PDPC-NBD) were purchased from Avanti Polar Lipids. For the synthesis of nanogold labeled liposomes, dipalmitoyl phophatidyl ethanolamine Nanogold® (abbreviated as DPPE-Nanogold®) was purchased from Nanoprobes (Yaphank, N.Y.) and refrigerated at 2-8° C. Bovine serum albumin (BSA), human collagen III, phosphate buffered saline (PBS), HPLC grade solvents and sodium citrate were obtained from Sigma Aldrich (St. Louis, Mo.). For rat platelet staining, FITC-conjugated mouse anti-rat CD42d (staining rat platelet glycoprotein V) monoclonal antibody was obtained from BD Biosciences. For in vitro platelet studies, human blood was obtained from aspirin-refraining consenting donors within the department of Biomedical Engineering at Case Western Reserve University.

Figure 22:
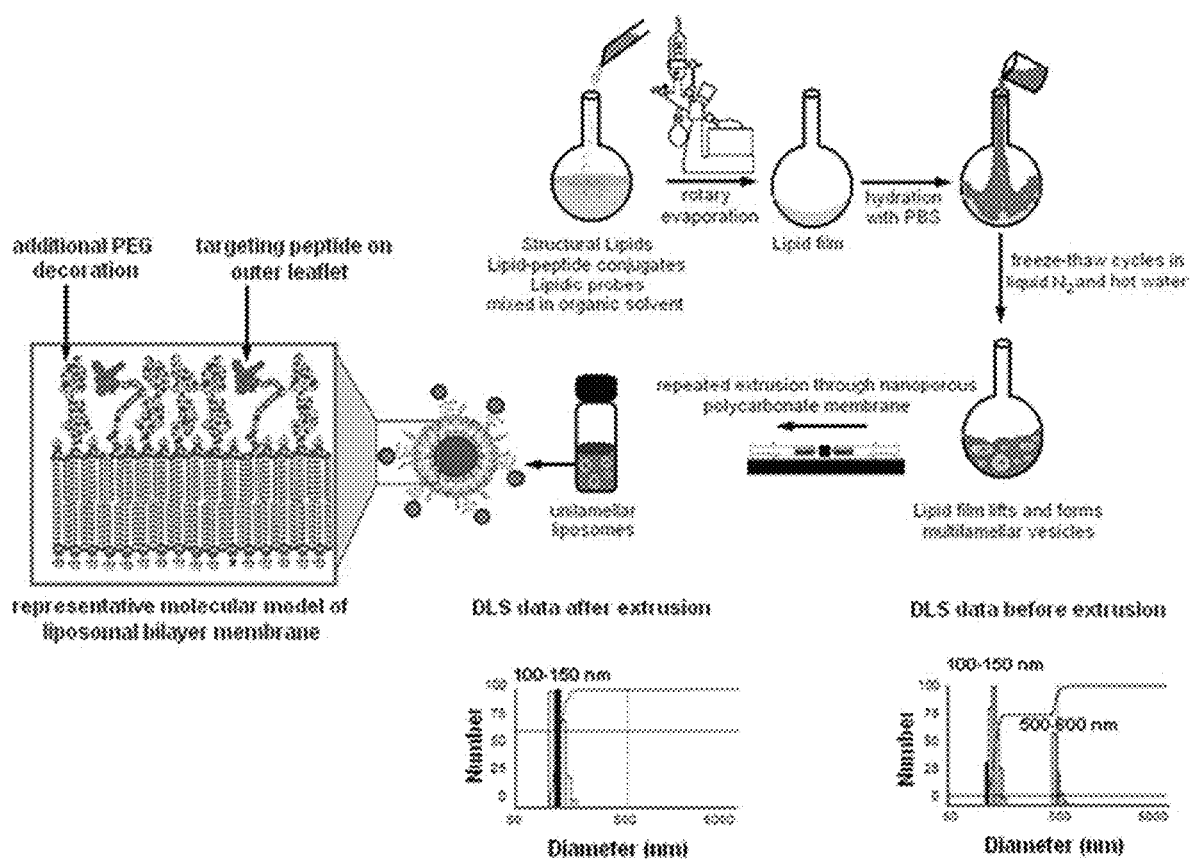
FIG. 22 illustrates a schematic diagram of an exemplary method of liposome preparation including a molecular model representation of the lipid bilayer membrane of the liposome, and the dynamic light scattering (DLS) analysis of liposome size distribution before and after extrusion through nanoporous membrane.

Synthesis of Peptide Ligands, Lipid-Peptide Conjugates and Peptide-Decorated Liposomes The cyclic RGD-peptide, namely, CNPRGDY(-OEt)RC (SEQ ID NO:3) (designated as c-RGD, with terminal Cysteines cyclized), and a negative control peptide GSSS-GRGESPA (SEQ ID NO:7) (designated as RGE) were synthesized by solid-phase peptide synthesis using standard 9-fluoromethoxycarbonyl (Fmoc) chemistry. The rationale for choosing this particular cyclic RGD-peptide sequence is based on $IC_{50}$ values of cyclic peptides in GPIIb-IIIa binding assays reported in literature. The details of the peptide synthesis and the subsequent carbodiimide-mediated conjugation of amine-terminated peptide to N-hydroxysuccimimide (NHS)-activated carboxyl terminal of DSPE-PEG-COOH, followed by cleavage of this lipid-peptide conjugate from the resin, purification (by HPLC and dialysis) and characterization (by MALDI-TOF mass spectrometry), and subsequent formulation into liposomes using reverse phase evaporation and extrusion methods, have been described elsewhere. In the liposome formulations, the concentration of test or control peptide-lipid conjugate was kept as 5 mol % of total lipid. The rest of the formulation consisted of 50 mol % DSPC, 44 mol % cholesterol, and, 1 mol % PDPC-NBD or DPPE-Nanogold. Liposomes surface-decorated with cyclic RGD peptide will be denoted as cRGD-liposomes and those decorated with RGE peptide will be denoted as RGE-liposomes henceforth. Dynamic light scattering (DLS) studies with a Brookhaven Model 90 Plus Particle Size Analyzer showed the average liposome size to be around 150 nm for all batches. FIG. 22 shows a schematic of liposome preparation and representative DLS data for liposomes before and after extrusion.

Fluorescence and Phase Contrast Microscopy Studies and Flow Cytometry Studies In Vitro Collagen-coated glass coverslips bearing monolayer of human platelets, activated by agonist ADP, were prepared as described elsewhere. Adhesion of activated platelet monolayer on coverslips was confirmed by staining representative coverslips with fluorescein isothiocyanate (FITC)-tagged mouse anti-human CD41a monoclonal antibody that stains platelet GPIIb-IIIa, and observing the fluorescence (λemission ~525 nm, green fluorescence) using a Nikon Diaphot inverted microscope containing a filter cube with a 450-490 nm excitation filter, a 510 dichroic mirror and a 520-560 nm bandpass filter. After confirming presence of platelets, similar platelet-adhered coverslips were incubated with test cRGD liposomes or control RGE-liposomes (8 μl with 25 μM total lipid per coverslip) containing PDPC-NBD as the fluorescent label. The liposome incubation was done in presence of 5 mM CaCl2 solution since the interaction of RGD to active platelet GPIIb-IIIa is facilitated by Ca++ ions. The incubation was maintained for 1 hr in the dark. Afterwards the coverslips were gently washed with PBS, mounted on glass slides and imaged by the fluorescence microscope using the same filter parameters as that for FITC fluorescence.

Parallel phase contrast image of the same field of view was obtained on the same microscope, by shutting off the fluorescence laser, turning on the phase contrast light source and changing the objective from fluorescence to a phase contrast one, at same magnification. To establish that the specific binding of cRGD-liposomes is predominantly to activated platelets compared to quiescent platelets, we performed flow cytometry assays similar to that described in previous publications from our group. Briefly, NBD-labeled cRGD liposomes were incubated with aliquots of freshly drawn human whole blood with or without the addition of agonist ADP. We have previously shown 17 by flow cytometric analysis of GPIIb-IIIa and P-selectin co-expression on the platelet surface, that freshly drawn human blood has about 25% platelet population in activated state due to procedural effects (blood draw, contact with syringe, contact with storage tube etc.). Upon addition of agonist (ADP or TRAP), this activation level increases to about 98%. NBD-labeled cRGD liposomes were incubated at a concentration of 500 μM total lipid with 10 μl of human whole blood aliquot without pre-incubation or with pre-incubation of ADP. Following 30 min of liposome incubation, the aliquots were analyzed in a Becton-Dickinson FACScan flow cytometer for NBD fluorescence. All aliquots were measured in triplicate and approximately 15000 counts were recorded per aliquot. Aliquots without any liposome incubation were used as 'unlabeled' controls. The NBD fluorescence intensity from aliquots without liposome incubation, aliquots with liposome incubation but without ADP pre-incubation, and aliquots with liposome incubation after ADP pre-incubation, were recorded as histograms and the plots were overlaid for comparison.

SEM Studies In Vitro

Platelets were adhered from suspension onto collagen III-coated coverslips in presence of ADP as described previously. Presence of activated platelets adhered onto the collagencoated coverslips were first confirmed by SEM to obtain results complimentary to the fluorescence studies. For this, the platelet-incubated coverslips were fixed in 2.5% glutaraldehyde for 2 hours at 4° C., washed with PBS, dehydrated with graded series of ethanol solution (10, 30, 50, 70, 90, 95, and 100%) and critical point dried in liquid CO2. The SEM imaging was done by attaching the coverslips to sample stubs and sputter coating with platinum followed by observation with a Hitachi S-4500 field emission scope. After confirmation of the presence of activated adhered platelets, similar samples were incubated with Nanogold-incorporated test (cRGD) and control (RGE) liposomes for 1 hour at room temperature, in presence of CaCl2. Liposome-incubated coverslips were again washed with PBS to remove liposome suspension, fixed in 2.5% glutaraldehyde for 2 hours at 4° C., rewashed with PBS, dehydrated with graded series of ethanol solution, critical point dried in liquid CO2 and analyzed with SEM using same instrument as described above. The microscope was operated in both secondary and back-scatter electron detection modes with an accelerating voltage of 5 kV. All images were saved directly with a digital image acquisition system (Quartz PCI).

Ex Vivo Microscopy Studies on Platelet-Targeting of Liposomes in a Rat Carotid Injury Model The catheter-induced acute injury model in rat carotid has been described elsewhere. This procedure of carotid injury has been utilized in several studies regarding role of platelets and other cells and biomolecules in regulating restenotic and intimal events. Following injury, the right common carotid and the descending aorta were ligated. The blood flow was reestablished (repurfusion) to allow flow of blood only through the injured left carotid vessel. The blood flow was resumed for 1 hr or 2 hrs to allow activation, adhesion and aggregation of platelets at the injury site due to an acute thrombotic/restenotic environment. Four animals, two immediately after injury and two after 1 hr reperfusion, were sacrificed and the injured vessel sections were excised and washed gently in PBS. Uninjured carotid sections were also excised from the already sacrificed animals for image analysis and comparison purposes. All sections were cut open longitudinally to expose the injured surface. One uninjured section and one 1 hr-repurfused injured section were subjected to incubation with FITC-tagged mouse anti-rat CD42d monoclonal antibody (emission~525 nm, green fluorescence) which stains for rat platelet glycoprotein GPV 24. Following incubation for 1 hr in the dark, the sections were fixed with 4% paraformaldehyde (PFA), washed gently with PBS, mounted on glass slides with luminal surface exposed and imaged with epifluorescence microscope using the same filter and objective specifications as used for the in vitro studies. The other uninjured, injured and repurfused sections were fixed in 3.0% glutaraldehyde in PBS at 4° C. overnight, washed with 50 mM glycine in PBS to remove excess aldehydes, and then washed with distilled water. Following this, the sections were dehydrated in a graded series of ethanol solutions as described previously for the in vitro SEM samples, critical point dried in liquid $CO_2$, mounted on sample stubs, sputter coated with platinum and observed with the previously mentioned EM instrument in both secondary and back-scatter modes with an accelerating voltage of 5 kV. The fluorescence and the SEM analyses of the injured carotid sections vs uninjured sections were done to confirm the presence of activated adhered platelets in the acute injury environment of our model. Following confirmation, similar animals were exposed to fluorescently labeled or Nanogold-labeled test and control liposomes. At the end of the 1 hr or 2 hr blood reperfusion period through the injured vessel, NBD-labeled or Nanogold-labeled cRGD- and RGE. Liposomes were injected into the left ventricle of the rat heart to allow the flow of liposomes along with the blood pumped into the injured carotid. For the ex vivo imaging studies, statistical power calculations were based on the area of coverage of the injured luminal surface by fluorescently labeled liposomes, as obtained by morphometric analysis (by Metamorph and Image J) of digital images. General background levels appear to be ~5% of the area. Our power calculation was based on seeing a 100% increase (to 10% coverage) with 80% power. Based on these parameters our calculation suggested a sample size of ~4 animals per liposome formulation. For NBD-labeled test and control liposomes, four animals were used per formulation. For Nanogold-labeled test and control liposomes, two animals were used per formulation, since this analysis was more qualitative. After liposome injection, the reperfusion flow was maintained for 15 minutes, at the end of which the rats were sacrificed and the injured vessels were excised, washed gently by PBS and prepared for fluorescence or SEM imaging.

For fluorescence imaging, the sections were fixed in 4% PFA, re-washed with PBS, sliced open longitudinally, and the luminal side was imaged with the previously described inverted epifluorescence microscope for NBD fluorescence. At least eight images were obtained per section. For SEM imaging, the excised tissue sections were sliced open longitudinally, fixed in 3.0% glutaraldehyde, washed with 50 mM glycine and then in distilled water. To facilitate imaging of Nanogold-labeled liposomes within the complex morphology injured tissue, gold autometallography was used to enhance the size of Nanogold. This was achieved using a commercially available autometallography kit "Goldenhance-EM" (Nanoprobes) and following the supplier instructions. The tissues were immersed in the enhancement solution for 15 minutes, which according to the supplier, can increase the Nanogold size to ~20 nm. Control tissue sections, without Nanogold-labeled liposome exposure but with exposure to the Goldenhance solution were prepared to check for non-specific background enhancement in SEM. After enhancement, all sections were washed with distilled water, dehydrated in a graded series of ethanol solutions, critical point dried in liquid $CO_2$ and analyzed with SEM. At least eight images were obtained per tissue section.

Data Analysis

For in vitro and ex vivo fluorescence images of liposome-incubated platelets, surfaceaveraged fluorescence intensity was measured using Metamorph® software. For analysis and comparison purposes, the camera parameters were kept constant for all in vitro studies. For the ex vivo studies, the camera conditions were different from the in vitro conditions, but were kept constant for all ex vivo images. Statistical analysis, where applicable, was performed in Microsoft Excel using a two tailed, unpaired student's t test (assuming unequal variance) to compare the difference in fluorescence intensity. Significance was considered as $p<0.05$. All data was noted as mean±SD. For in vitro and ex vivo SEM studies, the image acquisition parameters were kept constant and the results were compared qualitatively.

Results

In vitro Fluorescence Microscopy Studies and Flow Cytometry Studies on Liposomeincubated Human Platelets FIG. 23 shows representative microscopy images for coverslip-adhered ADP-activated human platelets incubated with (23A) RGE-liposomes and (23B) cRGD-liposomes, in presence of Ca++. FIGS. 23A and 23B are representative of images captured through 10× objective. As evident from the images, qualitatively, the binding of cRGD-liposomes to the activated platelets was considerably higher than that for RGE-liposomes. FIG. 23E shows the mean fluorescence intensity data for samples incubated with RGE-liposomes and cRGD liposomes. Statistical analysis of average fluorescence intensity of images from multiple batches of experiments showed that fluorescence intensity of NBD-labeled cRGD-liposome incubated platelet-adhered coverslips were significantly higher ($p<0.01$) compared to that from RGE-liposome incubated platelet-adhered coverslips, indicating enhanced platelet binding of the cRGD-liposomes. The cRGD-liposome incubated samples were observed further at higher magnification with 60× oil-immersion objective. FIGS. 23C and 23D show representative fluorescence and phase contrast images respectively, with 60× objectives, of the same field of view for a c-RGD-liposome incubated platelet-adhered coverslip. The one-to-one correspondence of the fluorescence spots with activated platelets can be observed from 23C and 23D. Representative NBD fluorescence histograms from flow cytometry analyses are shown in FIG. 23F; liposome incubation with predominantly inactive platelet population (no ADP pre-incubation) resulted in NBD intensity close to that of baseline 'unlabeled' while that with ADP-activated platelets increased NBD fluorescence from the gated platelet population by almost two orders of magnitude. Such analyses further confirmed that the binding of the cRGD-liposomes were specifically enhanced to active platelets, and the non-specific platelet binding of cRGD-liposomes was minimal.

In Vitro SEM Studies on Liposome-Incubated Human Platelets

FIG. 24 shows representative images from SEM studies of platelet-adhered coverslips incubated with Nanogold-labeled cRGD- and RGE-liposomes. FIG. 24A and the enlarged image in FIG. 24B, are representative SEM images of the coverslip surface after the experimental procedure of incubating a suspension of human platelets on the collagen-coated glass coverslips in presence of agonist ADP. As evident from the images, the procedure resulted in formation of an adhered monolayer of highly activated platelets. The highly activated state is emphasized by the 'spread' morphology, highly folded membrane appearance and the numerous pseudopodal extensions of the platelet membrane as seen in FIGS. 24A and 24B. Similar coverslip-adhered platelets were incubated with Nanogoldlabeled cRGD- and RGE-liposomes and imaged with SEM. Due to the highly convoluted appearance of the activated platelet membrane, it is difficult to conclusively distinguish between a membrane fold and a vesicular liposome attached to the membrane from secondary electron images. Hence, backscatter images were also obtained for the same platelets with the rationale that the gold-labeled nanoparticles, if bound to the platelets, will produce enhanced backscatter and hence will enable higher resolution visualization of the nanoparticles, compared to the normal backscatter from platelet membrane folds. FIGS. 24C1 and 24C2 show respectively the secondary electron mode and the backscatter mode images of a representative platelet on coverslips incubated with RGE-liposomes. While the secondary electron mode image shows numerous folds and bulges on the membrane that apparently may look like liposomal particles, the backscatter image of the same platelet shows only minimal contrast-enhancement on the platelet membrane, thereby suggesting that the folds and bulges seen in the secondary electron mode image are mainly convolutions and vesicular protrusions of the platelet membrane itself (e.g., vesiculation into microparticles), with maybe minimal non-specific binding of gold-labeled liposomes by possible lipid exchange. FIGS. 24D1 and 24D2 show respectively the secondary electron mode and the backscatter mode images of a representative platelet on coverslips incubated with cRGD-liposomes. Once again the secondary electron mode image shows folds, bulges and vesicular protrusions on the platelet membrane similar to the RGE-liposome incubated samples. However, backscatter image of the same field shows significant bright contrast of the platelet membrane compared to the representative sample from the RGE-liposome incubated batch. Also, multiple highly contrast-enhanced vesicular structures (highlighted by arrowheads) adhered onto the platelet membrane and the platelet pseudopodal extensions are visible on the representative image from the cRGD-liposome incubated batch. From the scale bar, the size of these structures are around 100-200 nm and hence most possibly they are Nanogold-labeled liposomes. These results suggest enhanced binding and fusion of goldlabeled cRGD-liposomes with the platelet membrane. Considering these results to be complimentary to the results obtained from fluorescence microscopy studies, it can be concluded that the cRGD-liposomes have enhanced binding, specifically to activated platelets, and hence can be promising towards platelet-directed site-selective vascular delivery.

Ex Vivo Microscopy Studies of Liposome-Platelet Interactions in Rat Carotid Injury Model FIG. 25 shows the schematic of experimental procedure (25A), a collection of representative SEM and fluorescent images of the carotid wall before (25B and 25D) and after injury (right after injury, 24E, and, after 1 hr repurfusion, 25C and 25F). FIG. 25 also shows representative fluorescent images of the injured carotid exposed to NBD-labeled RGE-liposomes following 1 hr (25H) and 2 hr (25J) repurfusion, and the injured carotid exposed to NBD-labeled RGD liposomes following 1 hr (25I) and 2 hr (25K) repurfusion, along with the statistical analysis of fluorescent images from all batches of this study (25L). As evident from 25B, the uninjured rat tissue itself has autofluorescence associated with it. The SEM image of the uninjured tissue (25D) shows uniform striated appearance given by luminal lining of cells, while upon catheter-induced injury, acute disruption of the luminal wall is visible (25E). After perfusion of blood through the injury site for 1 hr, staining with FITC-tagged anti-rat CD42d and imaging with epifluorescence microscope revealed numerous adhered platelets on the injured luminal wall (25C). This data was complimented by SEM analyses of similar samples, where numerous adhered platelets were visible on the injured wall (25F) and upon further magnification, platelets were found to be arrested in and adhered to fibrin mesh (25G), signifying an acute thrombotic/restenotic environment. The 15-minute exposure of the injured carotid to NBD-labeled RGE-liposomes (in flowing blood) after repurfusion for 1 hr (25H) and 2 hrs (25J) showed only minimal staining of platelets over the background autofluorescence. The same for NBD-labeled c-RGD-liposomes showed significant platelet staining over background autofluorescence for both 1 hr (25I) and 2 hr (25K) repurfusion situations. Statistical analysis of average fluorescence intensity of images from multiple batches of experiments confirmed this observation (25L). As evident from the representative image 25K, fluorescence microscopy analysis of c-RGD-liposome exposed injured carotid after 2 hr perfusion period also showed indication of acute platelet aggregation and clotting (green fluorescent clumps in 25K). FIG. 26 shows representative secondary mode and backscatter mode SEM images of injured carotid wall exposed to Nanogold-labeled RGE-liposomes (26A1 and 26A2) and cRGD-liposomes (26B1 and 26B2). Secondary electron mode images for both RGE-liposome and cRGD-liposome exposed injured carotid wall looked very similar (26A1 and 26B1), revealing dense fibrin mesh and adhered/arrested platelets. However the backscatter mode images for cRGD-liposome exposed injury site (26B2) showed considerably bright contrast compared to RGE-liposome exposed injury site (26A2). This suggests enhanced binding of gold-labeled cRGD-liposomes to the injury site, most possibly, by design, to the activated platelets adhered and aggregated at the site. Because of the highly irregular three dimensional dense morphology of the thrombotic environment, the dynamic flow environment of the experimental protocol, and the complex ex vivo sample preparation procedures, the intact vessel integrity of platelet-adhered liposomes was probably not maintained in these in vivo experiments, as it was maintained for the static incubation experiments in vitro. Nonetheless, the enhanced brightness of cRGD-liposome exposed tissue suggested enhanced site-specific liposome binding, complimentary to the fluorescence microscopy data of FIG. 25.

From the above description of the invention, those skilled in the art will perceive improvements, changes and modifications. Such improvements, changes and modifications within the skill of the art are intended to be covered by the appended claims. All references, publications, and patents disclosed above are herein incorporated by reference in their entirety.

Having described the invention, we claim:

1. A method of treating vascular disease in a subject, comprising: administering to the subject a therapeutically effective amount of a composition, the composition comprising a heteromultivalent nanoparticle or microparticle construct comprising a therapeutic agent and/or imaging agent, the nanoparticle or microparticle having an outer surface and a plurality of targeting moieties conjugated to the surface of the nanoparticle or microparticle, the first activated platelet targeting moiety comprising a GPIIb-IIIa-binding peptide and the second activated platelet targeting moiety comprising a p-selectin binding peptide, and wherein the nanoparticle or microparticle remains attached to activated platelets in the subject under a hemodynamic shear environment.

2. The method of claim 1, the nanoparticle or microparticle construct comprising a liposome.

3. The method of claim 1, the GPIIb-IIIa-binding peptide comprising a RGD peptide and the p-selectin binding peptide comprising a SEQ ID NO: 1.

4. The method of claim 3, the RGD peptide having SEQ ID NO: 3.

5. The method of claim 1, wherein the first and second activated platelet targeting moieties are conjugated to the nanoparticle or microparticle surface with PEG linkers.

6. The method of claim 1, wherein targeting moieties are spatially or topographically arranged on the nanoparticle or microparticle surface such that the GPIIb-IIIa-binding peptide and the p-selectin binding peptide do not spatially mask each other and the nanoparticle or microparticle is able to bind to an activated platelet with exposed activated platelet receptors and enhance retention of the nanoparticle or microparticle onto activated platelets under hemodynamic flow.

7. The method of claim 6, wherein the ratio of GPIIb-IIIa-binding peptide to p-selectin binding peptide provided on the nanoparticle or microparticle surface is about 80:20 to about 20:80.

8. The method of claim 6, wherein the GPIIb-IIIa-binding peptide and p-selectin binding peptide provided on the nanoparticle or microparticle surface have a total mol % of about 5 to about 20 with respect to total lipid content.

9. The method of claim 1, wherein the therapeutic agent is a thrombolytic agent and the subject is afflicted with an occlusive vascular disease selected from the group consisting of stroke, myocardial infarction, peripheral arterial diseases and deep vein thrombosis.

10. The method of claim 1, the nanoparticle or microparticle construct further comprising a plurality of Golden Nanorods (GNRs) conjugated to the surface, the GNRs allowing photothermal destabilization of the nanoparticle or construct and release of the therapeutic and/or imaging agent in response to near-infrared (NIR) light.

11. The method of claim 1, wherein the occlusive vascular disease is myocardial infarction.

12. The method of claim 9, wherein the thrombolytic agent is alteplase.

* * * * *

```
                        SEQUENCE LISTING

<160> NUMBER OF SEQ ID NOS: 8

<210> SEQ ID NO 1
    <211> LENGTH: 5
    <212> TYPE: PRT
    <213> ORGANISM: Homo sapiens

<400> SEQUENCE: 1

Glu Trp Val Asp Val
    1               5

<210> SEQ ID NO 2
    <211> LENGTH: 11
    <212> TYPE: PRT
    <213> ORGANISM: Homo sapiens

<400> SEQUENCE: 2

Gly Ser Ser Ser Gly Arg Gly Asp Ser Pro Ala
    1               5                   10

<210> SEQ ID NO 3
    <211> LENGTH: 9
    <212> TYPE: PRT
    <213> ORGANISM: Homo sapiens

<400> SEQUENCE: 3

Cys Asn Pro Arg Gly Asp Tyr Arg Cys
    1               5

<210> SEQ ID NO 4
    <211> LENGTH: 9
    <212> TYPE: PRT
    <213> ORGANISM: Homo sapiens

<400> SEQUENCE: 4

Cys Asp Val Glu Trp Val Asp Val Ser
    1               5

<210> SEQ ID NO 5
    <211> LENGTH: 8
    <212> TYPE: PRT
    <213> ORGANISM: Homo sapiens

<400> SEQUENCE: 5

Asp Ala Glu Trp Tyr Asp Val Ser
    1               5

<210> SEQ ID NO 6
```

```
<211> LENGTH: 11
<212> TYPE: PRT
<213> ORGANISM: Homo sapiens

<400> SEQUENCE: 6

Gly Ser Ser Ser Gly Arg Gly Asp Ser Pro Ala
1               5                   10

<210> SEQ ID NO 7
<211> LENGTH: 11
<212> TYPE: PRT
<213> ORGANISM: Homo sapiens

<400> SEQUENCE: 7

Gly Ser Ser Ser Gly Arg Gly Glu Ser Pro Ala
1               5                   10

<210> SEQ ID NO 8
<211> LENGTH: 8
<212> TYPE: PRT
<213> ORGANISM: Homo sapiens

<400> SEQUENCE: 8

Asp Ala Glu Trp Val Glu Val Ser
1               5
```